US007851645B2

(12) United States Patent
Ryu

(10) Patent No.: US 7,851,645 B2
(45) Date of Patent: Dec. 14, 2010

(54) PROCESS FOR CONTINUOUS PRODUCTION OF ORGANIC CARBONATES OR ORGANIC CARBAMATES AND SOLID CATALYSTS THEREFORE

(75) Inventor: J. Yong Ryu, Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 207 days.

(21) Appl. No.: 12/029,283

(22) Filed: Feb. 11, 2008

(65) Prior Publication Data

US 2009/0203933 A1    Aug. 13, 2009

(51) Int. Cl.
C07C 69/96    (2006.01)
(52) U.S. Cl. ..................................... 558/274
(58) Field of Classification Search ................. 558/274
See application file for complete search history.

(56) References Cited

U.S. PATENT DOCUMENTS

| 4,045,464 | A | 8/1977 | Romano et al. |
| 4,554,110 | A | 11/1985 | Mark |
| 4,731,231 | A | 3/1988 | Perry |
| 5,210,268 | A | 5/1993 | Fukuoka et al. |
| 5,231,212 | A | 7/1993 | Buysch et al. |
| 5,354,923 | A | 10/1994 | Schon et al. |
| 5,498,743 | A | 3/1996 | Shih et al. |
| 5,525,126 | A | 6/1996 | Basu et al. |
| 5,565,605 | A | 10/1996 | Tsuneki et al. |
| 5,663,480 | A | 9/1997 | Tsuneki et al. |
| 5,908,946 | A | 6/1999 | Stern et al. |
| 5,954,280 | A | 9/1999 | Kroger et al. |
| 6,017,368 | A | 1/2000 | Steinmann |
| 6,093,842 | A * | 7/2000 | Oyevaar et al. ............. 558/274 |
| 6,147,196 | A | 11/2000 | Stern et al. |
| 6,712,867 | B1 | 3/2004 | Boocock et al. |
| 6,768,020 | B2 | 7/2004 | De Jonge et al. |
| 6,835,858 | B1 | 12/2004 | De Jonge et al. |
| 6,930,195 | B2 | 8/2005 | Buchanan et al. |
| 7,074,951 | B2 | 7/2006 | Ryu et al. |
| 7,288,668 | B2 * | 10/2007 | Ryu et al. .................... 558/274 |
| 7,378,540 | B2 * | 5/2008 | Ryu ............................. 558/274 |
| 2004/0034244 | A1 | 2/2004 | Bournay et al. |
| 2007/0055042 | A1 | 3/2007 | Miyake et al. |
| 2007/0093672 | A1 | 4/2007 | Ryu |
| 2007/0112214 | A1 | 5/2007 | Ryu et al. |
| 2008/0177099 | A1 | 7/2008 | Miyake |
| 2008/0183002 | A1 | 7/2008 | Nisbet et al. |

FOREIGN PATENT DOCUMENTS

| EP | 0363681 | 4/1990 |
| EP | 0636681 | 2/1995 |
| EP | 1629888 | 1/2006 |
| WO | 03066569 | 8/2003 |
| WO | 2009016646 | 2/2009 |

OTHER PUBLICATIONS

Igor N. Martyanov, et al., Comparative study of triglyceride transesterification in the presence of catalytic amounts of sodium, magnesium, and calcium methoxides, Applied Catalysis A: General, 2008, pp. 45-52, 339, Elsevier Science B.V.
Wenlei Xie, et al., Calcined Mg-Al hydrotalcites as solid base catalysts for methanolysis of soybean oil, Journal of Molecular Catalysis A:Chemical, 2006, pp. 24-32, 246, Elsevier B.V.
Zi-Hua Fu and Yoshio Ono, Two-step synthesis of diphenyl cabonate from dimethyl carbonate and phenol using $MoO_3/SiO_2$ catalysts, Journal of Molecular Catalysis A: Chemical, 1997, pp. 293-299, 118.
Peter Ball, et al., Synthesis of Carbonates and Polycarbonates by Reaction of Urea with Hydroxy Compounds, C1 Mol. Chem., 1984, pp. 95-108, vol. 1, Harwood Academic Publishers GmbH, Great Britain.
D. Wang, et al., Synthesis of diethyl carbonate by catalytic alcoholysis of urea, Fuel Processing Technology, 2007, pp. 807-812, 88, Elsevier B.V.
D.C. Bradley, et al., Metal Oxide Alkoxide (Trialkysilyloxide) Polymers, Coordination Chemistry Reviews, 1967, pp. 299-318, 2, Elsevier Publishing Company Amsterdam, The Netherlands.
P. Iengo, et al., Preparation and properties of new acid of catalysts obtained by grafting alkoxides and derivatives on the most common supports, Applied Catalysis A: General, 1999, pp. 97-109, 178, Elsevier Science B.V.
D.C. Bradley, et al., Structural Aspects of the Hydrolysis of Titanium Tetraethoxide, J. Chem. Soc., 1955, pp. 3977-3982.
Zhihui Li, et al Investigation on the deactivation cause of lead-zinc double oxide for the synthesis of diphenyl carbonate by transesterification, Journal of Natural Gas Chemistry 18 (2009) 104-109.

(Continued)

Primary Examiner—Rei-tsang Shiao
(74) Attorney, Agent, or Firm—Osha + Liang LLP

(57) ABSTRACT

Processes for the alcoholysis, inclusive of transesterification and/or disproportionation, of reactants are disclosed. The alcoholysis process may include feeding reactants and a trace amount of soluble organometallic compound to a reactor comprising a solid alcoholysis catalyst, wherein the soluble organometallic compound and the solid alcoholysis catalyst each independently comprise a Group II to Group VI element, which may be the same element in various embodiments. As an example, diphenyl carbonate may be continuously produced by performing transesterification over a solid catalyst followed by disproportionation, where a trace amount of soluble organometallic compound is fed to the transesterification reactor. Also disclosed is a process for reactivating a spent solid alcoholysis catalyst, such as a catalyst useful for transesterifications and/or disproportionations, the process including removing polymeric materials deposited on the catalyst and re-depositing catalytically active metals on the solid catalyst.

14 Claims, 19 Drawing Sheets

OTHER PUBLICATIONS

Maria Concetta Gaudino, et al Titanium-based solid catalysts for transesterification of methyl-methacrylate by 1-butonal: the homogeneous catalysis contribution, Applied Catalysis A: General 280 (2005) 157-164.

Kouzu Masato et al, Heterogeneous catalysis of calcium oxide used for transesterification of soybean oil with refluxing methanol, Applied Catalysis A: General 335 (2009) 94-99.

Kathlene Jacobson, et al, Solid Acid Catalyzed Biodiesel Production From Waste Cooking Oil, Applied Catalysis B: Enviromental 85 (2008) 86-91.

Gong Jinlong, et al, Transesterification of Dimethyl Oxalate with Phenol Owner TiO(sub)2 (/sub)/ SiO (sub 2) (/sub): Catalyst Screening and Reaction, Aiche 54 (2008) 3260-3272.

Y.T. Kim, et al, Deactivation Phenomena of $MoO_3/SiO_2$ and $TiO_2/SiO_2$ during Transesterfication between Dimethyl Carbonate and Phenol, Applied Catalysis A, 352 (2009) 211-215.

Abdillahi Omar Bouh, et al Mono-and Dinuclear Silica-Supported Titanium (IV) Complexes and the Effect of TiOTi Connectivity on Reactivity, J. A, Chem. Soc. 1999, 121, pp. 7201-7210.

Dongshen Tong, et al Transesterification of Dimethyl Carbonate with Phenol over a Bimetallic Molybdenum and Copper Catalyst, React. Kinet. Catal. Lett. vol. 94, No. 1 pp. 121-129 (2008).

Mo et al., A Novel Sulfonated Carbon Composite Solid Acid Catalyst for Biodiesel Synthesis, Catal. Lett. (2008) 123: 1-6, Springer Science+Business Media, LLC.

Search Report and Written Opinion with Notice of Reference Cited dated Oct. 29, 2009 issued in International application No. PCT/US2009/032309 (14 pages).

Weiqing et al, Synthesis of diphenyl carbonate by transesterification over lead and zinc double oxide catalyst, Applied Catalysis A: General 260 (2004) 19-24.

Niu et al., Transesterification of dimethyl carbonate and phenol to diphenyl carbonate catalyzed by titanocene complexes, Catalysis Communications 8 (2007) 355-358.

Li et al., The synthesis of diphenyl carbonate from dimethyl carbonate and phenol over mesoporous $MoO_3$/SiMCM-41, Journal of Molecular Catalysis A: Chemical 289 (2008) 100-105.

Ballesteros et al., Grafting or tethering titanium alkoxo complexes on MCM-41? Strategies to prepare epoxidation catalysts, Microporous and Mesoporous Materials 116 (2008) 452-460.

Chandure et al., Synthesis and biodegradation studies of 1,3-propanediol based aliphatic poly(ester carbonate)s, European Polymer Journal 44 (2008) 2068-2086.

Cao et al., Synthesis of diphenyl carbonate from dimethyl carbonate and phenol using $O_2$-promoted PbO/MgO catalysts, Catalysis Communications 6 (2005) 802-807.

\* cited by examiner

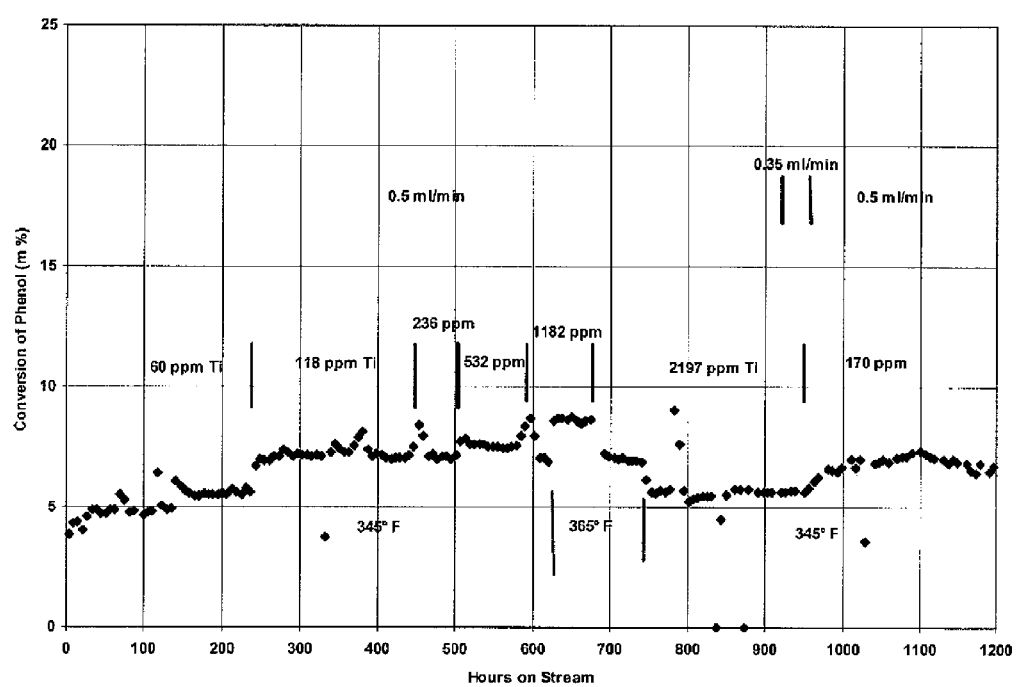

PROCESS FOR CONTINUOUS PRODUCTION OF ORGANIC CARBONATES OR ORGANIC CARBAMATES AND SOLID CATALYSTS THEREFORE

BACKGROUND OF DISCLOSURE

1. Field of the Disclosure

Embodiments disclosed herein relate generally to processes and solid catalysts for reactions involving alcoholysis, transesterification, and disproportionation. More specifically, embodiments disclosed herein relate to processes for the continuous production of organic carbonates, organic carbamates and other products via alcoholysis, transesterification, and/or disproportionation over a solid fixed bed catalyst. A soluble organometallic compound may be continuously fed to the reactor at very low levels to sustain the solid catalyst activity for an extended cycle length.

2. Background

Transesterification, or the exchange reaction of esters with alcohols (an alcoholysis reaction), is an important class of reactions which may be catalyzed by both acid and base catalysts. Examples of transesterification, in general, include chemical reactions involving organic carbonates and carboxylic acid esters as reactants, products, or both. Other transesterification reactions include the production of biodiesel by transesterification of triglycerides with ethanol or methanol. Alcoholysis, in general, is a reaction where one or more functional groups of a compound are replaced by alkoxy or aryloxy group of an alcohol (alkyl or aryl hydroxyl compound). Examples of alcoholysis include chemical reactions involving urea, where amine groups are replaced by alkoxy groups to produce organic carbamates and carbonates.

Carboxylic acid esters are produced by transesterification of a carboxylic acid ester with an alcohol in the presence of acid and base catalyst. Sulfuric acid (homogeneous) and acid resins (solid) are preferred acid catalysts. Soluble bases, such as NaOH and KOH, various Na/K alkoxides or amines (homogeneous), and various basic resins (solid) are preferred base catalysts. Although catalysts can be either homogeneous catalyst or heterogeneous catalyst for the transesterification of carboxylic esters, base catalysts are, in general, more effective than acid catalysts. For example, long chain alkyl methacrylic esters are produced by exchange reaction of methyl methacrylate with a long chain alcohol in the presence of a base catalyst.

Biodiesel may be produced by transesterification of vegetable oils (triglycerides) with methanol or ethanol by using a homogeneous base catalyst, such as sodium methoxide or calcium acetate, as disclosed in U.S. Pat. Nos. 6,712,867 and 5,525,126, and a basic solid catalyst, such as a mixed oxide of zinc oxide and alumina or zinc aluminate (zinc oxide supported on alumina and calcined at a high temperature). Solid zinc aluminate catalysts are disclosed in U.S. Pat. No. 5,908,946 and U.S. Patent Application Publication No. 2004/0034244, for example.

U.S. Pat. No. 5,908,946 discloses a two-step process for producing esters by reacting vegetable oils or animal oils with an alcohol in the presence of solid catalysts such as zinc oxide or spinel type zinc aluminates. In the first step, the conversion of triglyceride is forced to a high conversion, usually higher than 90%. In the second step, the remaining triglycerides, diglycerides and monoglycerides are converted. The transesterifications are performed at a temperature from 230 to 245° C. at about 5.2 bar (about 725 psia). High conversion requires relatively low flow rates of a feed mixture (0.5 $h^{-1}$ or lower space velocity).

U.S. Pat. No. 6,147,196 discloses a process for producing high purity fatty acid esters from plant or animal oil in the presence of a heterogeneous catalyst (zinc aluminate). U.S. Patent Application Publication No. 2004/0034244 relates to a processing scheme for producing alkyl esters from vegetable or animal oil and an alcohol in the presence of a heterogeneous catalyst (zinc aluminate). The esters are produced by transesterification in two fixed bed reactors. High conversion of triglyceride was obtained in the first reactor. After separating glycerol from the first transesterification reaction stream, the remaining unconverted triglyceride, diglyceride and monoglyceride are converted to esters in the second reactor. The transesterification is performed at 200° C., about 62 bar (900 psia) and 0.5 $h^{-1}$ space velocity.

W. Xie et al. (J. Mol. Cat. A: Chem. 246, 2006, pp 24-32) discuss methanolysis of soybean oil in the presence of a calcined Mg—Al hydrotalcite catalyst. The calcined hydrotalcites with an Mg/Al ratio of 3.0 derived from calcinations at 500° C. is a catalyst that can give high basicity and excellent catalytic activity for this reaction. They report the soluble basicity of the hydrotalcites calcined at various temperatures.

Diesel engines emit more particulates and $NO_x$ than gasoline engines. It is reported that dialkyl carbonates are effective in reducing particulates in diesel engine exhaust. According to U.S. Pat. No. 5,954,280, urea and ammonia are effective $NO_x$ reducing agents. But using urea and ammonia for diesel engine has practical problems or inconveniences. U.S. Pat. No. 6,017,368 discloses ethyl carbamate as effective at reducing $NO_x$ from diesel engines. U.S. Pat. No. 4,731,231 (1988) reports that sublimed cyanuric acid can be an effective agent for the elimination or reduction of $NO_x$. High temperature sublimation of cyanuric acid produces isocyanic acid (HNCO), which is believed to be responsible for elimination of $NO_x$. EP 0363681 and EP 0636681 disclose a carbonate ester of an aliphatic triol or tetraol as a component of low smoke lubricating agents.

N-aryl methyl carbamate is produced by reaction of an aromatic amine with a dimethyl carbonate, typically in the presence of a base catalyst due to low reaction rates in the absence of a catalyst. N-aryl methyl carbamate can be decomposed to produce aromatic isocyanate at elevated temperature. For example, toluene dicarbamate is produced by reacting toluene diamine with dimethyl carbonate in the presence of a catalyst. Decomposition of toluene dicarbamate at elevated temperature yields toluene diisocyanate.

Organic carbonates (diesters of carbonic acid) are useful compounds that may be used as solvents, alkylating agents, carbonylation agents, co-polymerization agents, fuel additives, etc. Dimethyl carbonate (DMC) is an important dialkyl carbonate, commonly used as a raw material for the production of diphenyl carbonate (DPC, a diaryl carbonate). There are various processes for commercial production of DMC. In one such commercial process, DMC is produced by transesterification of a cyclic carbonate with methanol in the presence of a homogeneous catalyst. Although patents may disclose use of homogeneous catalysts or heterogeneous catalysts for transesterification of a cyclic carbonate with methanol, there is currently no commercial practice where a heterogeneous or solid catalyst is used for the production of DMC, likely due to the short cycle length of heterogeneous catalysts for such processes. DPC is commonly co-polymerized with a diol, such as bisphenol A, to produce polycarbonates. Polycarbonates are used in various special applications such as memory disks, windshields, engineering plastics, optical materials, etc.

Current techniques for production of diaryl carbonates using a non-phosgene process produces aromatic carbonates, such as DPC, by transesterification of DMC with phenol to produce methyl phenyl carbonate and methanol, followed by disproportionation of the methyl phenyl carbonate to produce DPC and DMC in the presence of homogeneous organometallic catalysts by employing a series of multiple reactive distillation reactors. A preferred homogeneous catalyst is titanium alkoxide. Such processes are disclosed in U.S. Pat. Nos. 4,045,464, 4,554,110, 5,210,268, and 6,093,842, for example. The homogeneous catalysts are recovered from the heaviest portion of the product streams as a solid, which may then be converted to soluble homogeneous catalyst to recycle.

Use of a homogeneous catalyst in the production of DPC often requires separation of the homogeneous catalyst from the product, especially where the catalysts are used at relatively high feed rates. To alleviate this and other shortcomings associated with using homogeneous catalysts for the production of diaryl carbonates, U.S. Pat. Nos. 5,354,923 and 5,565,605, and PCT Application Publication WO03/066569 disclose alternative processes where heterogeneous catalysts are used. For example, U.S. Pat. No. 5,354,923 discloses titanium oxide catalysts in powder form to demonstrate the preparation of EPC, MPC and DPC from DEC or DMC and phenol. U.S. Pat. No. 5,565,605 discloses microporous materials containing Group 4 elements as the catalysts for transesterification and disproportionation. However, solid catalysts in powder form are typically unsuitable or less preferable for large volume commercial production of DPC or methyl phenyl carbonate. WO03/066569 discloses a process for continuously producing DPC in the presence of a heterogeneous catalyst prepared by supporting titanium oxide on silica in a two-step fixed bed process by reacting DMC with phenol.

Z-H Fu and Y. Ono (J. Mol. Catal. A. Chemical, 118 (1997), pp. 293-299) and JP Application No. HEI 07-6682 disclose heterogeneous catalysts for the preparation of diphenyl carbonate by transesterification of DMC with phenol to MPC and disproportionation of MPC to DPC in the presence of $MoO_3$ or $V_2O_5$ supported on an inorganic support such as silica, zirconia, or titania. The transesterification and disproportion are carried out in a reactor-distillation tower consisting of a reactor and distillation tower with removal of the co-products by distillation.

U.S. Patent Application Publication Nos, 2007/0093672 ('672) and 2007/0112214 ('214) (now U.S. Pat. No. 7,288,668) disclose processes for producing various organic carbonates, such as diaryl carbonates, including DPC, in the presence of heterogeneous catalysts. In the '214 publication, the necessary reactions (transesterification and disproportionation) are performed in liquid phase in the presence of a heterogeneous catalyst. Multiple fixed bed reactors for the transesterification and disproportionation reactions are connected to a single distillation column, where light compounds such as ethanol and DEC are removed as an overheads fraction, and the higher boiling compounds, including DPC, are removed as a mixed bottoms fraction. DPC is then recovered from the bottoms fraction.

The '672 publication discloses a process for making diaryl carbonates and dialkyl carbonates by performing the necessary reactions in a dual-phase (vapor and liquid) reaction over various solid catalysts for transesterification and disproportionation. The chemical reactions producing organic carbonates are performed in a series of fixed bed reactors, while performing separation of light co-product in liquid phase to vapor phase in order to shift the unfavorable equilibrium reaction toward the desired product. The process is especially useful for the production of alkyl aryl carbonates such as EPC (ethyl phenyl carbonate) and diaryl carbonates such as DPC (diphenyl carbonate). The process is also useful for the production of dialkyl carbonates such as DEC. A series of fixed bed reactors are connected at different positions on a single distillation column via side-draw streams and return streams. The distillation column also contains separation stages above the last reactor in the series and below the first reactor in the series. The heterogeneous catalysts may be prepared by depositing one or two metal oxides of Ti, Zr, Nb, Hf, Ta, Mo, V, Sb, etc. on porous supports, such as silica gel. The heterogeneous catalysts may also be prepared by grafting one or more organometallic compounds from the elements of Ti, Zr, Nb, Hf. Ta, Mo, V, Sb, etc. on a porous support, which has surface hydroxyl groups or a mixture of hydroxyl and alkoxy groups.

Various other processes for the production of organic carbonates with heterogeneous catalysts are disclosed in U.S. Pat. Nos. 5,231,212, 5,498,743, and 6,930,195.

P. Ball et al. ($C_1$ Mol. Chem. Vol. 1, 1984, pp. 95-108) studied the chemistry of dialkyl carbonate production in the presence of various homogeneous or heterogeneous catalysts. For example, dimethyl carbonate is produced by alcoholysis of urea. Dibutyltin dimethoxide is reported as a particularly effective catalyst. It is reported that heterogeneous catalysts are also effective for the chemistry in the presence of co-catalysts, such as 4-dimethylaminopyridine and $PPh_3$. The reported heterogeneous catalysts are $Al_2O_3$, $Sb_2O_3$, and silica. Fused $SiO_2$ is not a catalyst, but becomes catalytic in the presence of $PPh_3$.

In U.S. Pat. No. 7,074,951, dialkyl carbonate is produced by alcoholysis of urea with an alcohol in the presence of a homogeneous tin complex catalyst in the presence of a high boiling electron donor atom containing solvent, such as triglyme. This patent also demonstrates the capability of producing DMC continuously for about 1500 hours.

EP 1629888 and D. Wang et al. (Fuel Processing Tech. 88, 8, 2007, pp 807-812) disclose that DMC and DEC may be produced in the presence of zinc oxide and zinc oxide supported on silica. These publications are completely silent about the catalyst stability or catalyst cycle length.

Catalyst deactivation during transesterification and disproportionation reactions may be caused by the deposition of heavy polymers on the catalyst surface and pores. The catalyst deactivation rate by polymer deposition increases with the concentration of alkyl aryl carbonate and diaryl carbonate or both in a reaction mixture. Depolymerization of polymers on the heterogeneous catalysts is disclosed in the '672 publication. However, depolymerization may results in only a partial recovery of solid catalyst activity.

U.S. Pat. Nos. 6,768,020 and 6,835,858 disclose processes for making dialkyl carbonates and co-product propylene glycol by reaction of propylene carbonate with DMC, water, or both, in the presence of solid catalyst such as lanthanum oxide and zinc oxide supported on alumina, silica, etc. Catalyst instability is partially solved in U.S. Pat. No. 6,768,020 by depositing a large amount of lanthanum oxide on a support such as alumina and silica.

A favored technique to compensate for catalyst deactivation is the ramping up of the reaction temperature as the catalyst deactivates. This technique, unfortunately, often accelerates deactivation of heterogeneous catalysts.

Long, stable performance of a solid catalyst is generally required for commercial production using a heterogeneous catalyst. Catalyst costs, downtime associated with catalyst replacement, and other factors as known in the art dictate that heterogeneous catalysts have a minimum lifespan, typically grater than 3 months, 6 months, or a year, depending upon the process.

Although heterogeneous catalysis of various transesterification reactions is possible, as described by the various patents and publications above, they do not report longevity or cycle length of the catalyst. It is the experience of the present inventor that such heterogeneous catalysts have undesirably short cycle lengths.

Accordingly, there exists a need for transesterification and/or disproportionation processes using heterogeneous catalysts with improved catalyst performance.

SUMMARY OF THE DISCLOSURE

In one aspect, embodiments disclosed herein relate to an alcoholysis process, the process including: feeding reactants and a trace amount of soluble organometallic compound to a reactor comprising a solid alcoholysis catalyst; wherein the soluble organometallic compound and the solid alcoholysis catalyst each independently comprise a Group II to Group VI element. The solid catalyst and the organometallic compound may include the same Group II to Group VI element in some embodiments.

In another aspect, embodiments disclosed herein relate to a process for the production of dialkyl carbonates, the process including: feeding an alcohol, and an alcoholysis reactant comprising at least one of urea, an organic carbamate, and a cyclic carbonate to a first reaction zone comprising a solid alcoholysis catalyst; feeding a soluble organometallic compound to the first reaction zone, wherein the solid alcoholysis catalyst and the soluble organometallic compound each independently comprise a Group II to Group VI element.

In another aspect, embodiments disclosed herein relate to a process for the production of diaryl carbonate, the process including: feeding an aromatic hydroxy compound and a dialkyl carbonate to a first reaction zone comprising a solid transesterification catalyst; and feeding a soluble organometallic compound to the first reaction zone, wherein the solid transesterification catalyst and the soluble organometallic compound each independently comprise a Group II to Group VI element.

In another aspect, embodiments disclosed herein relate to a process for the production of an alkyl aryl carbonate, the process including: feeding an aromatic hydroxy compound and a dialkyl carbonate to a first reaction zone comprising a solid transesterification catalyst; and feeding a soluble organometallic compound to the first reaction zone, wherein the solid transesterification catalyst and the soluble organometallic compound each independently comprise a Group II to Group VI element.

In another aspect, embodiments disclosed herein relate to a process for the production of biodiesel, the process including: feeding an alcohol and a glyceride to a first reaction zone comprising a solid transesterification catalyst; and feeding a soluble organometallic compound to the first reaction zone, wherein the solid transesterification catalyst and the soluble organometallic compound each independently comprise a Group II to Group VI element.

In another aspect, embodiments disclosed herein relate to a process for the production of an alkyl aryl carbonate, the process including: feeding an aromatic hydroxy compound and a dialkyl carbonate to a first reaction zone comprising a solid transesterification catalyst; and feeding a soluble organometallic compound to the first reaction zone, wherein the solid transesterification catalyst and the soluble organometallic compound each independently comprise a Group II to Group VI element.

In another aspect, embodiments disclosed herein relate to a process for the production of biodiesel, the process including: feeding an alcohol and a glyceride to a first reaction zone comprising a solid transesterification catalyst; and feeding a soluble organometallic compound to the first reaction zone, wherein the solid transesterification catalyst and the soluble organometallic compound each independently comprise a Group II to Group VI element In another aspect, embodiments disclosed herein relate to a process for reactivating a spent solid alcoholysis catalyst, the process including: removing polymeric materials deposited on the catalyst; and re-depositing catalytically active metals on the solid catalyst.

Other aspects and advantages will be apparent from the following description and the appended claims.

BRIEF DESCRIPTION OF DRAWINGS

FIG. 10 is a graphical representation of heterogeneous catalyst activity during production of DPC where the catalyst is grafted simultaneously while performing a transesterification reaction.

DETAILED DESCRIPTION

Figure 1:
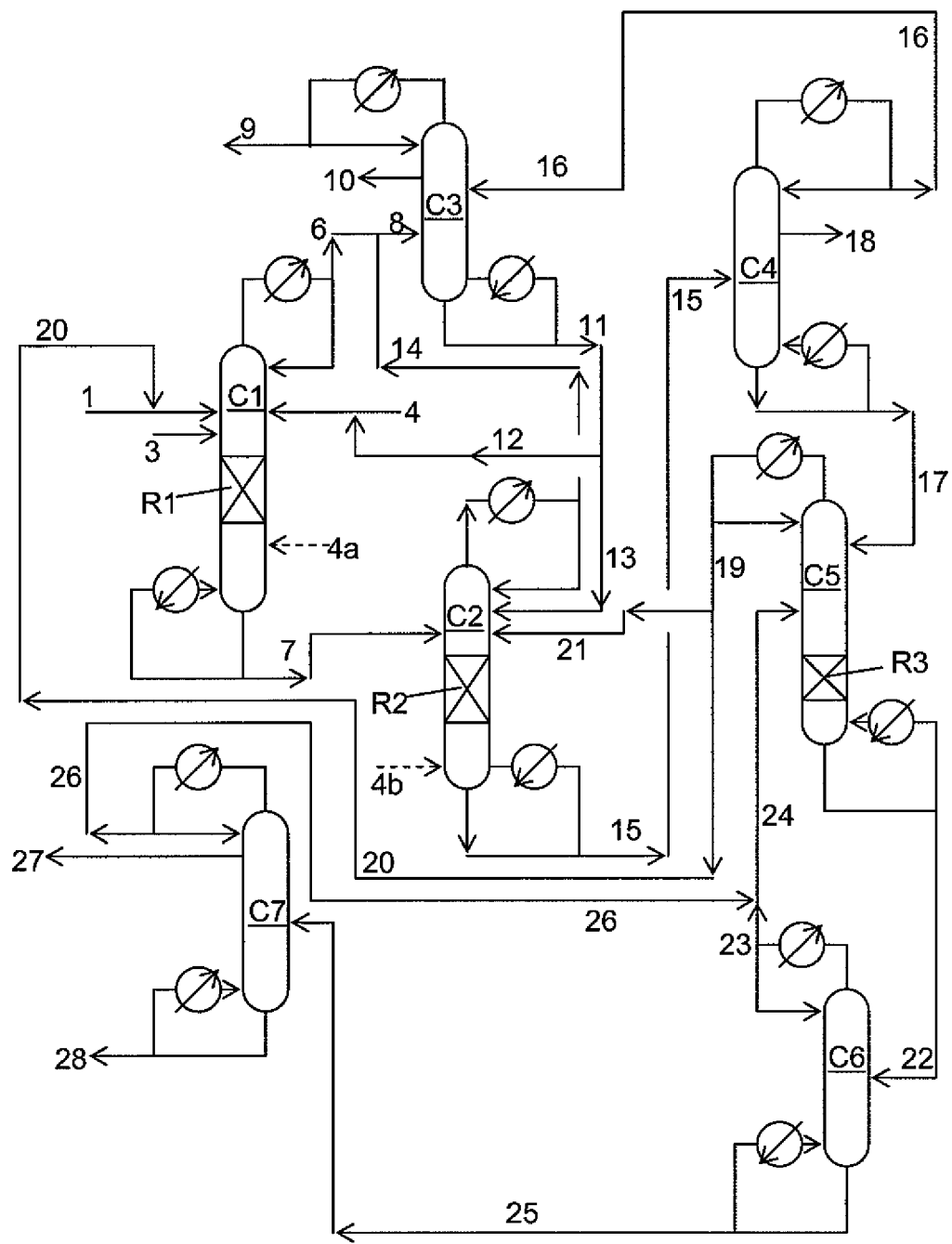
FIG. 1 is a simplified process flow diagram illustrating a process for the production of diaryl carbonates according to embodiments disclosed herein.

In one aspect, embodiments disclosed herein relate to alcoholysis, transesterification, and/or disproportionation processes using solid catalysts. As used herein, alcoholysis is termed to represent various chemical reactions where an organic hydroxyl compound (alcohol) is involved as one of two reactants to produce a product and a co-product. Alcoholysis may be defined as breaking bonds (C—Y) between a carbon atom and a heteroatom Y of molecules by an alcohol molecule (ROH). Alcoholyses are reactions involving carbonyl groups of a molecule and the carbonyl group itself is retained in the product molecule. Therefore, the C atom of the C—Y bond is the carbon atom of carbonyl group of a molecule. Generally alcoholysis is a reversible reaction, and may be represented as follows:

where Y is a heteroatom or a heteroatom of a functional group, and $R^b$ is alkyl, aryl, or a functional group having one or more heteroatoms.

Examples of alcoholysis reactions are the reaction of an alcohol with diesters of carbonic acid, esters of carboxylic acids, urea, and carbamates. Alcoholysis of a dialkyl carbonate (often referred to as transesterification in literature) with phenol produces alkyl aryl carbonate and an alcohol. Alcoholyis of an ester of carboxylic acid with an alcohol exchanges the alkyl group of the ester with the alkyl group of the alcohol molecule and produces a new alcohol molecule. Alcoholysis of urea with an alcohol produces an organic carbamate and ammonia. Alcoholysis of an organic carbamate with an alcohol produces a dialkyl carbonate and ammonia. Specific examples of alcoholysis reactions are the transesterification of DEC with phenol to produce EPC and ethanol, alcoholysis of urea or organic carbamate with an alcohol to produce organic carbamate or dialkyl carbonate and ammonia, transesterification of triglyceride with methanol to produce methyl esters (biodiesel) and glycerin.

Although disproportionation of unsymmetrical carbonic acid diesters and the reaction of a dialkyl carbonate with an organic amine do not involve an alcohol as reactant, it is considered here that these type of reactions are also defined as alcoholysis reactions as well for convenience, because RA groups (R is alkyl or aryl, and A is oxygen atom or nitrogen atom) are involved in the reaction mechanisms at molecular level. Therefore, transesterification and disproportionation are used as synonyms to alcoholysis as necessary for the description of various embodiments. A few of the alcoholysis reactions mentioned above may be represented by the following reactions:

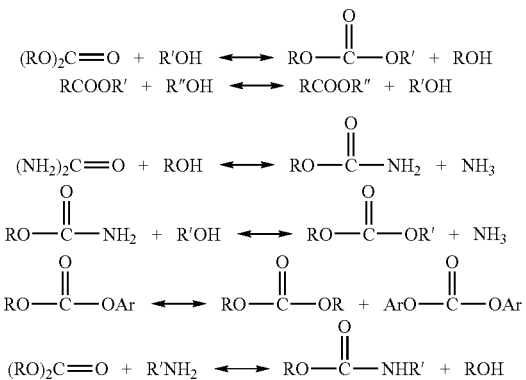

In another aspect, embodiments disclosed herein relate to a novel technique for maintaining catalyst activity for a solid catalyst for an extended cycle time. The cycle time or cycle length of a solid catalyst herein is defined to be the time period over which a solid catalyst can continuously be used without interruption for an intended chemical reaction. For example, if a catalyst requires catalyst regeneration or replacement after continuous use of 6 months, the catalyst cycle length or time is 6 months. According to technique disclosed herein, solid catalysts for alcoholysis processes may retain catalyst activity for an extended cycle time, such as greater than 3 months, 6 months, 1 year, 1.5 years, and 2 years or more, in various embodiments.

During the transesterification of DEC with phenol, deactivation of heterogeneous catalysts (a titanium oxide and a mixed oxide of niobium and titanium oxide immobilized on silica) was observed by the present inventor and reported in Test 4 of the '672 publication. Depolymerization of polymer buildup on the catalyst to improve catalyst activity was also demonstrated in Test 6B of the '672 publication. However, the catalyst regeneration by depolymerization resulted in only a partial recovery of the original catalyst activity. The nature of catalyst deactivation was not fully understood at that time.

It has been surprisingly found that heterogeneous transesterification catalysts, such as heterogeneous catalysts for making DPC, deactivate due to two primary causes: polymer deposition and leaching of catalytically active metal component. Heterogeneous catalysts for making dialkyl carbonate by transesterification of a cyclic carbonate with an alcohol deactivate primarily due to leaching of catalytically active metal components.

During alcoholysis or transesterification reactions over heterogeneous catalysts, the catalytically active metal components on the solid catalysts may leach out of the heterogeneous metal oxide catalysts and organometallic catalysts immobilized on various porous supports into the reaction medium under reaction conditions, resulting in permanent catalyst deactivation. This results in an unacceptably short catalyst life for commercial heterogeneous catalysts that may be used for the continuous production of various organic carbonates. Additionally, as mentioned above, polymer deposition may also affect the performance of a transesterification catalyst. A further mode of catalyst deactivation is poisoning.

A heterogeneous catalyst to be used in a commercial fixed bed reactor must have reasonable longevity for both cycle time and total service time. Absent poisoning, and if there is no or little deposition of polymers on a heterogeneous catalyst, the rate of dissolution of an active metal component from a heterogeneous catalyst may determine the longevity of the catalyst.

Embodiments disclosed herein relate to processes for maintaining a constant or near constant solid catalyst activity for an extended period of time acceptable for continuous production of various organic compounds at a commercial scale. Such processes may be particularly useful for the continuous production of various organic carbonates, such as diaryl carbonates, dialkyl carbonates, and alkyl aryl carbonates, as well as in other transesterification reactions, such as for the production of biodiesel. Selected embodiments disclosed herein relates to processes for maintaining stable catalyst activity for extended period time for large commercial reactors for continuous production of organic carbonates, carboxylic acid esters, or organic carbamates.

The novel technique for maintaining catalyst activity for a solid catalyst for an extended cycle time is that adding a trace amount of soluble active metal components to the liquid feed stream to a solid catalyst-containing reactor may result in a constant or near constant catalyst activity over extended periods of cycle time. It was unexpectedly found that adding a trace amount of soluble active metal components to the liquid feed stream to a solid catalyst-containing reactor may effectively counter balance the metal loss due to the metal leaching out of the solid catalysts, such as by redepositing active metal component on the catalyst, resulting in a constant or near constant catalyst activity over extended periods of cycle time. For example, current efforts by the present inventor indicate that catalyst activity may be maintained for greater than one year by adding a trace amount of soluble active metal compounds to liquid feed stream fed to fixed bed reactors containing a solid catalyst.

The amount of active metal compound required to maintain activity of a solid catalyst may range from less than 1 ppm to about 3000 ppm, depending upon the specific active metal component, the reactants, and other feed components. The amount of active metal in the feed, such as for the production of organic carbonates by transesterification, may be one, two, or more orders of magnitude lower than the concentration of homogeneous catalyst fed for a comparable process using homogeneous catalyst only. In some embodiments, the active metal compound may be fed at a rate of 1 to 400 ppm by weight; 10 to 300 ppm by weight in other embodiments; 15 to 200 ppm by weight in other embodiments; 20 to 150 ppm by weight in other embodiments; and from 30 to 100 ppm by weight in yet other embodiments, based on the total weight of the liquid entering the catalytic reaction zone.

For example, where a solid catalyst includes an active metal, such as a Group II-VI metal, a trace amount of a soluble organometallic compound having the same Group II-VI active metal may be fed to the reactor to maintain the activity of the solid catalyst. As a specific example, where a solid catalyst includes titanium as an active metal, a soluble organometallic compound including titanium may be used.

Where a series of reactors is used, such as a transesterification reactor in series with a disproportionation reactor, a trace amount of soluble organometallic compound may be fed to one or both reactors to maintain catalyst activity in the respective reactors. In some embodiments, by feeding a trace amount of soluble organometallic compound to only the first reactor in a series of reactors, solid catalyst activity may be maintained in each of the reactors. For example, where a transesterification reactor includes a solid mixed oxide catalyst of titanium and niobium, and a disproportionation reactor contains a solid titanium alkoxide grafted on silica, adding a trace amount of soluble organotin compound, such as tin oxide, to the first reactor, the cycle time of both types of solid catalysts may be extended.

The soluble organometallic compound may be recovered and recycled, if desired. In some embodiments, it may not be economical to recover the active metal from the reactor effluent streams for recycle. When recovered, the active metal component in the reactor effluent stream may be recovered from the heavy bottom stream as a solid material and converted to a soluble organometallic compound, which may be recycled to the reactor, such as by reacting the recovered solid material with organic carbonate or a mixture of organic carbonate and alcohol at an elevated temperature. The recovered organometallic compound, for example, may be a metal alkoxide, metal alkoxy alkyl carbonate (metal salt of carbonic acid monoester), or a mixture thereof.

The extended alcoholysis solid catalyst life thus attained may result in commercially viable solid catalyst processes for the production of organic carbonates, among alcoholysis and/or other transesterification processes. Significant savings may be realized due to extended catalysts cycle time and decreased separation requirements (fewer unit operations, resulting in potential capital and operating cost savings).

Polymer deposition on solid catalysts may also cause loss of catalyst activity. In such a case, a deactivated catalyst may be regenerated by depolymerization techniques disclosed herein and in U.S. Patent Application Publication No. 2007/0093672. Depolymerizatoin also can cause metal loss. In the case of following deplolymerization where heterogeneous catalyst does not recover the catalyst activity to an acceptable level of original activity, the heterogeneous catalyst may require metal redeposition, such as by catalyst reactivation techniques disclosed herein.

Whenever there is catalyst deactivation caused by both polymer deposition and metal leach, the catalyst activity may be restored by the catalyst regeneration and reactivation techniques disclosed herein. The catalyst reactivation consists of two steps: depolymerization and surface conditioning in the first step and metal redeposition in the second step. In the first step, the deactivated solid catalyst is subjected to depolymerization to remove polymers on the solid catalyst and then surface conditioning by drying. In the second step, redeposition of active metal component is performed to compensate for metal loss. The reactivation of deactivated catalyst will be discussed in more detail later.

Where catalyst reactivation and/or regeneration are considered, it may be beneficial to have multiple reactors in parallel so as to allow for continuous production during the catalyst reactivation and restoration processes.

As described above, solid alcoholysis, transesterification, and disproportionation processes disclosed herein may include feeding reactants and a trace amount of soluble active metal compounds to a reactor containing a solid catalyst, and contacting the reactants in the presence of the solid catalyst to alcoholyze, transesterify, or disproportionate at least a portion of the reactants. Such alcoholysis, transesterification, or disproportionation processes may include, for example, reactions for the production of dialkyl carbonates, diaryl carbonates, alkyl-aryl carbonates, biodiesels, organic esters, and N-aryl alkyl carbamates, among other reactions.

Although described with respect to alcoholysis, transesterification, and disproportionation reactions in general above, the extension of such processes to the production of organic carbonates is detailed below. U.S. Patent Application Publications 2007/0093672 ('672) and 2007/0112214 ('214), as noted above, disclose processes for the production of organic carbonates using heterogeneous catalysts. Each of these is hereby incorporated by reference.

Organic Carbonate and Organic Carbamate Production

Organic carbonates or organic carbamates may be continuously produced by using a single or multiple reactor systems in the presence of a solid catalyst or two different solid catalysts. The solid catalyst or catalysts require adding a trace amount of soluble active metal compound into the feed stream of the reactor to obtain an extended catalyst cycle time. Solid catalysts may be any physical shape, and may include various organometallic compounds immobilized on porous supports, and/or oxides containing an element or multiple elements of Group II, III, IV, V and VI supported on a suitable porous support. The catalysts may be either acid catalysts or base catalysts. The total amount of catalytically active metal or metal components on a supported catalyst may range from about 0.02 wt % to about 20 wt % in some embodiments; from about 0.05 wt % to about 10 wt % in other embodiments.

The reactors used in embodiments disclosed herein may include any physical devices or a combination of two or more devices. The reactors may have various internal devices for vapor-liquid separation and vapor/liquid traffic.

By adding a trace amount of soluble active metal compound to a feed stream, stable catalyst activity may be maintained for surprisingly long cycle times. For example, addition of trace amounts of a soluble active metal compound into streams fed to a fixed bed reactor to produce mixtures of ethyl phenyl carbonate and diphenyl carbonate may results in a cycle time of more than 14 months on stream time. Such stable catalyst performance may result in higher productivity of a desired product. In embodiments having a series of reactors, a trace amount of an active metal component may be added only to the feed stream to the first reactor. For a parallel multiple reactor system, a trace amount of an active metal component may be added to all reactors.

The active metal components may include a compound or a mixture of compounds containing one or more metals of Group II, III, IV, V and VI of the Periodic Table. Examples of active metals include Mg, Ca, Zn, La, Ac, Ti, Zr, Hf, V, Nb, Ta, Cr, Nb, W, Sn, Pb, Sb, etc. The active metal compound should be soluble in the reaction mixture or, at least, form an emulsion. The amounts of trace metal in the feed stream may be sufficiently low so as to be economically unnecessary to recover metal from process stream to recycle, although one may choose to do so.

If necessary, a deactivated catalyst in a reactor may be reactivated in situ in a relatively short time, so as to be ready to replace another reactor in service or to restart service. Therefore, embodiments of the processes disclosed herein may require a spare reactor, depending on the cycle length of the catalyst and other factors.

Processes disclosed herein may be particularly useful for the continuous production of diaryl carbonates, such as diphenyl carbonate, alkyl aryl carbonates, such as ethyl phenyl carbonate, or dialkyl carbonates, such as diethyl carbonate or dimethyl carbonate. The reaction for producing diary carbonate may be performed in a plurality of reaction zones, such as a first and a second reaction zone. The first reaction zone serves to perform primarily transesterification of a dialkyl carbonate with an aromatic alcohol to produce an alkyl aryl carbonate, although a small amount of diaryl carbonate may also be produced. The second reaction zone serves to perform disproportionation of an alkyl aryl carbonate to produce diaryl carbonate and dialkyl carbonate. The presence of a solid h catalyst in the second reaction zone is not necessary, although one may choose to use a solid catalyst.

Dialkyl carbonates, such as DMC or DEC, may be produced by performing transesterification of a cyclic carbonate, such as propylene carbonate or ethylene carbonate, with methanol or ethanol in a similar manner. The reactions producing diaryl carbonate and dialkyl carbonate are performed in a multiple reactor system with material separation units to recover products from reaction mixtures. Unreacted reactants and intermediates may be recovered for recycle or finished by performing a second disproportionation or a second transesterification. Unreacted phenol in the liquid reaction mixture from transesterification zone may be separated either prior to performing disproportionation of alkyl phenyl carbonate or after performing disproportionation. Additionally, there are various options for purging the by-product alkyl phenyl ether from the reaction system. Proper arrangement of reactors with material separation units is within the knowledge of those of ordinary skill in the art.

The reactions are preferably carried out as a mixed phase system, where the reactants and products are liquid and vapor, to shift the equilibrium to the desired direction. Alternatively, one may perform a reaction in liquid phase, such as where there is no or little advantage in shifting equilibrium reaction due to higher boiling points of the reaction products than a preferred range of temperatures for performing the reaction.

Embodiments disclosed herein may also be useful in producing organic carbonates, such as ethyl phenyl carbonate, methyl phenyl carbonate, and diphenyl carbonate, by performing transesterification of dialkyl carbonates, such as diethyl carbonate or dimethyl carbonate, with phenol, and disproportionation of an alkyl aryl carbonate, such as ethyl phenyl carbonate or methyl phenyl carbonate, to produce diphenyl carbonate.

Embodiments disclosed herein may also be useful in producing dialkyl carbonate, such as dimethyl carbonate or diethyl carbonate, by transesterification of a cyclic carbonate with an alcohol. In other embodiments for the production of dialkyl carbonates, dialkyl carbonate may be produced by alcoholysis of urea with an alcohol in the presence of a solid catalyst. For example, in U.S. Pat. No. 7,074,951, dialkyl carbonate is produced by using a homogeneous organotin complex catalyst in the presence of a high boiling electron donor atom-containing solvent; such a process may be performed over solid catalysts according to embodiments disclosed herein. Various organic carbamates, such as an N-aryl alkyl carbamate, may also be advantageously produced by reacting a dialkyl carbonate with an aromatic amine in the presence of a solid catalyst according to embodiments disclosed herein.

Any type of reactors may be used to carry out the reactions described herein. The examples of reactors suitable for carrying out the reactions involving organic carbonate or organic carbamates reactions may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors.

Multiple reactor systems useful in embodiments disclosed herein may include a series of multiple reactors or multiple reactors in parallel for the first reaction zone. If a product is produced from reactants via an intermediate product, such as an alkyl aryl carbonate, the first reaction zone may serve to primarily produce the intermediate although a minor amount of final reaction product may simultaneously be produced in the first reaction zone.

The process stream from the first reaction zone, after stripping off any alcohol and dialkyl carbonate, enters to the second reaction zone, where diaryl carbonate is produced along with co-product dialkyl carbonate. While stripping lighter reaction product from the catalytic reaction zone, the transesterification may be simultaneously performed, shifting the equilibrium reaction toward the forward reaction.

The reactions producing organic carbonates or organic carbamates are typically performed at a temperature in the range from about 104° C. to about 260° C. (about 220° F. to about 500° F.) in some embodiments; from 121° C. to about 232° C. (about 250° F. to about 450° F.) in other embodiments. The pressure for a reaction depends on boiling points of the reactants and products, the type of reactor to be used, and whether liquid or dual phase (vapor/liquid) exists in the reaction zone. In general, reactor pressures may be in the range from sub-atmospheric pressure to about 22 bar (about 319 psia) in some embodiments; and from about 0.005 bar to about 17 bar (0.1 psia to about 250 psia) in other embodiments. In a class of embodiments, reactions may be performed using a suitable solvent which does not interfere with separation of reaction products.

In selected embodiments, embodiments disclosed herein are particularly useful for the continuous production of diaryl carbonates from a dialkyl carbonate and an aromatic hydroxy compound, such as the production of diphenyl carbonate (DPC) from a dialkyl carbonate and phenol. One route for producing DPC is the reaction of diethyl carbonate (DEC) with phenol in the presence of one or more solid catalysts. The advantages of producing DPC by using DEC may include energy saving and material saving for the construction of a plant because separation of materials from an azeotrope is not necessary. All materials need energy to produce them. Thus, saving construction materials, and energy, is considered to be "green." In contrast, the current commercial non-phosgene process of producing DPC uses DMC as one of raw materials. DMC and methanol have to be separated from an azeotrope-forming process stream by solvent extractive distillation. Operating extractive distillation units is energy intensive. Although production of DPC via DMC is possible, use of DEC may be preferred due to the energy and material savings.

Embodiments disclosed herein may also be useful for producing dialkyl carbonates by transesterification of a cyclic carbonate with an alcohol, such as ethanol or methanol.

Producing DPC from a dialkyl carbonate and phenol involves two reaction steps; transesterification in a first reaction zone, followed by disproportionation in a second reaction zone. The reactions may be illustrated as follows:

Reaction (2) involves disproportionation of alkyl phenyl carbonate to produce diphenyl carbonate and dialkyl carbonate. Both reaction steps are equilibrium reactions. However, the disproportionation is thermodynamically much more favorable than the transesterification. The transesterification is primarily performed in the first reaction zone, which may include a single reactor or a multiple reactor system. The disproportionation reaction may then be primarily performed in a second reaction zone.

Producing a dialkyl carbonate by transesterification of a cyclic carbonate with an alcohol is also two-step equilibrium reaction. Both acidic and basic catalysts may be used for transesterification of a cyclic carbonate with an alcohol.

According to embodiments disclosed herein, to obtain prolonged catalyst cycle length, a trace amount of a soluble metal compound is added to the reactor feed stream. For transesterification of cyclic carbonate with an alcohol to produce a dialkyl carbonate and a diol, either a solid base or acid catalyst may be used. One may also perform the transesterification by substituting a portion of alcohol with water. Alternatively transesterification may be performed in the first step, followed by the reaction of unconverted cyclic carbonate and intermediate with a water-alcohol mixture to produce a glycol as a major reaction product in the second step. Addition of water substantially increases the conversion of cyclic carbonate or productivity of a diol. However, the water advantage is only realized in a reduced yield of dialkyl carbonate.

Catalysts Useful for Organic Carbonate and Organic Carbamate Production

As described above, catalysts useful for organic carbonate and organic carbamate production may include supported solid catalysts having one or more active metals from Groups II, III, IV, V and VI of the Periodic Table. One type of catalyst useful in embodiments disclosed herein includes an organometallic compound or multiple organometallic compounds of the above elements immobilized on a porous support. Porous supports useful in embodiments disclosed herein may include surface functional groups such as hydroxyl groups, alkoxy groups, mixtures of hydroxyl and alkoxy groups, chlorine, etc. Examples of supports may include silica, silica-alumina, titanium oxide, zirconium oxide, or zeolitic materials, such as MCM-41, MCM-48, SBA-15, etc., and composite materials including a binder and a zeolite.

Alternative supports may include carbon and/or carbonaceous materials, Carbon and carbonaceous supports may

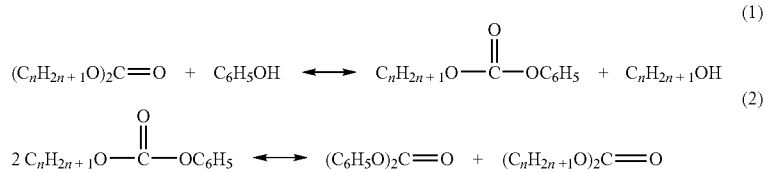

(1)

$(C_nH_{2n+1}O)_2C=O + C_6H_5OH \longleftrightarrow C_nH_{2n+1}O-\overset{O}{\underset{\parallel}{C}}-OC_6H_5 + C_nH_{2n+1}OH$ (2)

$2\,C_nH_{2n+1}O-\overset{O}{\underset{\parallel}{C}}-OC_6H_5 \longleftrightarrow (C_6H_5O)_2C=O + (C_nH_{2n+1}O)_2C=O$ where the net reaction may be illustrated as:

(3)

$(C_nH_{2n+1}O)_2C=O + 2\,C_6H_5OH \longleftrightarrow (C_6H_5O)_2C=O + 2\,C_nH_{2n+1}OH$ Reaction (1) is the transesterification of a dialkyl carbonate with phenol to produce alkyl phenyl carbonate and alcohol.

have surface functional groups, such as hydroxyl, carbonyl, or both, to immobilize organometallic compounds on the surface, as discussed earlier. To prepare supported metal oxide, hydroxide, or oxyhydroxide catalysts, the surface functional groups may not be necessary, although may be useful in some embodiments. Carbonaceous supports may be prepared by controlled thermal dehydration of carbohydrates, such as wood, coconut shells, starches, cellulose, a mixture of starch and cellulose, sugar, methyl cellulose, and the like, at elevated temperatures. Carbonaceous supports may be either unsupported or supported. To prepare supported carbonaceous material, carbohydrates may be deposited on a suitable porous support followed by controlled thermal dehydration at an elevated temperature, such as a temperature in the range from about 250° C. to 1000° C., in an inert atmosphere or an atmosphere composed of an inert gas and a small amount of oxygen, steam or a mixture thereof. Supports for carbonaceous materials may include any inorganic materials, such as alumina, titania, silica, zirconia, synthetic and natural clays, including silica-aluminas, and other supports as known in the art.

The supports, in some embodiments, may require removal of condensed water in the pores prior to contacting organometallic compounds with the supports to perform immobilization. Condensed water on a support is defined here as water content that may be removed by drying the support at a temperature in the range from about 50° C. to about 400° C. in dry gas flow or under a vacuum, depending upon chemical composition of the support. Solid catalysts used herein may be prepared by immobilizing one or two organometallic compounds having active catalyst sites on a porous solid support. Mobilization may be performed, for example, by using techniques such as grafting, tethering, adsorption, etc. For example, catalyst preparation techniques for organometallic compounds such as titanium alkoxides on porous supports has been disclosed in the '672 publication.

A second type of catalyst useful in embodiments disclosed herein includes a metal oxide, mixed metal oxides, or oxyhydroxides deposited on a porous support. Examples of this type of catalyst are also disclosed in the '672 publication.

Supports may be in the form of pellets, extrudates, spheres, granules, honey comb, and the like, in sizes ranging from about 1 mm to about 5 mm for various fixed bed reactors. Supports in powder or microsphere forms may also be used to for the preparation of catalysts to be used for slurry or stirred reactor.

Preparation of the second type of catalysts described above may not require a support having surface hydroxyl group. However, surface functional group-containing supports, such as silica, carbonaceous material, alumina, etc., may also be used to prepare metal hydroxide/oxide catalyst by grafting metal alkoxides, such as titanium alkoxide, on a silica, followed by steaming or hydrolyzing and/or drying at a temperature from about 90° C. to about 500° C.

Another method for preparing metal oxide or oxyhydroxide catalysts includes depositing a salt of a desired element or a mixture of salts of two different elements on a support followed by calcining at a temperature from 300° C. to 1000° C. to decompose the salts to metal oxides.

Under process conditions, transesterification and disproportionation in a catalytic reaction zone may occur simultaneously as the concentration of an alkyl aryl carbonate in the reaction medium increases. The two causes for the catalyst deactivation discussed above, leaching and polymer deposition, also occur simultaneously under reaction condition. While polymer deposition does not cause permanent damage to a catalyst, the active metal component leaching out of heterogeneous catalysts under reaction conditions does result in permanent damage to the catalyst. At low conversion levels for the transesterification or at low concentrations of alkyl aryl and diaryl carbonates, catalyst deactivation is mostly caused by dissolution of active metal catalyst components from a solid catalyst into the reaction medium. In other words, the cause of permanent catalyst deactivation under all reaction conditions is metal leaching.

As the transesterification conversion increases, polymer deposition on the catalyst causes even faster catalyst deactivation. Polymer deposition is primarily the result of undesired side reactions of alkyl aryl and diaryl carbonates (and potentially trace amounts of poly hydroxyl aromatic compound impurities in a phenol feed and produced by undesired side-reactions in minute quantities). Therefore, to continuously produce diphenyl carbonate from phenol and a dialkyl carbonate, such as diethyl carbonate or dimethyl carbonate, in the presence of heterogeneous catalysts, it may be required to address catalyst deactivations caused by both (1) polymer deposition and (2) dissolution/leaching of active metal catalyst components. Polymer deposition may be addressed by controlling conversion, concentration of aromatic carbonates, or both in the catalytic reaction zone, as mentioned above, and via catalyst reactivation, such as disclosed in the '672 publication. Leaching is addressed via adding a trace amount of soluble organometallic compound, as described above.

Immobilizing (e.g., grafting, tethering, adsorption, etc.) organometallic compounds on a support such as silica or carbonaceous material for alcoholysis and/or transesterification of a dialkyl carbonate with phenol may be carried out in a single reaction zone step or multiple reaction zone steps. Examples of the organometallic compounds disclosed include metal alkoxides, alkoxy chlorides, carboxylates, carbonates, etc., of Group II, III, IV, V and VI elements. Examples of active metals include Mg, Ca, Zn, La, Ac, Ti, Zr, Hf, V, Nb, Ta, Cr, Mo, W, Sn, Pb, Sb, etc. In various embodiments, tin alkoxides, alkyl tin alkoxides, alkyl tin oxides, alkyl tin hydroxides, dialkyl tin dichloride, alkyl tin trichloride and a mixtures of these species as well as metal oxyalkoxides [$(RO)_n MO$] and metal alkoxy hydroxide [$(RO)_n M(OH)_x$] or oligomers of these oxyalkoxides and alkoxy hydroxide are included, where M is a Group IV, V or VI element, n=2, 3 or 4, x=0, 1, 2 or 3, and n+x=4, 5 or 6. In selected embodiments, the organometallic compound may be one or more of a titanium alkoxide or phenoxide, alkyl aryl titanate, or titanium salt of a carbonic acid monoester. It should be understood that metal alkoxides include monomers, various oligomers, or a mixture of various monomer and oligomer species, depending on the carbon chain length and structure of the alkyl group of an alkoxide or aryloxide [see, for example, Coordin. Chem. Rev., 2 (1967) 299-318; J. Chem. Soc., 3977 (1955)].

As described herein, alkoxides of a transition metal include all the species of monomer and various oligomers. For example, while titanium ethoxide [$Ti(OEt)_4$] exists mostly as trimer in boiling ethanol or benzene, sterically hindered titanium alkoxides, such as titanium isoproxide, are monomeric in boiling hydrocarbon solutions. For example, titanium isopropoxide is believed to exist mostly as monomer in a boiling toluene solution.

Porous supports used in various embodiments disclosed herein may have surface hydroxyl groups, alkoxy groups, or both. To prepare the porous support, porous metal oxide supports, such as titanium oxide, zirconium oxide, molybdenum oxide, and vanadium oxide, may be treated with a stream containing one or more of an alcohol, an organic carbonate, such as dimethyl carbonate, diethyl carbonate, etc., at a temperature in the range from about 130° C. to about 400° C. in some embodiments, from 150° C. to 350° C. in other embodiments, in a vapor phase, liquid phase, or a vapor-liquid system. The stream may contain water from 0 wt % to about 20 wt % in some embodiments; from 0 wt % to about 10 wt % in other embodiments; and from about 0.005 wt % to about 5 wt % in yet other embodiments. As water has little solubility in DMC and DEC, the stream may contain appropriate amounts of methanol and/or ethanol as solvent for water. Commercially available silica gel or silica, having surface hydroxyl groups, may be used in some embodiments. Optionally one may perform treatment of silica with liquid water, steam, or a mixture thereof at a temperature from about 80° C. to about 500° C. followed by drying at a temperature from about 70° to about 800° C. in some embodiments, and from about 80° C. to about 500° C. in other embodiments.

Silooxane and siloxane compounds of the transition metals may also be used to prepare solid catalysts immobilized on porous supports or metal oxide catalysts as described above. Examples of silooxane and siloxane compounds are $(RO)_{n-x}M[-O-Si(O-R)_3]_x$, $M(O-SiR_3)_n$, $(R_3SiO)_{n-2}MO$, etc., where each R is independently an alkyl or aryl group, n=3, 4, or 5, x=1 or 2, n+x=4, 5 or 6, and M is a transition metal of Group IV, V or VI as described above. Other silicon-metal compounds are within the scope of embodiments disclosed herein, as long as the immobilization results in catalytic activity of the solid catalysts. Silooxane and siloxane compounds of the transition metals may also be used as soluble organometallic compounds in the process arrangements disclosed in the '672 and the '214 publications, as well as reactive distillation column reactors. Various oligomeric and polymeric heterosilooxane or heterosiloxanes of the transition metals may also be used, may be used to prepare immobilized solid catalysts, or may be used as soluble organometallic compounds in various embodiments. As described above, disproportionation of EPC or MPC to DPC and DEC or DMC may be performed in the absence of a solid catalyst in the second reaction zone, and useful active catalytic species include silooxane or siloxane compounds of a transition metal such as Ti.

The metal oxides and alkoxides of siloxanes may include various oligomers. Various oligomers may be found in the publications by Bradely [D. C. Bradley, Coordin. Chem. Rev., 2 (1967) p.p. 299-318); J. Chem. Soc., (1955) 3977]. One may choose to add a trace amount of one of these compounds into the feed to the reaction zone to obtain stable catalyst activity.

When carrying out disproportionation of alkyl aryl carbonates to produce diaryl carbonate and dialkyl carbonate in the second reaction zone in the presence of a homogeneous catalyst, the homogeneous catalyst may be a mixture of alkyl aryl titanates, titanium salts of carbonic acid monoesters, and siloxane compounds of titanium discussed above. It is understood that the homogeneous catalysts may originate from the solid catalysts and soluble catalysts used in the transesterification reaction zone.

Since various organo-metallic compounds disclosed herein are sensitive to moisture in the feed stream, it is important to control the water content in the feed stream to the reaction zone. In some embodiments, the moisture content of the feed stream is less than about 700 ppm; less than about 600 ppm in other embodiments.

The solid metal alkoxide catalyst immobilized on a support may be prepared by in situ techniques inside the reactor or may be prepared outside reactor. For in situ preparation, a predetermined amount of a suitable support is placed in a reactor, followed by drying at a proper temperature to remove at least a portion of any condensed water. The support is then contacted with a solution containing soluble metal alkoxide or mixed metal alkoxides of a transition metal or metals at a temperature in the range from about ambient to about 260° C. (500° F.) in some embodiments, and from about 37° C. to about 204° C. (about 100° F. to about 400° F.) in other embodiments. Contacting may be performed for a period of time from about 5 minutes to about 24 hours in some embodiments, and from about 15 minutes to about 15 hours in other embodiments, and may depend on the temperature and the concentration of active metal component in solution. After draining out excess metal alkoxide solution from the reactor, the catalyst in the reactor may be washed with a solvent (usually the same solvent used to prepare the metal alkoxide solution) prior to use in disproportionation or transesterification reactions. The solvent may be an alcohol, an ether, a hydrocarbon, a mixture of hydrocarbons and an alcohol, or a mixture of a dialkyl carbonate and phenol or an alcohol, or mixtures of all of these.

Alternatively, metal oxide, mixed-metal oxide, or metal hydroxide catalysts, where the metal is one or more from Groups II, III, IV, V and VI of the Periodic Table, may also be used according to embodiments disclosed herein. Some metal oxide catalysts are known in the art. For example, according to P. Iengo et al., Appl Catal. A: General 178 (1999) 97-109, titanium oxide catalysts supported on silica may be prepared by grafting titanium isoperoxide and then steaming/calcination, the supported catalyst having a strongly modified original silica surface resulting in a catalyst different from those obtained by impregnation and co-precipitation.

To prepare supported metal or mixed metal hydroxide or oxyhydroxide catalysts, one may hydrolyze the grafted metal alkoxide catalysts, as described above, followed by drying at a temperature in the range from about 50° C. to about 110° C. In some embodiments, drying may not be necessary.

Preconditioning of unsupported metal oxide catalysts may be performed prior to performing reactions producing organic carbonates. The preconditioning is performed by contacting a porous metal oxide catalysts, such as titanium oxide, zirconium oxide, molybdenum oxide, or vanadium oxide, with a stream containing an organic carbonate, such as dimethyl carbonate, diethyl carbonate, etc., at a temperature in the range from about 125° C. to about 450° C. in some embodiments, and from about 150° C. to about 350° C. in other embodiments, where the organic carbonate may be in the vapor phase, liquid phase, or a mixed phase. Preconditioning may be performed for a period from about 2 minutes to about 50 hours in some embodiments, and from about 4 minutes to about 24 hours in other embodiments. The stream containing organic carbonate may include water and an alcohol, where the water may be present from greater than 0 wt % to about 10 wt % in some embodiments, and from about 0.005 wt % to about 4 wt % in other embodiments. Selectivity of the catalyst may be improved by the preconditioning. After preconditioning, the metal oxide catalysts may be dried at a temperature from about 80° C. to about 300° C. in an inert gas flow for a period of time from about 2 minutes to about 6 hours.

Two types of mixed metal oxide catalysts may be used for the transesterification of a cyclic carbonate with an alcohol. The first type of mixed metal oxide catalysts may include one or more elements from Groups III, IV, V, and VI of the Periodic Table supported on a support. The second type of the mixed oxides includes a solid base catalyst that contains one or two elements from Group II of the Periodic Table and lanthanides or actinides on a support. Optionally, one may use a quaternary ammonium hydroxide grafted or tethered on a silica support. The oxide catalysts are usually supported on alumina or silica or prepared in the form of a mixed oxide or a solid solution. The elements useful for the second type of solid catalysts may include Mg, Ca, Zn, La, etc.

Active metal components of the second type catalysts may also leach out under transesterification reaction conditions, resulting in catalyst deactivation. In fact, it has been found that silica supports may also leach out, only at a much slower rate than Group II active metal components. Since alkali metal impurities on a silica support may increase the dissolution of silica into the reaction medium, minimal alkali metal impurites in silica support is highly desirable. By adding trace amount of soluble organometallic compounds into a feed stream, the cycle length of a solid catalyst may be extended for fixed bed reactors. Examples of such soluble compounds include zinc 2-methoxyethoxide, calcium 2-methoxyethoxide, zinc 2-methoxypropoxide, zinc ethoxide, zinc alkoxy alkyl carbonate, calcium 2-methoxyproxide, calcium ethoxide, calcium alkoxy alkyl carbonate, magnesium 2-methoxyethoxide, magnesium 2-methoxyproxide, magnesium ethoxide, magnesium butoxide, magnesium alkoxy alkyl carbonate, lanthanum alkoxide, lanthanum alkoxy alkyl carbonate, and Mg, Ca, and Zn propylene glycerides, among others. A mixture of these may also be used.

Soluble compounds of Ca, Mg, Zn, and La may be obtained by reacting oxides or hydroxides of these metals with an alcohol, an organic carbonate, or a mixture of an organic carbonate and an alcohol at temperature from about 105° C. (221° F.) to about 260° C. (500° F.) in some embodiments, from about 149° C. (300° F.) to about 227° C. (440° F.) in other embodiments, in liquid phase or mixed phase (liquid and vapor) system. Solutions prepared in this manner may be useful for adding trace amounts of these metals into the feed stream to a reactor so as to obtain long cycle time. Total amount of active metal or metal components on a solid metal alkoxide, metal hydroxide, or metal oxide catalyst may range from about 0.02 wt % to about 20 wt %, preferably from about 0.05 wt % to about 12 wt %.

Improved Catalyst Cycle Length and Service Life

The solid catalysts disclosed herein may have long cycle lengths and may be able to undergo catalyst regeneration and reactivation may times, resulting in long catalyst service times. The techniques of extending catalyst cycle length and catalyst reactivation disclosed herein make catalysts typically interesting for laboratory purposes useful in commercial production of various organic carbonates. It is surmised that whether starting with supported metal oxide catalysts or metal alkoxide catalysts immobilized on silica, at steady state, the active catalysts are organometallic compound species immobilized on silica. To illustrate the benefit of adding a trace amount of active metals in the feed, various experiments were performed, and will be described in more detail below. Briefly, in one experiment, a titanium oxide catalyst (6 wt % Ti) supported on a silica gel, was regenerated by depolymerization after serving about 350 hours, and recovered less than half of its original activity of the transesterification of diethyl carbonate with phenol. It was found that more than half of the Ti had been leached out of the catalyst into the reaction medium during the service time. In another experiment, a titanium butoxide catalyst (4 wt % Ti) grafted on a silica gel lost over 90% Ti after serving only 171 hours for the disproportionation of ethyl phenyl carbonate. After serving 173 hours, another titanium oxide catalyst (5.7 wt %) supported on silica gel, used for transesterification of propylene carbonate with ethanol to produce diethyl carbonate and propylene glycol, lost 35% of the Ti on the catalyst. From these findings, it is very clear that both supported titanium oxide catalyst and grafted titanium alkoxide catalyst are unsuitable for commercial reactors for the continuous production of organic carbonates, such as dialkyl carbonate, alkyl phenyl carbonate, and diary carbonate, due to permanent catalyst deactivation in short service time. It appears that organic carbonates and/or reaction mixtures are reactive enough to cause slow formation of soluble organometallic compounds in the reaction medium by reacting with solid catalysts.

It has also been documented that DMC and DEC vapor streams may react with silica or titanium oxide to form tetra-alkyl orthosilica and titanium tetra-alkoxide at a temperature higher than about 350° C. The reactions of DMC and DEC with silica become easier in the presence of a catalytic amount of alkali metal on silica. Therefore, it was necessary to discover a technique for simple catalyst reactivation and a method to maintain constant surface concentrations of active metal components on the catalyst for a sufficiently long cycle time to be acceptable for commercial reactors.

Catalyst regeneration via depolymerization and metal redeposition addresses problems associated with polymer deposition. However, regeneration via depolymerization fails to address the problems associated with continuous leaching of active metals from heterogeneous catalysts under reaction conditions. The continuous loss of active metal from heterogeneous catalysts must be addressed to obtain long catalyst cycle length suitable for commercial scale reactors. It was discovered that the effect of metal leaching from heterogeneous catalysts could be neutralized by adding trace amounts of active metal compounds into the feed stream(s) to the first reactor in the case of a series of multiple reactor system. By adding a trace amount of soluble active metal compound, metal leaching and redeposition are balanced or nearly balanced, effectively maintaining a constant number of active sites on the solid catalysts, resulting in a steady catalyst activity for a long catalyst cycle time. It is understood that the soluble metal component leaching out of the solid catalyst in the first reactor is a mixture of various metal compound species. The metal compound species in the mixture are not necessarily identical to the metal compound species coming into the first reactor. The metal leach and redeposition in the second reactor is also balanced in similar fashion. For parallel multiple reactor systems, the addition of a trace amount of active metal compound to all feed streams to the first primary reaction zone may be required. Therefore, catalyst reactivation (in situ depolymerization/surface conditioning and metal redeposition) and adding a trace amount of active metal compound followed by metal redeposition may address both metal leaching and polymer deposition. Catalyst reactivation may be performed in two steps: (1) depolymerization/conditioning of the catalyst surface, and (2) redeposition of active metal components. The catalyst surface conditioning is necessary to immobilize titanium alkoxide on silica support surface. A fresh immobilized catalyst or a reactivated catalyst loses catalytic activity continuously, resulting in unacceptably short cycle time that is unsuitable for large commercial reactors. The loss of an original catalyst activity to about half activity for transesterification of a dialkyl carbonate with phenol takes about 80-150 hours-on-stream time, which is clearly inadequate for continuous operation of commercial reactor. By adding trace amounts of soluble active metal compound and performing the two-step reactivation, it is now possible to extend catalyst cycle length and carry out catalyst reactivation multiple times for the continuous production of various organic carbonates.

Depolymerization of a deactivated catalyst may be performed by contacting the catalyst with a stream containing a hydroxy compound or a mixture of hydroxy compounds in situ at a temperature from 102° C. (215° F.) to 316° C. (600° F.) in some embodiments, from 104° C. (220° F.) to 232° C. (450° F.) in other embodiments, for a period of time from about 10 minutes to about 50 hours in some embodiments, and from 30 minutes to 15 hours in other embodiments. The depolymerization may be carried out in vapor phase, in liquid phase, a mixed phase, or in liquid phase followed by in vapor phase, or in reverse order. Depolymerization products may include phenol, alcohol, carbon dioxide, multihydroxy benzene, dialkyl carbonate, alkyl phenyl carbonate, and heavier compounds.

Examples of hydroxy compounds to be used for depolymerization on a catalyst are alcohols (preferably methanol or ethanol), water, or a mixture thereof. If dimethyl carbonate is used as one of the feedstocks to produce methyl phenyl carbonate and diphenyl carbonate, methanol or a mixture of water and methanol may be used for the depolymerization. If diethyl carbonate is used as one of the feedstocks, ethanol or a mixture of water and ethanol may be used for the depolymerization. One may also use a mixture of methanol and ethanol. When water is used in the depolymerization, the water content in the mixture may be in the range from greater than zero wt % to less than 100 wt % in some embodiments; from 10 ppm by weight to 15 wt % in other embodiments; and from 15 ppm by weight to 5 wt % in yet other embodiments. An azeotropic mixture of water (4 wt %) and ethanol is very effective for the depolymerization where diethyl carbonate is used as one of the feed stocks. In some embodiments, a mixture of water and alcohol may be preferred over either water or alcohol alone, allowing for the conditioning of the catalyst surface for the redeposition of active metal component. Additionally, a mixture of water and an alcohol may be more effective for the depolymerization and surface conditioning than alcohol or water alone.

One may also use a solvent in the depolymerization. Useful solvents may include benzene, toluene, xylenes, pentane, hexane, octane, decane, tetrahydrofuran, ether, etc. or any mixtures of such solvents. The concentration of solvent in a depolymerization mixture may range from 0 wt % to about 90 wt %.

Depolymerized catalyst may be dried to remove excess water on the catalyst and to control the population of surface hydroxyl groups prior to redeposition of active metal component on the catalyst. The in situ drying may be carried out at a temperature from about 49° C. (120° F.) to about 427° C. (800° F.) in some embodiments, from 65° C. (150° F.) to 316° C. (600° F.) in other embodiments, in an inert gas flow, for a period of from about 15 minutes to 40 hours under ambient pressure or a subatmospheric pressure, prior to performing redeposition of active catalyst component. Improper catalyst surface preconditioning may result in only partial recovery of catalyst activity. The depolymerization technique disclosed herein may be used in any process for the production of aromatic carbonates or any reaction where organic carbonates are involved as reactants, products, or both.

The depolymerization technique disclosed may also be useful for reactions producing organic carbonates in the presence of a homogeneous catalyst. For the regeneration of a homogeneous catalyst system, an alcohol solution must be fairly dry so that water content may not exceed about 0.01 wt %, Therefore, the catalyst regeneration technique disclosed herein may be useful for any process for producing organic carbonates.

The effluent stream from a reactor during depolymerization may contain a trace amount of active metal component, depending on how the depolymerization is performed. This stream may also contain phenol, DEC, small amounts of phenetole, EPC and heavier compounds as major depolymerization products. If desired, one may attempt to recover the useful components such as phenol, ethanol, alkyl phenyl carbonate and DEC from this steam.

The redeposition of active metal component on a depolymerized and surface conditioned support may be carried out in a similar manner to immobilizing a metal alkoxide on a support as described above. The immobilizing of a metal alkoxide on a support may be carried out in a single step or in multiple steps. A reactor containing reactivated catalyst is then ready to go back into service.

Addition of trace amounts of soluble active metal components of catalysts into the feed stream, as described above, may result in a stable catalyst performance for prolonged cycle time. As an example, transesterification of DEC with phenol was performed in an up-flow, once-through, fixed bed reactor with about 45 to about 60 ppm by weight Ti added to the feed stream. There has been little sign of catalyst deactivation during more than 14 months of continuous on-stream time.

The addition of a trace amount of active metal compounds as disclosed herein may be useful for continuous commercial production of various organic carbonates or carbamates. The reactions producing organic carbonates may be performed in a single reactor, a series of multiple reactors, or a multiple parallel reactor system, as a specific reaction system dictates. For example, the reactions may be carried out in a single catalytic distillation column reactor or a series of multiple catalytic distillation column reactors, where a solid catalyst or two different solid catalysts are placed. Optionally a series of multiple slurry reactors may also be used to produce an organic carbonate. The addition of a trace amount of soluble active metal component to a feed stream may be to only the first reactor in a series of multiple reactors. The desirable amount of trace amount of active metal component in a feed stream depends on the specific active metal element for specific feed components. For the transesterification of a dialkyl carbonate with phenol, it may range from about 15 ppm to about 400 ppm by weight in some embodiments; from about 20 ppm to about 300 ppm in other embodiments; and from about 25 ppm to about 200 ppm in yet other embodiments, depending on the metal. For a feed stream composed of diethyl carbonate and phenol, for example, a desirable amount of Ti may be from about 20 ppm to about 150 ppm in some embodiments; and from 30 ppm to 100 ppm by weight in yet other embodiments. The amount of the active metal component in the feed stream is approximately one or two order of magnitude lower than the concentration of homogeneous catalyst in the reaction medium of prior arts.

The Ti concentration in a reactor effluent stream is usually in a range from about 20 ppm to about 100 ppm, depending on the amount of active metal concentration in the feed stream to a reactor. At this level, it is generally not economically favorable to recover Ti from the reactor effluent streams for recycle, although one may choose to do so. The active metal component in the reactor effluent stream may be recovered from heavy bottom streams of the crude DPC recovery column as solid material and converted to soluble organometallic compound to be reused by reacting with organic carbonate or a mixture of organic carbonate and alcohol at an elevated temperature. The recovered organometallic compound may be a metal alkoxide, a metal alkoxy alkyl carbonate (metal salt of a carbonic acid monoester) or a mixture of these.

To recover the soluble active metal component in the bottom stream of the DPC recovery column as solid material, the heavy waste bottom stream from DPC recovery column may be treated with hot water or a mixture of steam and water to precipitate the metal component as a solid. In case of a solid titanium containing catalysts, the solid titanium precipitate in the aqueous phase is separated from liquid by using conventional methods, such as filtration or centrifuge. The separated solid is converted to soluble material by treating with a liquid stream containing a dialkyl carbonate or a mixture of dialkyl carbonate and an alcohol at a temperature from 121 to 343° C. (250 to 650° F.) under pressure for a period from 10 minutes to 80 hours in some embodiments, and from 20 minutes to 45 hrs in other embodiments. The pressure is sufficiently high so that dialkyl carbonate or a mixture of alcohol and dialkyl carbonate should, at least partially, exist as liquid in the column. Optionally, the liquid stream may contain an inert solvent such as benzene, toluene, hexane, heptane, ether, etc. Examples of the liquid stream are mixtures of ethanol and DEC or methanol and DMC. The content of dialkyl carbonate in a mixture of an alcohol and dialkyl carbonate may range from 0.1 wt % to less than 100 wt %.

The reactions producing organic carbonates or carbamates may be performed in a single reactor or in a series of multiple reactors in various arrangements of the reactors with suitably arranged distillation columns for the cost effective separation of reaction products and for the recycle of unreacted reactants. Alternatively the reactions may be performed in a single or a multiple parallel reactors. Various other arrangements of reactors and distillation column may be devised by those skilled in the art.

A reaction may be performed in a single catalytic distillation column, in a series of multiple catalytic distillation columns, in a series of multiple fixed tubular or tank reactors or any combination of different types of reactors. When three catalytic distillation columns are used to produce DPC, a solid catalyst is placed in the first two reactors in series for the transesterification. The third distillation column reactor may contain a solid catalyst or alternatively may not contain a solid catalyst. The disproportionation in the third reactor may be performed by utilizing only soluble homogeneous catalyst present in the reaction medium.

Reactions performed in traditional tubular fixed bed reactors may be performed in up-flow or down-flow mode. The reactions producing alkyl aryl carbonate, such as EPC, and diaryl carbonate, such as DPC, for example, may be performed in a liquid phase, but may also be performed in a mixed phase system in the presence of one or more solid catalysts. The two reactors in series for the transesterification may alternate periodically between being first and second reactor to prolong cycle time. The third reactor for disproportionation of EPC to produce DPC and DEC may be performed in the lower half of the phenol recovery column, which may be operated at sub-atmospheric pressures. In selected embodiments, processes disclosed herein may be useful for producing diphenyl carbonate by performing transesterification of diethyl carbonate with phenol followed by disproportionation of ethyl phenyl carbonate.

A trace amount of a soluble active metal compound, such as ethyl phenyl titanate or ethoxy titanium ethyl carbonate, or a mixture of titanium alkoxide and alkoxy titanium alkyl carbonate, for example, may be added into the liquid reaction medium fed into the first reaction zone. Alternatively, disproportionation may be performed in a catalytic distillation column to which the bottoms stream from a phenol recovery column is introduced at a proper point in the upper midsection of the column. Disproportionation may also be performed in a catalytic distillation column to which the bottoms stream from a transesterification reactor is directly introduced without phenol removal (phenol may be recovered from the bottoms stream from the EPC disproportionation column). The first reaction zone may include two catalytic distillation columns in series or two parallel catalytic distillation columns for transesterification of DEC with phenol. The second reaction zone may include a catalytic distillation column reactor for disproportionation of EPC to DPC and DEC. One may choose DMC in place of DEC and MPC in place of EPC.

Catalytic distillation column reactors for the first reaction zone may be loaded with one or more solid catalysts, such as titanium alkoxide immobilized on a silica support or titanium oxide supported on a silica support. In general, there are two alternative processes for the continuous production of diphenyl carbonate that may be used, in the case where more than two reactors are used.

In a first process for the continuous production of diphenyl carbonate, there may be from three to seven catalytic distillation column reactors in various embodiments, from three to four catalytic distillation columns in selected embodiments. Out of these catalytic distillation column reactors, one or more may serve as a spare reactors to replace the least active reactor out of the multiple reactors in service. Of the multiple distillation column reactors, two to six reactors may be used to primarily produce EPC. The remaining catalytic distillation column reactors may serve as a second reaction zone, wherein primarily the EPC disproportionation to DPC and DEC occurs. DEC and at least a portion of the phenol in the stream from the first reaction zone are removed from the heavy effluent stream of the first reaction zone prior to entering the second reaction zone. Alternatively, removal of phenol in the heavy effluent stream of the first reaction zone may be delayed until after disproportionation, depending on the concentration of phenol in that stream. As the catalyst in service ages, the catalyst activity slowly deactivates. There are three different options for rotating the multiple reactors in series between service for production of aromatic carbonates and catalyst reactivation:

(1) cyclic rotation of all the reactors in sequential order after a given service time with the oldest reactor coming out of service for catalyst reactivation while bringing a reactor having fresh or reactivated catalyst into service as the first reactor in the series of multiple reactors (i.e., new→first reactor, first reactor →second; second→third; and third→reactivation or catalyst replacement), or optionally bring a new reactor into service as the last reactor in the series, as the second reactor moves up as the first reactor (reverse of forward sequence presented);

(2) the reactors are divided into two groups of first reaction zone and second reaction zone reactors with each group having a spare reactor for rotation between service and catalyst replacement/reactivation;

(3) bring the least active reactor in a series of the multiple reactors out of service for the catalyst reactivation, as necessary, and bring a spare reactor (wherein the catalyst already had been reactivated) into service to replace the reactor taken out of service.

In an alternative process, two reactors in series are used as the first reaction zone. The sequence of the two reactors are periodically alternated between being the first reactor and the second reactor after servicing for a given period of time, say every 6000 hours; this rotation repeats as many times as necessary. There is no spare reactor for the second reaction zone. This type of operation is possible due to the addition of trace amounts of active metal compounds to the first reactor in the series. DEC and phenol in the stream from the first reaction zone are removed by distillation, and then the remaining stream is subjected to disproportionation of EPC to produce DPC in the second reaction zone. There are two ways carrying out the disproportionation.

(1) In the first method, disproptionation is performed in the presence of solid catalyst in a fixed bed reactor such as catalytic distillation reactor. There is a spare reactor for the replacement of the reactor in service. The deactivated catalyst is subjected to catalyst reactivation described earlier.

(2) In the second method, the disproportionation is performed in a catalytic distillation reactor in the absence of a solid catalyst and there is no spare reactor. The active soluble metal species in the stream coming from the first reaction zone serve as a homogeneous catalyst for the disproportionation reaction.

It is understood that the catalytic distillation column, wherein a solid catalyst is either present or absent, for the second reaction zone is designed such that the top half section of the column (phenol recovery section) serves primarily to distill off phenol in the incoming reaction mixture from the first reaction zone and the bottom half section serves primarily to perform disproportionation of EPC or MPC. In an alternative process design, a phenol recovery column and a catalytic distillation column are separated into two columns, although some disproportion may occur in the bottom section of phenol recovery column. As stated above, depending on the concentration of phenol in the incoming feed stream, a phenol recovery may be delayed until after disproportionation, although some of phenol may be stripped off in the catalytic distillation column as overhead vapor stream along with DEC. The catalytic distillation column for disproportionation may be operated under a subatmospheric pressure.

FIG. 1 is a simplified flow diagram illustrating a process for the continuous production of DPC with three catalytic distillation columns according to embodiments disclosed herein. Two catalytic distillation columns in series serve as the first reaction zone for transesterification of DEC with phenol to produce EPC and ethanol in the presence of a solid catalyst, and a catalytic distillation column serves as the second reaction zone for disproportionation of EPC to produce DPC and DEC.

Referring now to FIG. 1, a process for the production of DPC from DEC and phenol according to embodiments disclosed herein is illustrated. C1 and C2 are catalytic distillation columns for performing transesterification; C3 is an ethanol recovery column; C4 is a DEC recovery column (phenetole purge column); C5 is a catalytic distillation column for disproportionation and phenol recovery; C6 is an EPC recovery column; and C7 is a DPC recovery column The columns C1 and C2 are a series of catalytic distillation columns, wherein structured packing devices are placed in reaction zone R1 and R2, respectively. The specially structured packing devices contain solid catalyst. Phenol and DEC containing feed streams 1 and 4, respectively, are introduced to a tray in the upper section of catalytic distillation columns C1 and C2, above the catalytic reaction zones R1 and R2. The mole ratio of DEC to phenol in the fresh DEC and fresh phenol feed streams may be approximately 1:2. The mole ratios of DEC to phenol in the catalytic reaction zones R1 and R2, however, are controlled to be from about 12:1 to about 1:2.5 in some embodiments; from about 10:1 to about 1:2 in other embodiments; and from about 7:1 to about 1:1 in yet other embodiments.

A soluble organometallic compound is also introduced to a tray in the top section of C1 via flow line 3. For example, for a titanium-containing solid catalyst in reaction zones R1 and R2, a solution containing a soluble titanium compound such as $Ti(OEt)_{4-x}(OPh)_x$ (where x is 0, 1, 2, 3 or 4), or titanium salts of carbonic acid monoesters, such as ethoxy titanium ethyl carbonates, or mixtures of these, may be introduced to the top of the first catalytic distillation column reactor C1. The solvent for the catalyst solution can be DEC, a mixed solution of DEC and phenol, a mixed solution of DEC and ethanol, or a mixed solution of DEC, ethanol, and phenol, for example.

The flow rate of the catalyst solution may be controlled such that the concentration of titanium in the liquid stream above the catalyst in the first column reactor is from about 20 ppm to about 100 ppm active metal (titanium for the example catalyst solutions listed in the previous paragraph) by weight in some embodiments; from about 25 ppm to about 80 ppm by weight in other embodiments; and from about 30 ppm to about 70 ppm by weight in yet other embodiments.

Overhead vapor streams 6 and 14 from the catalytic distillation columns C1 and C2 are sent to an ethanol recovery column C3 via flow line 8. This overhead stream may also contain minor amounts of by-products such as diethyl ether and carbon dioxide and a trace amount of phenol. Diethyl ether and carbon dioxide may be removed as overhead vapor stream 9. Ethanol may be recovered via a side drawn from column C3 via flow line 10. The bottom stream 11 may recycle DEC from column C3 to catalytic distillation column reactors C1 and C2 via flow lines 12 and 13, respectively.

Column C1 may be operated such that the temperature of the catalytic reaction zone R1 is in the range from about 160° C. to about 210° C. (about 320° F. to about 410° F.). The overhead pressure in column C1 may be within the range from about 2 bar absolute to about 4.8 bar absolute (about 14.7 psig to about 55 psig). The bottom stream 7 from the first catalytic distillation column C1 may be introduced to the top of catalytic distillation column C2, which may be operated such that a temperature in the catalytic reaction zone may be in the range from about 162° C. to about 216° C. (about 325° F. to about 420° F.) and the column may be operated at an overhead pressure in the range from sub-atmospheric, about 1 bar (0 psig), to about 4.5 bar (51 psig). Optionally small fractions of recycle or fresh DEC stream can be introduced to the column C1 and C2 via flow lines 4a and 4b, respectively.

The concentration of EPC increases moving down stages in the catalytic distillation columns C1 and C2. As some disproportionation of EPC to DPC and DEC occurs in column reactors C1 and C2, the concentration of DPC increases as well. The bottom stream 15 from distillation column reactor C2 is sent to DEC recovery column C4, where DEC is recovered in overhead vapor stream 16. Column C4 may be operated from a temperature of from about 127° C. to about 204° C. (about 260° F. to about 400° F.) at an overhead pressure from about 0.3 bar (about 4 psia) to about 1.5 bar (about 22 psia). Stream 16 may be introduced to ethanol recovery column C3 to separate DEC and phenol that may be in stream 16, where the DEC and phenol may be recycled via lines 11, 12, 13 to C1 and C2.

The overhead stream 16 from column C4 may also contain DEC and small amounts of phenetole, phenol, and ethanol. A side draw stream 18 from column C4 may be used as a phenetole purge stream, minimizing buildup of phenetole in the system.

Bottoms stream 17 from column C4 contains homogeneous catalyst species coming from columns C1 and C2. Bottoms stream 17 may be introduced at a suitable position in the top section of distillation column C5. Column C5 may be used to perform disproportionation of EPC, and may optionally contain a heterogeneous catalyst in reaction zone R3.

The column C5 may be designed and operated to serve two purposes: remove phenol in stream 17 and the co-product DEC from the EPC disproportionation as overhead stream 19; and, disproportionation of EPC to form DPC. Column C5 is operated so that the homogeneous catalytic reaction zone R3 temperature is in the range from about 165° C. to about 210°

C. (about 330° F. to about 410° F.), and the column overhead pressure is from about 0.07 bar (about 1 psia) to about 0.6 bar (9 psia).

The overhead vapor stream 19 from C5, containing DEC and phenol, may be recycled to columns C1 and C2 via streams 20 and 21, respectively. C5 bottoms stream 22 (which contains DPC, unconverted EPC, phenol, phenetole, heavies and soluble Ti catalyst) from C5 is introduced to EPC recovery column C6, which may be operated at a temperature from about 168° C. to about 213° C. (about 335° F. to about 415° F.) and under sub-atmospheric pressures in the range from about 0.03 bar (about 0.4 psia) to about 0.55 bar (8 psia).

EPC Column C6 bottoms stream 25 is introduced to the DPC recovery column C7 to recover DPC as side-draw stream 27. The DPC recovery column C7 is operated under high vacuum (e.g., <0.03 bar (<0.4 psia). Overhead stream 26 may be combined with EPC column C6 overhead stream 23 and recycled to column C5 via line 24.

DPC recovery column C7 bottoms stream 28, containing heavies and soluble catalyst may be recovered or disposed. If desired, where titanium catalysts are used and fed to the reactor, for example, one may recover titanium as soluble Ti catalyst (Ti(OEt)$_4$ or a mixture of Ti(OEt)$_4$ and ethoxy titanium ethyl carbonates) for recycle, as discussed earlier. As one disposal method, stream 28 can be sent to a titanium refinery to recover Ti. One can recover DPC from stream 22 in alternate recovery and purification trains, which are within the knowledge of those of ordinary skill in the art.

Alternatively, as mentioned above, the disproportionation of EPC to DPC and DEC may be performed in the presence of a solid catalyst in the catalytic distillation column C5. Solid catalysts in C5 may, however, deactivate faster than solid catalysts in the second catalytic distillation column C2, as illustrated in FIG. 1.

As discussed above, where C5 includes a solid catalyst, various options may be used to cycle the distillation column reactors so as to maintain sufficient catalytic activity for the process. Sufficient valves and piping, not illustrated, may be provided to allow for the cycling of the reactors, and is within the skill of those in the art.

Figure 2:
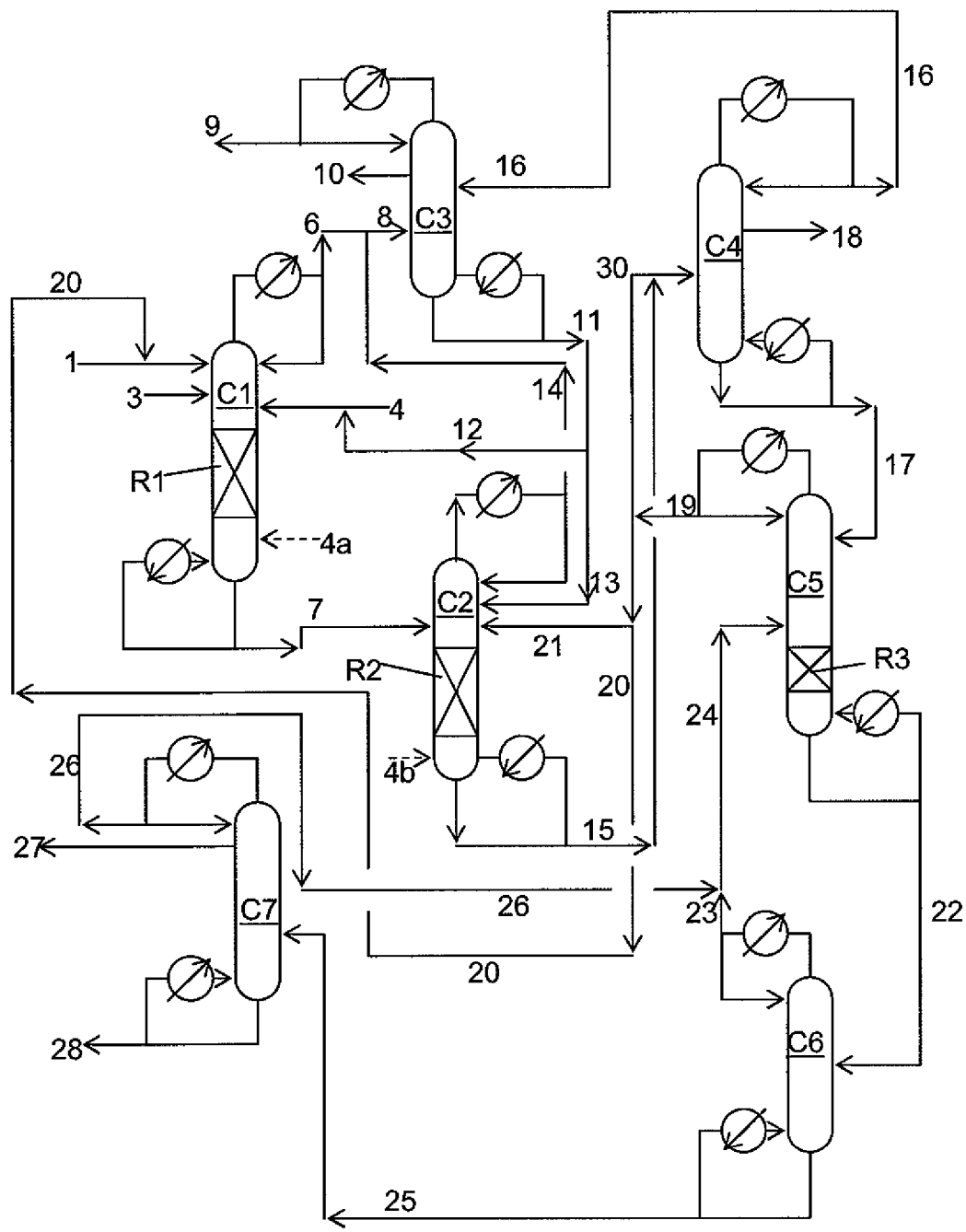
FIG. 2 is a simplified process flow diagram illustrating a process for the production of diaryl carbonates according to embodiments disclosed herein.

FIG. 2 is an alternative process flow diagram, where like numerals represent like parts. There are a similar number of catalytic distillation columns to perform transesterification and disproportionation, and columns for the material separations as in FIG. 1. However, a fraction of overhead stream 19 from catalytic distillation column C5 may be recycled back to DEC recovery column C4 via line 30. Recycle via line 30 may thus allow an alternative method for purging phenetole.

Figure 3:
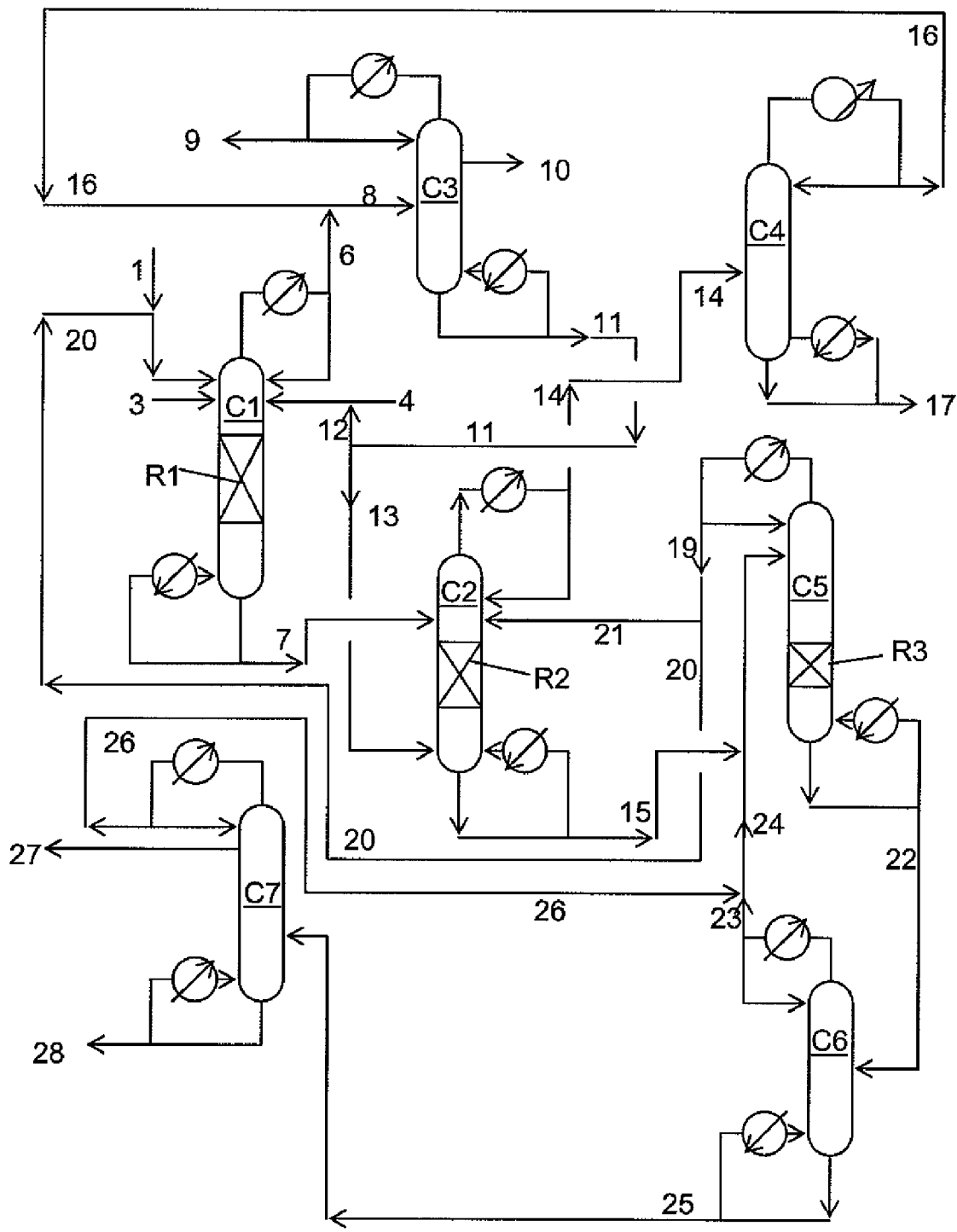
FIG. 3 is a simplified process flow diagram illustrating a process for the production of diaryl carbonates according to embodiments disclosed herein.

FIG. 3 illustrates another alternative process flow scheme according to embodiments disclosed herein, similar to FIGS. 1 and 2, where like numerals represent like parts. The first catalytic distillation column C1 is operated in more or less similar fashion to the previous cases (FIGS. 1 and 2). However, the operation of the second catalytic distillation column C2 and the DEC recovery column C4 are operated in different fashions from previous cases. Column C2 may be operated at a higher temperature and a lower pressure than previous cases. The recycle DEC stream 13 is introduced into the bottom of the column C2. Optionally a part of the fresh DEC stream 4 may also be introduced to the bottom of column C2. Due to operation at higher temperature and lower pressure, C2 bottoms stream 15 contains less DEC. C2 overhead stream 14 contains phenetole, among other components. Stream 14 may be introduced to F column C4, where C4 bottoms stream 17 is the phenetole purge stream.

Extremely pure DPC may be prepared from crude DPC products produced according to embodiments disclosed herein. The high-purity DPC may be produced by fractional crystallization using hydrocarbon-ether mixtures, such as bexane-diethyl ether mixtures. In some embodiments, the only detectable impurity, other than phenol, in the purified DPC product is xanthone in an amount up to about 0.5 ppm by weight. The phenol in the purified DPC may be a trace amount, such as from about 5 to about 17 ppm by weight. Trace analyses of impurities in DPC produced according to embodiments disclosed herein indicate that the purity of the DPC obtained is much higher than for DPC that may be obtained from common vendors for laboratory chemicals.

EXAMPLES

With the exception of Experiment 1, all transesterification reactions of DEC with phenol were performed in up-flow boiling point reactor. Therefore, vapor and liquid phases coexists in the catalytic reaction zone. The dimension of the fixed bed reactor was 1.3 cm (½ inch) diameter by 6.5 cm (25 inches) long. The reactor had separately controlled top and bottom heating zones. The fixed bed reactor was mounted vertically. The volume of solid catalysts was 25 ml.

Comparative Experiment 1

Experiments for transesterification of DEC with phenol were performed in the presence of homogeneous titanium alkoxide catalyst by using a stirred 50 ml autoclave reactor. The autoclave was filled with about 35 ml of a DEC/phenol mixture, as given in Table 1. The autoclave was immersed in an oil bath to control reaction temperature. After performing the reaction, the autoclave was removed from oil bath and quenched with cold water. No diphenyl ether was observed in any reaction mixture. The results of the reactions are listed in Table 1

TABLE 1

| Temperature, °C. (° F.) | Pressure, bar (psig) | Duration (h) | Catalyst Type | Catalyst Amount (wt. ppm) | DEC/PhOH Mole Ratio | Phenol Conversion (mole %) | Selectivity of EPC and DPC (mole %) |
|---|---|---|---|---|---|---|---|
| 174 (345) | 2.7 (25) | 2 | Titanium Ethoxide | 4767 | 2.32 | 4.54 | 62.97 |
| 174 (345) | 2.7 (25) | 3 | Titanium Ethoxide | 4767 | 2.32 | 15.45 | 15.24 |
| 174 (345) | 2.7 (25) | 4 | Titanium Ethoxide | 4767 | 2.32 | 14.93 | 20.45 |
| 174 (345) | 2.5 (22) | 2 | Titanium n-butoxide | 42 | 2.35 | 0.13 | 91.2 |
| 174 (345) | 2.7 (25) | 4 | Titanium n-butoxide | 42 | 2.35 | 3.56 | 95.01 |

When the Ti concentrations in the feed solutions were 4767 ppm by weight, the maximum phenol conversion after about 3 hours reaction time was about 15% with very poor selectivity (<20.5 mole %) of FPC and DPC. When the reaction time was 2 hours, the conversion of phenol was less than 5%; the selectivity was better, but still poor (63 mole %). When the catalyst concentration was reduced to 42 ppm Ti by weight, the selectivity was much improved, but conversion was poor.

Comparative Experiment 2

The objective of this experiment was to obtain experimental data of homogeneous K catalyst as a reference to compare with the results of examples according to embodiments disclosed herein. There was no solid catalyst in the reactor. The 25 ml space for a solid catalyst in the reactor was empty. A reaction mixture of 73.3 wt % DEC and 26.7 wt % Phenol (2.19 mole ratio of DEC/PhOH) having various amounts of homogeneous catalyst of $Ti(OEt)_{4-x}(OPh)_x$ (x=~2) were passed through the reactor up-flow under various reaction conditions from 0 to 768 hours on stream and then from 1266 to 1362 hours on stream. The concentrations of Ti in the feed mixture ranged from 59 ppm to 709 ppm Ti by weight, as shown FIG. 4. The flow rate was 0.5 ml/min for most of run time. The history of feed flow rate is listed in Table 2.

TABLE 2

| Transesterification | | | | |
|---|---|---|---|---|
| | Time on Stream (h) | | | |
| | 0-333 | 333-354 | 354-426 | 426-1362 |
| Feed flow rate (ml/min) | 0.5 | 0.6 | 0.4 | 0.5 |

Ethanol in the composite transesterification products was distilled off and then DEC was added to adjust the DEC/PhOH mole ratio to 2.19 by adding DEC to prepare second transesterification feeds. The second transesterification feeds had about 3.4 wt % EPC, about 250 ppm phenetole and about 300 ppm DPC by weight, on average. The history of the homogenous catalyst concentrations in the second transesterification feeds is listed in Table 3.

TABLE 3

| | Time on Stream (h) | | | | | |
|---|---|---|---|---|---|---|
| | 768-834 | 834-930 | 930-1026 | 1026-1098 | 1098-1194 | 1194-1266 |
| Ti ppm by weight | 188 | 113 | 174 | 197 | 300 | 220 |

Using these feed mixtures, the second transesterification was performed from 768 to 1266 hours on stream time. The phenol conversion in FIG. 4 for this time period is the overall conversion through both 1st and 2nd transesterification.

Figure 4:
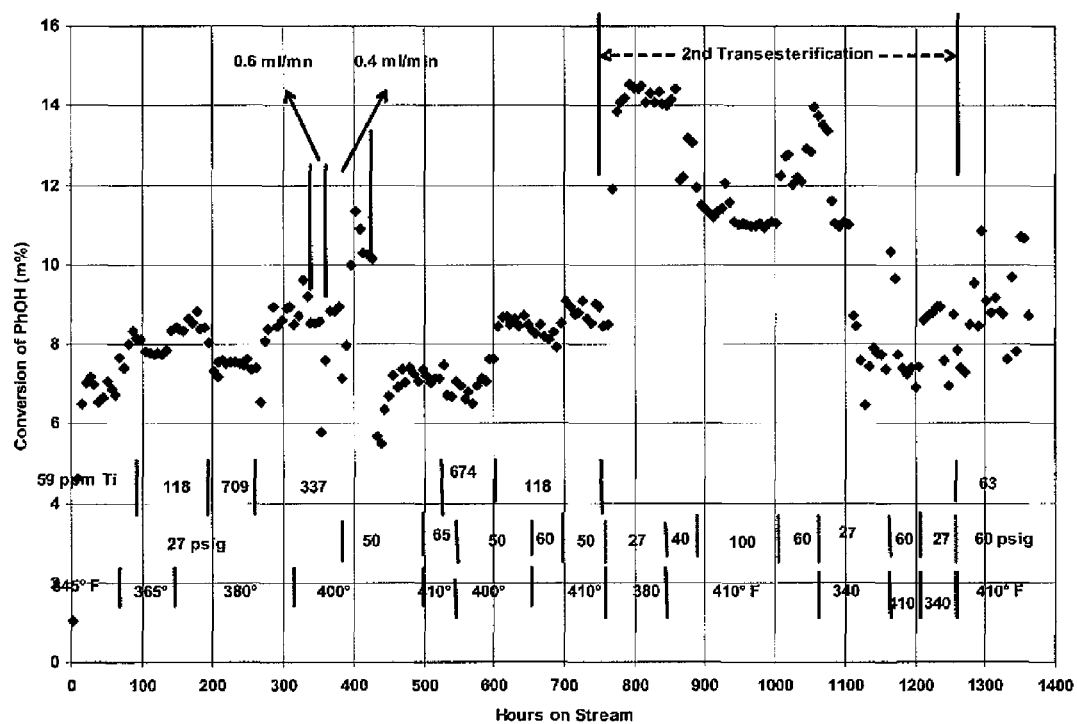
FIG. 4 is a graphical representation of transesterification using a homogeneous catalyst.

The range of the reaction temperatures was from 174° C. to 210° C. (345° F. to 410° F.) as indicated in FIG. 4. The range of the reactor pressures was from about 2.9 to about 5.5 bar (about 27 psig to about 65 psig). All reactions were carried out under boiling condition. Therefore, the reaction was performed as a mixed phase system (vapor and liquid). The temperatures in FIG. 4 are reactor bottom temperatures.

When the catalyst concentration in the reaction mixture is higher than 118 ppm Ti, there were adverse effects of the catalyst on the conversion of phenol. The cause of this adverse effect is not completely understood, but may be the effect of two ethoxy groups on Ti catalyst. Also, when the Ti concentration in a feed was higher than about 300 ppm, there was line plugging problems in the reactor effluent line due to precipitation of Ti catalyst. Therefore, a pair of in-line filter was installed to address the line plugging problems. When the concentration of Ti was 59 ppm, the temperature effect on the phenol conversion is moderate, indicating low activation energy of transesterification of DEC with phenol. The highest phenol conversion for the first transesterification was about 11.3 mole % with 337 ppm Ti at 204° C. (400° F.) and 4.5 bar (50 psig). The highest phenol conversion for the second transesterification was about 14.5 mole % at 193° C. (380° F.) and 2.9 bar (27 psig) with 188 ppm Ti concentration. The experiment also suggests lower conversion for liquid phase reaction (410° C. and 7.9 bar (100 psig)), as expected.

Experiment 3

The objectives of this experiment were to demonstrate (1) the in situ preparation technique of titanium n-butoxide immobilized on a silica gel support, (2) technique for catalyst reactivation, and (3) the performance of a dual phase fixed bed reactor for the transesterification. The dual phase of vapor and liquid in the catalytic reaction zone was created by boiling the reaction mixture.

45.74 g of granular silica gel (+8 mesh) was treated with a sodium hydroxide solution (7.5 g NaOH in 550 ml water) at about 42° C. temperature for 7 minutes with stirring at ambient temperature. The silica gel was washed, first with cold water and then with hot water (about 80° C.), to remove trace amounts of sodium on the silica. The resulting treated silica gel was dried at 125° C. for 2 hours and then at 300° C. for 2 hours under nitrogen purge. The dried silica gel support had 23 ppm Na by weight. The treated silica gel support had the following properties: 291 $m^2/g$ BET, 1.052 $cm^3/g$ pore volume and 16.3 nm average pore diameter.

25 ml of the dried granular silica gel support (about 9.3 g) was loaded in the reactor. A titanium n-butoxide solution was prepared by dissolving 27 g of titanium n-butoxide in 500 ml dried toluene. The titanium n-butoxide solution was placed in a reservoir. After circulating the titanium n-butoxide solution through the reactor up-flow at 15 m/min and ambient temperature for 15 minutes, the reactor was heated to 168° C. (335° F.) at a pressure of about 5.5 bar (65 psig). The circulation was continued at 168° C. (335° F.) for 4.5 hours and then the reactor was cooled. After draining excess solution from the reactor, the supported catalyst was washed with dry toluene up-flow at 4 ml/min for 1.5 hours. The washed catalyst was dried at 168° C. (335° F.) in 350 cc/min nitrogen gas (up-flow) for 2 hours. The resulting in situ-prepared titanium n-butoxide catalyst grafted on silica gel granular support was tested for transesterification of DEC with phenol.

Figure 5:
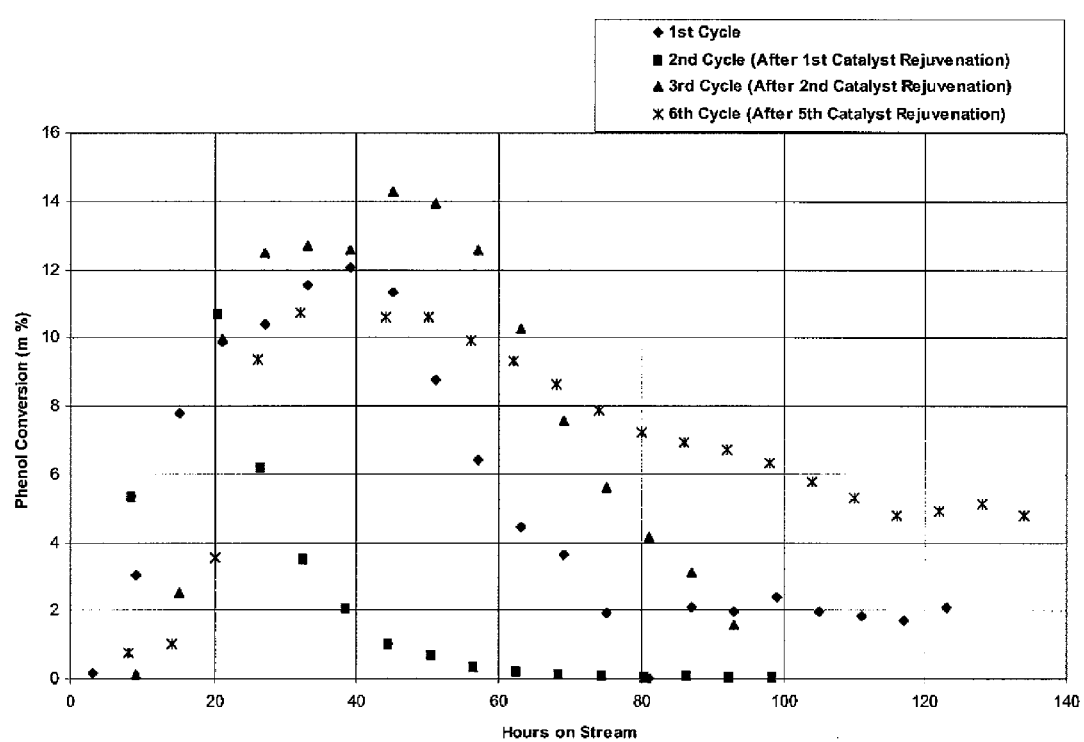
FIG. 5 is a graphical representation of catalyst activity following catalyst reactivation according to embodiments disclosed herein.

1st Cycle Transesterification: Transesterification of DEC with phenol was performed in the presence of the in situ-prepared solid catalyst in a fixed bed boiling point reactor. A mixture of DEC and phenol (25.57 wt % phenol and 74.43 wt % DEC; 2.32 mole ratio of DEC/PhOH) was passed through the solid catalyst bed up-flow at 168° C. (335° F.), 2.4 bar (20 psig) and at a 0.2 ml/min feed flow rate. This test constituted the 1st cycle of transesterification and the results are illustrated in FIG. 5. The catalyst reached its maximum activity (12 mole % conversion of phenol) at about 40 hours on stream. After about 80 hours on stream time, the catalyst lost most of its activity. This deactivated catalyst was subjected to a 1st reactivation as follows.

1st Catalyst Reactivation: The catalyst reactivation comprises two steps; catalyst depolymerization/surface conditioning and redeposition of active titanium metal on the catalyst. After draining the reactor, the catalyst was washed with dried toluene (300 ml) up-flow at ambient temperature and then the toluene was drained from the reactor. 0.19 g titanium n-butoxide was dissolved in 2 liters of an ethanol solution prepared by mixing 400 ml ethanol and 1700 ml toluene. The titanium solution was passed through the reactor at 2.2 ml/min up-flow at 168° C. (335° F.) and 12 bar (160 psig) for 13.5 hours. After draining excess titanium solution from the reactor, the catalyst was dried at 168° C. (335° F.) under ambient pressure in 200 cc/min nitrogen up-flow for 45 minutes. A titanium n-butoxide solution (135 g titanium n-butoxide in 2 liters toluene) was circulated through the reactor at 15 ml/min up-flow at room temperature for 20 minutes and then at 168° C. (335° F.) and 10.7 bar (140 psig) for 4 hours. After cooling, excess solution was drained from the reactor. The catalyst was washed with 4 ml/min toluene up-flow for 1.5 hours. The washed catalyst was dried at 168° C. (335° F.) in 300 cc/min nitrogen gas up-flow for 2 hours. The reactivated catalyst was used in a second transesterification cycle as follow.

2nd Cycle Transesterification: The transesterification was performed in identical manner to 1st cycle. The result is illustrated in FIG. 5. The reactivated catalyst did not perform as good as in the 1st cycle, and the catalyst died only after about 40 hours on stream. A 2nd catalyst reactivation was then performed as follow.

2nd Catalyst reactivation: After draining material from the reactor, the catalyst in the reactor was washed with dried toluene at 10 ml/min up-flow at ambient temperature for 30 min and then the toluene was drained from the reactor. The catalyst in the reactor was dried at 168° C. (335° F.) in nitrogen gas at 250 cc/min up-flow for 1 hour. A solution prepared by mixing 8 ml water, 500 ml ethanol and 1100 ml toluene was passed though the reactor at 2.2 ml/min up-flow at 168° C. (335° F.) and 12 bar (160 psig) for 12.1 hours. After draining excess solution from the reactor, the catalyst was dried at 168° C. (335° F.) under ambient pressure in 200 cc/min nitrogen up-flow for 1 hour. A titanium n-butoxide solution (135 g titanium n-butoxide in 2 liters toluene) was circulated through the reactor at 15 ml/min up-flow at room temperature for 20 minutes and then at 168° C. (335° F.) and 10.7 bar (140 psig) for 6 hours. After cooling, excess titanium solution was drained from the reactor. The catalyst was washed with 4 ml/min toluene up-flow for 1.5 hours. The washed catalyst was dried at 168° C. (335° F.) in 300 cc/min nitrogen gas up-flow for 2 hours. The reactivated catalyst was the used in a third cycle of the transesterification reaction as follow.

3rd Cycle Transesterification: The transesterification was performed in identical manner to 1st cycle. The result is illustrated in FIG. 5. The reactivated catalyst performed as well as the catalyst in the 1st cycle. Nevertheless the catalyst died after about 90 hours on stream.

The deactivated catalyst in the reactor was subjected to two more catalyst reactivation under similar condition and then two more transesterifications, with similar results. After the 5th cycle of transesterification reactions, the catalyst was subjected to a 5th catalyst reactivation, as follow. The history of catalyst reactivations from the 3rd to 5th is described below.

3rd Catalyst Reactivation. After draining out all the material in the reactor leftover from 3rd cycle transesterification, the catalyst in the reactor was washed with dried toluene 10 ml/min up-flow at ambient temperature for 1 hour and then excess toluene was drained from the reactor. The catalyst in the reactor was dried at 157° C. (315° F.) in nitrogen gas at 250 cc/min up-flow for 1 hour. A solution prepared by mixing 8 ml water, 500 ml ethanol and 1100 ml toluene was passed though the reactor at 2.2 ml/min up-flow at 157° C. (315° F.) and 2.7 bar (25 psig) for 12.1 hours. After draining excess solution from the reactor, the catalyst was dried at 149° C. (300° F.) under ambient pressure in 200 cc/min nitrogen up-flow for 1 hour. A titanium n-butoxide solution (135 g titanium n-butoxide in 2 liters toluene) was circulated through the reactor at 15 ml/min up-flow at room temperature for 20 minutes and then at 157° C. (315° F.) and 7.2 bar (90 psig) for 6 hours. After cooling, the excess solution was drained from the reactor. The catalyst was washed with 4 ml/min toluene up-flow for 1.5 hours. The washed catalyst was dried at 163° C. (325° F.) in 300 cc/min nitrogen gas up-low for 2 hours.

The reactivated catalyst was the subject to the 4th transesterification. The performance of the reactivated catalyst was similar to the 2nd cycle transesterification. The result is not shown in FIG. 5.

4th Catalyst Reactivation: After draining material in the reactor leftover from the 4th cycle transesterification, the catalyst in the reactor was washed with dried toluene at 10 ml/min up-flow at ambient temperature for 1 hour and then the excess toluene was drained from the reactor. The catalyst in the reactor was dried at 157° C. (315° F.) in nitrogen gas at 250 cc/min up-flow for 1 hour. A solution prepared by mixing 8 ml water, 500 ml ethanol and 11100 ml toluene was passed though the reactor at 2.2 ml/min up-flow at 157° C. (315° F.) and 2.7 bar (25 psig) for 12.1 hours. After draining excess solution from the reactor, the catalyst was dried at 149° C. (300° F.) under ambient pressure in 200 cc/min nitrogen up-flow for 1 hour, A titanium n-butoxide solution (135 g titanium n-butoxide in 2 liters toluene) was circulated through the reactor at 15 ml/min tip-flow at room temperature for 20 minutes and then at 157° C. (315° F.) and 7.2 bar (90 psig) for 6 hours. After cooling, excess solution was drained from the reactor. The catalyst was washed with 4 ml/min toluene up-flow for 1.5 hours. The washed catalyst was dried at 163° C. (325° F.) in 300 cc/min nitrogen gas up-low for 2 hours. The reactivated catalyst was then used in a 5th cycle of the transesterification. The performance of the catalyst was similar to 3rd cycle transesterification, The result is not shown in FIG. 5.

5th Catalyst Reactivation: After draining material from the reactor, the catalyst in the reactor was washed with 10 ml/min dried toluene up-flow at ambient temperature for 1 hour and then excess toluene was drained from the reactor. The catalyst in the reactor was dried at 124° C. (255° F.) in nitrogen gas 250 cc/min up-flow for 1 hour. Water was passed through the reactor at 0.3 ml/min down-flow at 152-154° C. (305-310° F.) and ambient pressure for 6 hours. The steam treated catalyst in the reactor was dried with 100 cc/min nitrogen gas down-flow for 1 hour 20 minutes at 146-149° C. (295-300° F.). A titanium n-butoxide solution (135 g titanium n-butoxide in 1600 ml toluene) was circulated through the reactor at 15 ml/min up-flow at room temperature for 20 minutes and then at 127° C. (260° F.) and 3.1 bar (30 psig) for 6 hours. After cooling, excess solution was drained from the reactor. The catalyst was washed with 4 ml/min toluene up-flow for 1.5 hours. The washed catalyst was dried at 138° C. (280° F.) in 300 cc/min nitrogen gas up-flow for 2 hours. The reactivated catalyst was then subject to a 6th transesterification as follow.

6th Cycle Transesterification: The transesterification was performed in identical manner to 1st cycle. The result is illustrated in FIG. 5. The reactivated catalyst performed as well as in the 1st cycle. Interestingly, the catalyst deactivated at a slower rate.

The above experiments demonstrate that it is possible to reactivate deactivated titanium alkoxide catalyst immobilized on a silica gel support in situ. However, the catalyst cycle length may be too short to practice this technology in large commercial reactors for the continuous production of aromatic carbonates.

Experiment 4

The objective of this experiment was to demonstrate the extended catalyst cycle length attainable by adding a trace amount (42 ppm Ti by weight) of a soluble Ti compound (titanium n-butoxide) into the feed stream. The deactivated catalyst from 6th cycle transesterification in Experiment 3 was again subjected to a 7th catalyst reactivation as follows. After draining material in the reactor, the catalyst in the reactor was washed with 10 ml/min dried toluene up-flow at ambient temperature for 1 hour and then excess toluene was drained from the reactor. The catalyst in the reactor was dried at 124° C. (255° F.) in 250 cc/min nitrogen gas up-flow for 1 hour. A mixed solution of water (4 wt %) in ethanol was passed through the reactor at 1.4 ml/min down-flow at 154° C. (310° F.) and ambient pressure for 6 hours. The catalyst in the reactor was dried with 150 cc/min nitrogen gas down-flow for 1 hour 25 minutes at 154° C. (310° F.). A titanium n-butoxide solution (67.5 g titanium n-butoxide in 800 ml toluene) was passed through the reactor at 15 ml/min up-flow at room temperature for 20 minutes and then at 127° C. (260° F.) under 3.4 bar (35 psig) for 6 hours. After cooling, excess solution was drained from the reactor. The catalyst was washed with 4 ml/mm toluene up-flow for 1.5 hours. The washed catalyst was dried at 138° C. (280° F.) in 300 cc/min nitrogen gas up-flow for 2 hours. The reactivated catalyst was subject to the 7th transesterification cycle as follows.

Figure 6:
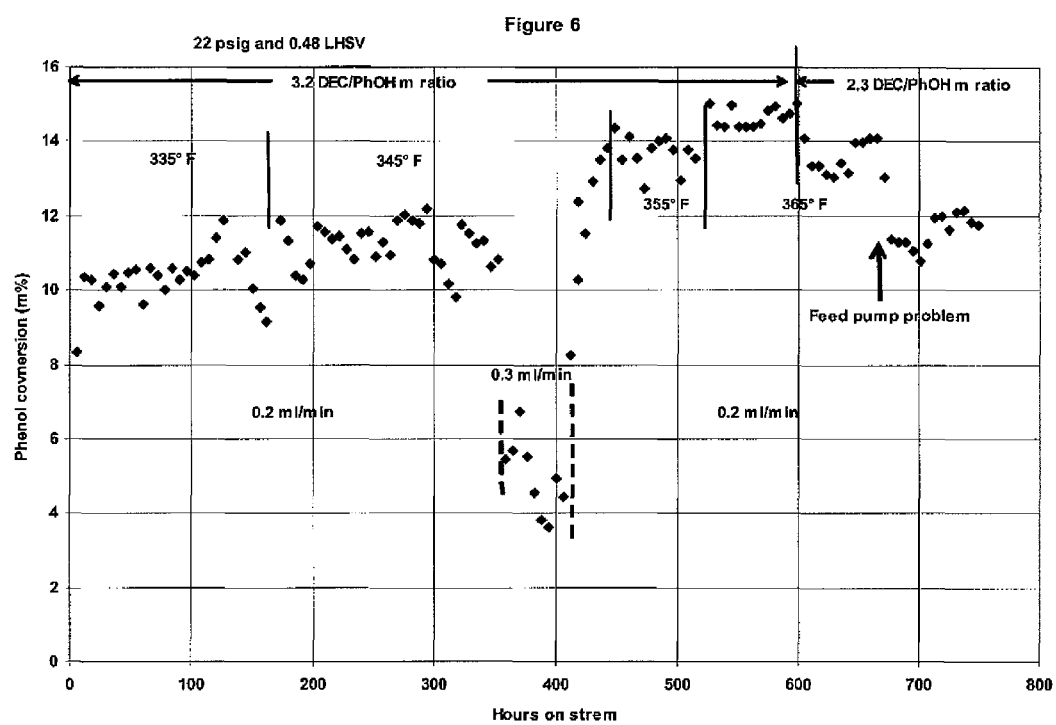
FIG. 6 is a graphical representation of solid catalyst activity when a trace amount of soluble organometallic compound is added to the reactor according to embodiments disclosed herein.

The 7th transesterification cycle was carried out by adding a trace amount (42 ppm Ti by weight) of titanium n-butoxide into the feed streams under various reaction conditions. Two different feed mixtures were used in this experiment. A mixed feed solution of 19.73 wt % phenol and 80.27 wt % DEC (3.24 mole ratio of DEC/PhOH) was used for the first 593 hours on stream, followed by 25.83 wt % phenol and 74.17 wt % DEC (2.29 mole ratio of DEC/PhOH) for the remainder of the run until shut down at 749 hours on stream. Titanium n-butoxide was blended into the premixed DEC/PhOH feed solutions. The feed rates were 0.2 ml/min for the first 353 hours on stream time, 0.3 ml/min from 353 to 401 hours on stream and then 0.2 ml/min to the end of run. The trace analyses of the product samples taken at various on stream time indicated 21 ppm Ti at 48 hours, 44 ppm Ti at 305 hours, 44 ppm Ti at 449 hours, 31 ppm Ti at 491 hours, 51 ppm Ti at 593 hours, 51 ppm Ti at 713 hours and 31 ppm Ti at 749 hours. The result of this experiment is illustrated in FIG. 6. The temperatures cited in FIG. 6 were the temperature readings at the bottom of the catalyst bed. The temperature readings at the top of the catalyst bed were usually 1.5-3° C. (3-5° F.) lower than the reactor bottom temperature, depending on the ethanol concentration in the product stream, indicating vaporization of ethanol at the top section of catalyst bed. Lower reactor effluent temperatures at the top of the catalyst bed became noticeable if the ethanol concentrations in the product were higher than about 1.2 wt %. Phenetole was the only detectable by-product. The phenetole selectivity based on phenol was less than 0.3 mole %.

As shown in FIG. 6, there was no catalyst deactivation during the entire run time (749 hours), successfully demonstrating that the catalyst cycle length could be extended from less than 80 hours to 749 hours or more by adding soluble 42 ppm Ti by weight into the feed stream.

The catalyst in the reactor was analyzed at the end of the run, and was mostly yellow granules, with some catalyst granules dark brown in color. Titanium phenoxide has an intense orange or amber like color for comparison. The analysis of the spent catalyst indicated 0.55 wt % Ti on the catalyst. This was a surprising discovery.

Experiment 5

The objectives of this experiment were to demonstrate (1) the need of pre-forming the catalyst prior to performing reactions, (2) catalyst reactivation, (3) extension of the catalyst cycle time, and (4) the need for controlling the water content (less than about 650 ppm by weight) in feed. In this experiment, silicon oxide pellets were used to prepare the support onto which titanium n-butoxide was grafted.

A silicon oxide pellet support (0.3 cm (⅛ inch), 555 ppm Na and 2500 ppm Al by weight, 280 $m^2$/g BET SA and 1 cc/g PV) was used to prepare an immobilized titanium n-butoxide catalyst. 100 g of silicon oxide pellets was treated at about 52° C. for 5 minutes with stirring with a sodium hydroxide solution (10 g NaOH in 570 ml water). The silica was washed with cold water thoroughly and then with hot water (about 80° C.) to remove trace amounts of sodium on the silica. The treated silica was first dried at room temperature, then dried at 130° C. for 1.5 hours and then at 150° C. for 1 hour in a vacuum oven. The dried silica support had 150 ppm Na by weight. The prepared silica support had the following properties: 252 $m^2$/g BET, 1.035 $cm^3$/g pore volume and 15.7 nm average pore diameter.

25 ml of the dried silicon oxide pellets (9.72 g) was loaded in the reactor. A reservoir for the catalyst solution was filled with a titanium n-butoxide solution prepared by dissolving 135 g titanium n-butoxide in 1600 ml toluene. This catalyst solution was circulated up-flow through the reactor at a flow rate of 15 ml/min at ambient temperature for 20 minutes, and then at 135° C. (275° F.) and 3.4 bar (35 psig) for 6 hours. After cooling, the excess catalyst solution was drained from the reactor and then the in situ-prepared catalyst was washed up-flow with toluene at ambient temperature at a flow rate of 4 ml/min for 1.5 hours. After draining excess toluene from the reactor, the catalyst was dried at 138° C. (280° F.) for 2 hours in 350 cc/min nitrogen gas up-flow. The resulting catalyst was used in a 1st cycle transesterification as follows.

Figure 7:
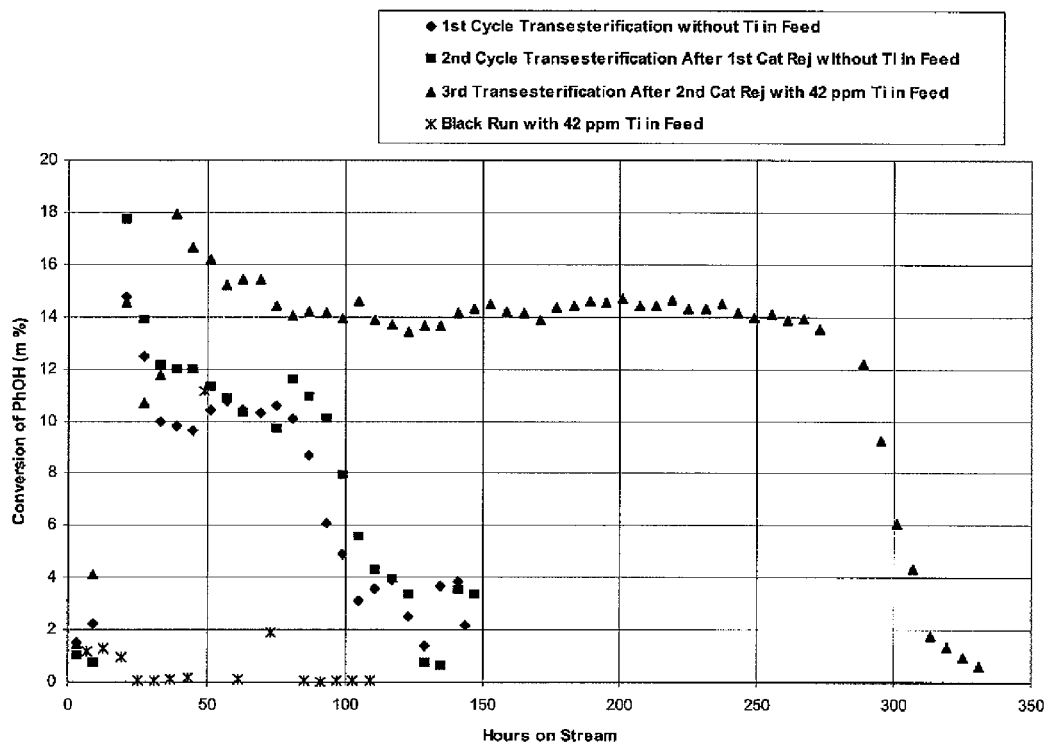
FIG. 7 graphically compares heterogeneous catalyst activity with solid catalyst activity when a trace amount of soluble organometallic compound is added to the reactor according to embodiments disclosed herein.

1st Cycle Transesterification: The 1st cycle transesterification was performed, without injecting soluble titanium species into the feed stream, under boiling reaction conditions of 168° C. (335° F.) and 2.4 bar (20 psig) with a feed rate of 0.2 ml/min up-flow. The feed composition was 26.07 wt % phenol and 73.93 wt % DEC (2.56 mole ratio of DEC/phenol). The result is illustrated in FIG. 7, The catalyst deactivated with on-stream time. After about 100 hours on stream, the catalyst had little activity.

1st Catalyst Reactivation: After draining material from the reactor, the catalyst in the reactor was washed with dried toluene 10 ml/min up-flow at ambient temperature for 1 hour and then excess toluene was drained from the reactor. The catalyst in the reactor was dried at 124° C. (255° F.) in nitrogen gas flowing at 250 cc/min up-flow for 1 hour. A mixed solution of water (4 wt %) and ethanol was passed though the reactor at 2.2 ml/min up-flow at 154° C. (310° F.) and ambient pressure for 6 hours. The catalyst was dried at 154° C. (310° F.) in 150 cc/min nitrogen up-flow for 1 hour 25 minutes. A titanium n-butoxide solution (67.5 g titanium n-butoxide in 800 ml toluene) was circulated through the reactor at 15 ml/min up-flow at room temperature for 20 minutes, and then at 134° C. (275° F.) and 3.4 bar (35 psig) for 6 hours. After cooling, the excess solution was drained from the reactor. The catalyst was washed with 4 ml/min toluene up-flow for 1.5 hours. The washed catalyst was dried at 138° C. (280° F.) in 300 cc/min nitrogen gas up-flow for 2 hours and used in a second cycle of the transesterification reaction.

2nd Cycle Transesterification: The reactivated catalyst was subject to the 2nd cycle transesterification with the same feed solution at identical conditions to the 1st cycle transesterification. The result is illustrated in FIG. 7. Similar results to the 1st cycle transesterification were obtained.

2 nd Catalyst Reactivation. The 2nd catalyst reactivation was performed in identical manner to the 1st catalyst reactivation.

3rd Cycle Transesterification. The reactivated catalyst obtained from the $2^{nd}$ catalyst reactivation was subject to a 3rd cycle of the transesterification with soluble titanium species added to the same feed solution at identical conditions to the 1st cycle transesterification. The results of the $3^{rd}$ cycle transesterification are illustrated in FIG. 7. A similar result to the 1st cycle transesterification was obtained, but the catalyst maintained a steady catalyst activity for an extended period of time. Trace analysis of a sample taken 270 hours on stream indicated 47 ppm Ti by weight. After the sample was taken at 270 hours on stream, the feed reservoir was refilled with a new feed. Unfortunately, the feed became turbid when it was blended with titanium n-butoxide. It is believed that the turbidity was caused by unexpectedly higher water content in feed solution than the previous feed solutions. The catalyst activity declined fast with this new feed solution. The trace analysis of the composite product with this new feed indicated 9 ppm Ti by weight. It was discovered that the water content in the feed stream should be kept at less than about 650 ppm by weight.

Blank Run (without performing immobilization of Ti alkoxide catalyst): The same reactor was loaded with 25 ml (9.54 g) silicon oxide pellet supports prepared by treating silicon oxide pellets with a sodium hydroxide solution (10 g NaOH in 570 ml water) at about 52° C. for 5 minutes with stirring. The silica was washed with cold water thoroughly and then with hot water (about 80° C.) to remove trace amounts of sodium on the silica. The treated silica was first dried at room temperature, then dried at 130° C. for 1.5 hours and then at 150° C. for 1 hour in a vacuum oven. A catalyst was not grafted to the support. The transesterification reaction was performed with 42 ppm Ti by weight in the same composition feed as above under identical conditions (under boiling reaction conditions of 168° C. (335° F.) and 2.4 bar (20 psig) with a feed rate of 0.2 ml/min up-flow, where the feed composition was 26.07 wt % phenol and 73.93 wt % DEC (2.56 mole ratio of DEC/phenol). The results are illustrated in FIG. 7. The conversion of phenol was less than 2% throughout the run.

This series of experiment (Experiment 5) successfully demonstrates that it is possible to reactivate deactivated catalyst and prolong the catalyst cycle time to more than 250 hours. The blank run clearly demonstrates that it is necessary to prepare the catalyst prior to performing transesterification. Alternatively, one may choose to initiate transesterification with a pre-prepared grafted titanium alkoxide catalyst outside the reactor. This experiment also indicates that it may be necessary to control water content in the feed to less than about 650 ppm by weight to maintain a steady catalyst activity.

Experiment 6

Figure 8:
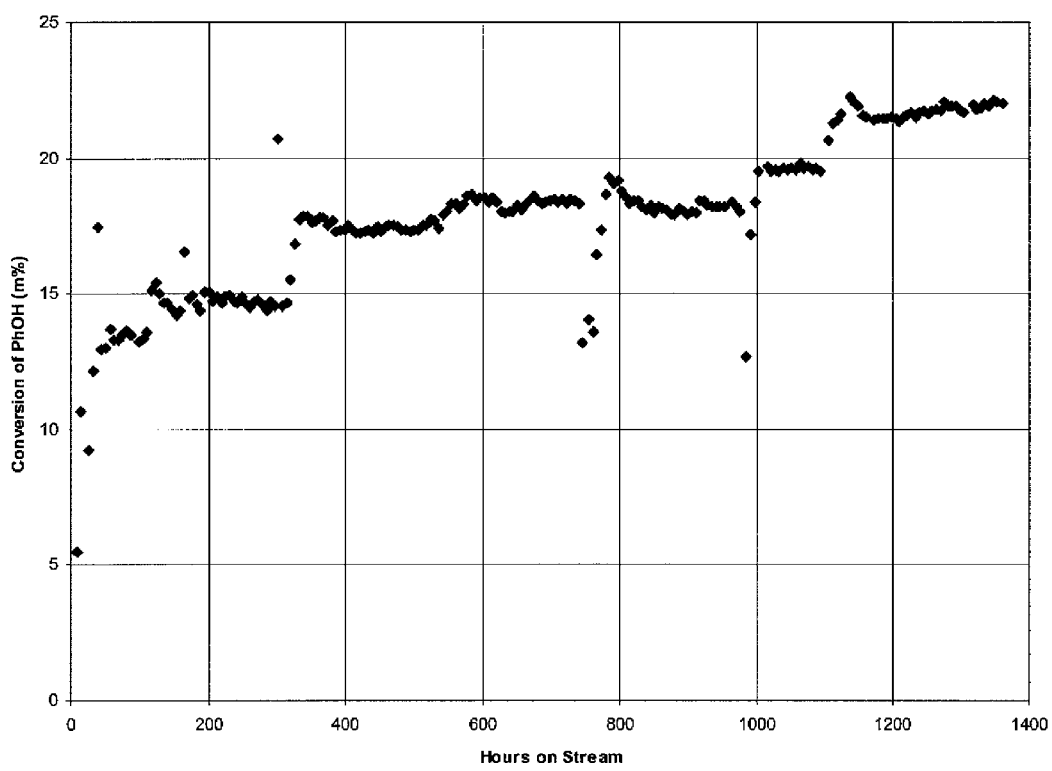
FIG. 8 is a graphical representation of solid catalyst activity when a trace amount of soluble organometallic compound is added to the reactor according to embodiments disclosed herein.

The objective of this experiment was to demonstrate continuous production of aromatic carbonates in a series of multiple reactors in the presence of a titanium oxide catalyst supported on a silica support. The same granular silica gel (40.7 g) in Experiment 3 was treated with a sodium hydroxide solution (6.86 g NaOH in 500 ml water) at ambient temperature for 7 minutes, with stirring. The silica gel was first washed with cold water thoroughly, and then with hot water (about 80° C.), to remove trace amounts of sodium on the silica. The treated silica gel was dried at 140° C. for 2 hours, at 345° C. for 3 hours, and then at 375° C. for 2 hors. 30 ml (10.99 g) was impregnated with titanium n-butoxide solution prepared by dissolving 4.71 g titanium n-butoxide in 80 ml dry toluene. The impregnated silica gel support was calcined at 500° C. for 3 hours. The titanium content on titanium oxide catalyst supported on silica was 5.48% Ti by weight based on the amount of titanium n-butoxide used. 25 ml (9.8 g) of titanium oxide catalyst supported on silica was loaded in the reactor. Transesterification of DEC with phenol was performed under various conditions. The feeds from 0 hour to 308 hours on stream time are two different mixtures of DEC and phenol. These feeds were used to perform the 1st transesterification of DEC with phenol. The titanium content in the DEC/PhOH feed solutions (from 0 to 308 hours on stream) was 59 ppm Ti by weight, prepared by blending a stock solution of $Ti(OEt)_{4-x}(OPh)_x$ (where x=~2). The stock solution of $Ti(OEt)_{4-x}(OPh)_x$ was prepared by distilling ethanol from a solution prepared by mixing an appropriate amount of titanium tetraethoxide in a mixed solution of DEC and phenol (PhOH) (25% wt) at from 120° C. to 125° C. for about 3 hours. The feeds from 308 hours to 986 hours on stream were prepared by distilling ethanol from the composite products of the 1st transesterification. These feeds were used to perform 2nd transesterifications, which are equivalent to the reactions in the second reactor in series or in some stages below the feed point of a multi-stage catalytic distillation column. The feeds from 986 hours to 1136 hours on stream were prepared by distilling ethanol from the composite products from 2nd transesterification. These feeds were used to perform 3rd transesterifications. No soluble titanium catalyst component was blended into the feeds for the 2nd or 3rd transesterification. The feed compositions are listed in Table 4. The transesterification was performed at 185° C. (365° F.), 2.9 bar (27 psig) and a feed rate of 0.24 ml/min. The result of this experiment is illustrated in FIG. 8. The conversion of phenol in FIG. 8 is the overall phenol conversion from the 1st transesterification through the 3rd transesterification. There was no indication of catalyst deactivation throughout the run (1362 hours continuous operation). The examination of the catalyst recovered from the reactor at the end of the run indicated little deposition of heavy polymers. The analysis of the catalyst indicated 2.3% Ti by weight, indicating about 58% loss of Ti due to leaching into the product stream. The trace analyses of Ti in the product streams taken at 686, 887 and 1293 hours on stream indicated 75, 57 and 78 ppm Ti by weight, respectively.

The result of this experiment clearly demonstrated the continuous production of aromatic carbonates by using a series of multiple reactors with long catalyst cycle time by adding a trace amount of a soluble Ti compound in the feed stream. Also, this experiment may suggest that large amounts of titanium oxide on a catalyst may not be necessary, as any excess amount of titanium oxide may be washed off by forming soluble organo titanium compounds. The catalyst cycle time is more than long enough for the time required for the catalyst reactivation. The combined selectivity of EPC and DPC was from about 98 mole % to about 93%, based on converted phenol and depending on the run conditions.

TABLE 4

| Time on Stream | DEC/PhOH mole ratio | | Product Stream wt. % | |
|---|---|---|---|---|
| (h) | in feed | EPC wt. % in feed | EPC | DPC |
| 0-86 | 2.2 | 0 | 5.5 | 0.14 |
| 86-308 | 2.4 | 0 | 5.7-6.2 | 0.19-0.20 |
| 308-746 | 1.71 | 5.86 ($1^{st}$ Transesterification) | 9.2-9.7 | 0.44-0.48 |
| 746-986 | 1.89 | 5.51 ($1^{st}$ Transesterification) | 8.8-9.4 | 0.44-0.47 |
| 986-1173 | 1.534 | 10.28 ($2^{nd}$ Transesterification) | 12-12.6 | 0.38-0.4 |
| 1173-1362 | 1.69 | 10.3 ($2^{nd}$ Transesterification) | 12.2-12.8 | 0.74-0.78 |

185° C. (365° F.), 2.9 bar (27 psig), 0.24 ml/min feed rate and 25 ml catalyst (9.8 g)

Experiment 7

The objective of this experiment was to demonstrate continuous production of aromatic carbonates in a series of multiple reactors by performing transesterification of DEC with phenol in the presence of a titanium ethoxide catalyst immobilized on a silica gel support.

This experiment consists of two parts; Experiment 7A and 7B. In Experiment 7A, immobilization of Ti ethoxide on a silica gel support was performed prior to performing transesterification. The feed contained various amounts of soluble $Ti(OEt)_{4-x}(OPh)_x$ (where x=~2) compound. In Experiment 7B, the 25 ml space in the reactor was loaded with 25 ml the silica gel support, and the transesterification was performed without grafting Ti tetra-ethoxide on the silica support.

Experiment 7A

The support used for in situ catalyst preparation was spherically shaped silica gel spheres (1.7-4 mm diameter). This silica gel support had about 6 hydroxyl groups per $nm^2$, 392 $m^2/g$ BET, 0.633 $cm^3/g$ pore volume, 6.48 m average pore diameter, and about 0.58 g/ml ABD. This silica gel support (25 ml; 14 46 g) was loaded in the reactor. A titanium ethoxide solution (45.25 g titanium ethoxide in 800 ml toluene) was circulated up-flow at 15 ml/min through the reactor at ambient temperature for 20 minutes and then at 135° C. (275° F.) under 3.4 bar (35 psig) for 6 hours to graft titanium ethoxide on silica gel support. After cooling, excess solution in the system was drained and then the catalyst was washed with toluene at 4 ml/min for 1.5 hours. The washed catalyst was dried at 138° C. (280° F.) for 2 hours in 300 cc/min nitrogen gas flow rate.

Figure 9A:
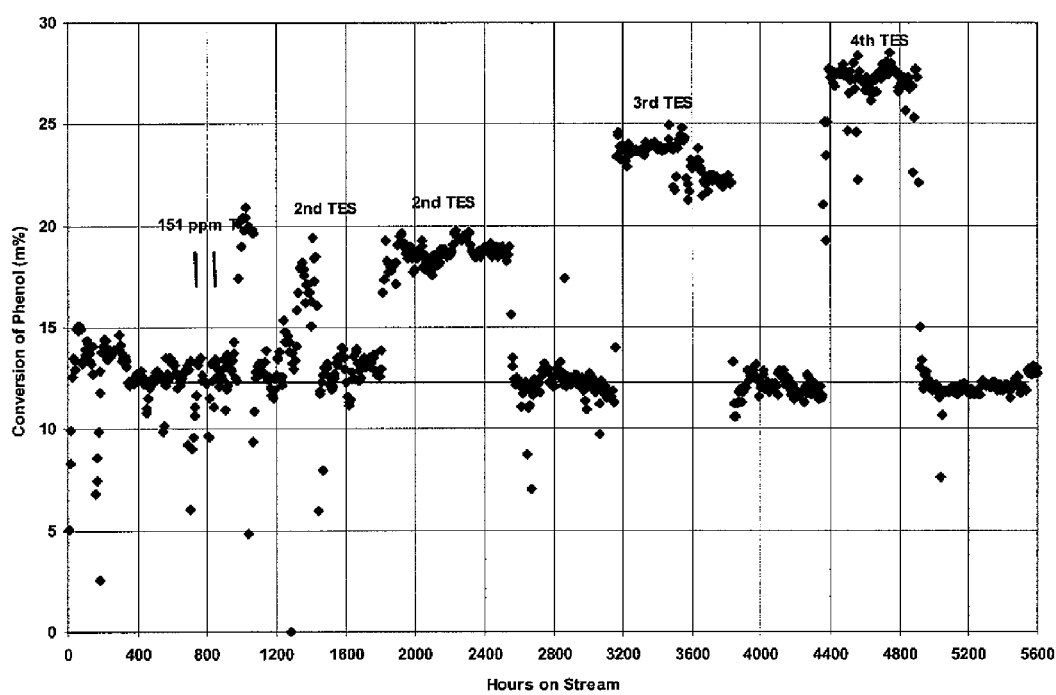
FIGS. 9A and 9B are a graphical representation of solid catalyst activity during production of EPC and DPC, respectively, when a trace amount of soluble organometallic compound is added to the reactor according to embodiments disclosed herein.
Figure 9B:
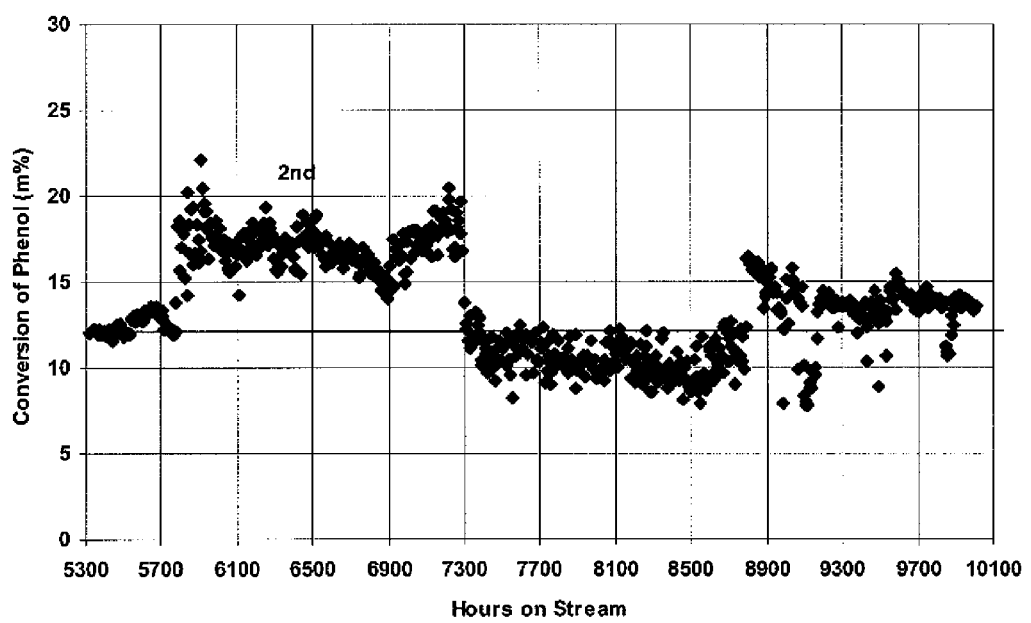

Reactions producing EPC and DPC were performed at various conditions. The result is illustrated in FIGS. 9A and 9B. All the first transesterification reactions were performed with 59 ppm Ti as Ti ethoxide added into feed stream, except the period of from 709 hours to 799 hours on stream, where 151 ppm Ti was added. The run started at 185° C. (365° F.), 2.9 bar (27 psig) and 0.24 ml/min for the first transesterification. After the first 50 hrs on stream, the temperature was slowly lowered to 174° C. (345° F.) and the feed rate was slowly increased to 0.5 ml/min over the next 96 hrs on stream. Thereafter, all the 1st and 2nd transesterification were performed at the condition of 174° C. (345° F.), 2.9 bar (27 psig) and 0.5 ml/min. By distilling ethanol from the composite products from the 1st, 2nd, and 3rd transesterifications, the feed mixtures were prepared for the 2nd, 3rd and 4th transesterifications. From 973 hrs to 1064 hrs on stream time, a mixed transesterification and disproportionation reaction was performed at 174° C. (345° F.) and 2.4 bar (20 psig), 0.5 ml/min feed rate. The composition of the feed for the reaction was 18.553% DEC, 0.108% ethylbutyl carbonate, 0.283% phenetole, 0182% unknown, 57.508% phenol, 22.03% EPC, 0.054% p-phenoxyphenyl methyl carbonate, and 1.282% DPC, on a weight basis. The result indicates that the major reaction is disproportionation. But the analysis of the data also suggests the need for removing DEC from the feed for disproportionation. In FIG. 9A, the 2nd transesterifications were performed at 174° C. (345° F.), 2.4 bar (20 psig) and 0.5 ml/min with the Ti concentration in the feed ranging from 44 ppm Ti to 69 ppm Ti by weight. In FIG. 9B, the 2nd transesterifications were performed at 174° C. (345° F.), 2.9 bar (27 psig) and 0.5 ml/min with the Ti concentration in feed ranging from 45 ppm Ti to 75 ppm Ti by weight. The 3rd transesterification was performed at 174° C. (345° F.), 2.5 bar (22 psig) and 0.5 ml/min with the Ti concentration in the feed ranging from 52 ppm Ti to 74 ppm Ti by weight. The 4th transesterification was performed at 174° C. (345° F.), 2.4 bar (20 psig) and 0.5 ml/min with the Ti concentration in the feed ranging from 51 ppm Ti to 73 ppm Ti by weight.

The selectivity of aromatic carbonates decreased with the conversion of phenol. The combined selectivity of EPC and DPC during the 1st transesterification is about 99 mole % based on phenol. The combined selectivity of EPC and DPC during the 4th transesterification was 94 mole to 95 mole % based on phenol.

The solid catalyst had been running over 14 months until termination of the experiment unrelated to catalyst activity. FIGS. 9A and 9B strongly suggest that there has been little to no catalyst deactivation for over 14 months. The analyses of the two catalyst samples taken carefully from the top and bottom of the catalyst bed indicate a same amount of 0.28 wt % Ti (550° C. calcined based) on the both catalyst samples.

This experiment successfully demonstrates that a long catalyst cycle (more than 14 months) can be obtained by adding a trace amount of soluble titanium compound into the feed stream.

Experiment 7B

Blank Run

The objective of this experiment was an attempt to immobilize Ti alkoxide on a silica support while performing the transesterification. Various amounts of soluble $Ti(OEt)_x(OPh)_{4-x}$ compound were added into the feed stream. The transesterification of DEC with phenol was performed at 174° C. (345° F.) and 2.9 bar (27 psig). The result is illustrated in FIG. 10.

Comparing the Blank in Experiment 5 (FIG. 7) and Experiment 7B (FIG. 10) with the result (FIGS. 9A and 9B), there is clear need for immobilizing titanium alkoxide on silica gel support prior to performing transesterifications. Comparing Comparative Experiments 1 and 2 (FIG. 4) with FIGS. 9A and 9B, the superiority of the novel solid catalyst technology, adding a trace amount of soluble active organometallic compound to the feed, over the prior art is also clearly demonstrated.

Experiment 8

The objective of this experiment was to demonstrate disproportionation of EPC to DPC and DEC in the absence of solid catalyst, but in the presence of soluble Ti catalytic components. The feeds for the disproportionation were prepared by distilling ethanol, DEC and a part of phenol from the composite products from the 4th transesterification in Experiment 7 under a nitrogen blanket. The homogeneous Ti catalyst in the feed mixtures was originated from the 4th transesterification composite products. No additional soluble Ti catalyst was added to the feed mixtures. Toluene was added to two feed mixtures to create a vapor phase for the boiling point reactor. The first feed composition was 16.26% toluene, 1.61% DEC, 49.33% phenol, 30.91% EPC and 0.78% DPC by weight and the balance was by-products including trace amounts of MPC. The second feed composition was 16.15% toluene, 1.61% DEC, 49.28% phenol, 31.08% EPC and 0.80% DPC by weight and the balance was by-products including trace amount of MPC. The concentration of homogeneous catalyst in the first and second feeds was 180 ppm and 200 ppm Ti by weight, respectively.

Figure 11:
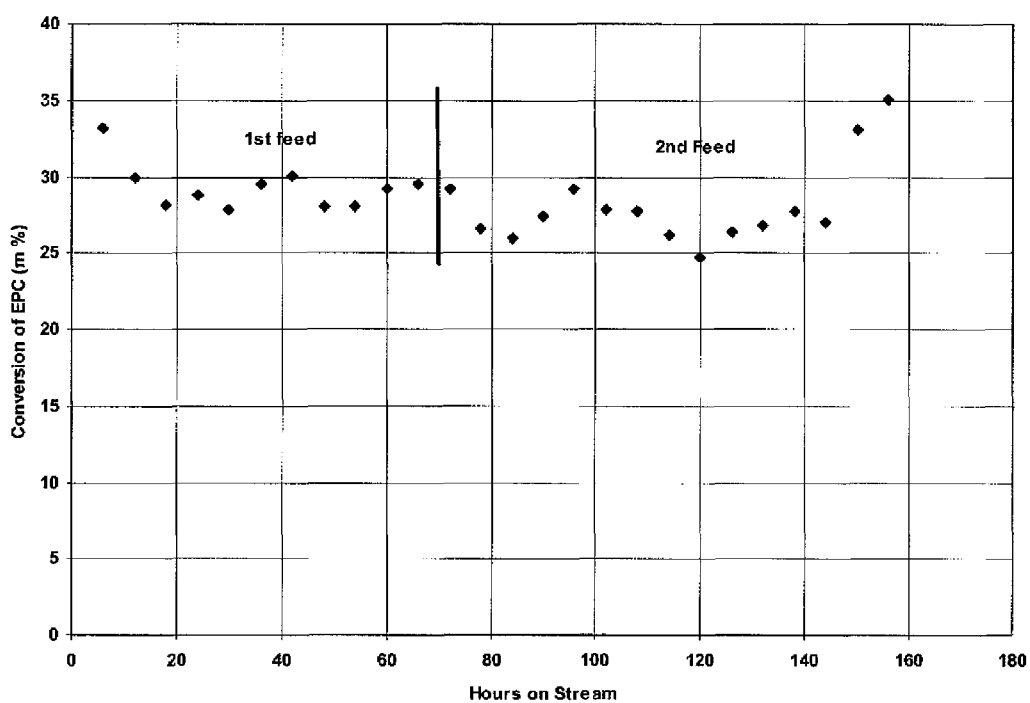
FIG. 11 graphically illustrates the conversion of EPC to DPC and DEC in the absence of solid catalysts according to embodiments disclosed herein.

The disproportionation was performed in the reactor with 25 ml empty catalyst space (in the absence of solid catalyst) at 179° C. (355° F.) and 2.9 bar (27 psig). The feed rates were 0.5 ml/min up-flow for the first 72 hours on stream and then 0.60 ml/min up-flow thereafter. The results of the disproportionation reactions are illustrated in FIG. 11. The experimental results indicate that small amounts of EPC are also produced in addition to DPC. Xanthone was the only new by-products produced during disproportionation in an amount of about 0.35 ppm by weight. Diphenyl ether was not detected in any sample analysis. The selectivity of all the by-products was from 3.0 mole % to 3.3 mole %. This experiment demonstrates successfully the EPC disproportionation to produce DPC and DEC according to embodiments disclosed herein.

Experiment 9

This experiment demonstrates the purification of DPC. A composite disproportionation product from Experiment 8 was distilled to remove ethanol, DEC and a substantial portion of phenol by using laboratory distillation equipments. The remaining material in the distillation flask had the following composition: 0.024% EtOH, 0.204% DEC, 0.017% phenetole, 1.619% unknowns, 12.563% phenol, 25.377% EPC, 59.474% DPC and 0.723% heavies. By performing vacuum distillation, crude DPC (cut at vapor temperature from 235 to 245° C.) was obtained. The composition of this crude DPC was 0.535% unknowns, 2.112% phenol, 0.013% phenyl ether, 0.030% EPC, 94.555% DPC, 0.026% xanthone and 2.73% heavies. This crude DPC was re-crystallized in a mixture of 5 wt % diethyl ether in hexane five times. The final DPC product had impurities of 0.4 ppm xanthone and 11.6 ppm phenol by weight. No other impurities were detected by trace analysis. This DPC product has a greater purity than high purity DPC available in the market (28.7 ppm unknowns and 67.2 ppm phenol by weight).

Dialkyl Carbonates by Transesterification of a Cyclic Carbonate with an Alcohol

Dialkyl carbonates are continuously produced by performing transesterification of a cyclic carbonate with alcohols in the presence of solid catalysts. As described above, embodiments disclosed herein may be particularly useful for continuous production of dialkyl carbonates, such as DMC, DEC, etc. There are a number of homogeneous catalysts for transesterification. When dialkyl carbonates are produced by performing transesterification of a cyclic carbonate with an alcohol in the presence of supported metal oxide or mixed metal oxide catalysts or a solid catalyst prepared by immobilizing a homogeneous catalyst on a porous support, the catalysts have unacceptably short cycle length for operation of large commercial reactors. The permanent catalyst deactivations involved in dealing with organic carbonates are caused by leaching active catalytic components out of heterogeneous catalysts into the reaction medium. Therefore, dialkyl carbonate such as DMC is commonly produced by performing transesterification in the presence of a homogeneous catalyst.

Embodiments disclosed herein, however, offer processes for producing dialkyl carbonate in the presence of a solid catalyst. Solid catalysts may include one or more elements from Groups II, III, IV, V and VI of the Periodic Table. A first type of solid catalyst includes one or more organometallic compounds of the above elements immobilized on a porous support, which may have surface functional groups such as hydroxyl, carbonyl, alkoxy, a mixture of hydroxyl and alkoxy, chlorine, etc. Supports may include silica, titanium oxide, zeolitic materials such as MCM-41, MCM-48, SBA-15, carbon and/or carbonaceous materials, etc. A second type of solid catalyst includes metal oxides, hydroxides or oxyhydroxides of one or more of the above elements deposited on a porous support. To maintain a stable catalyst activity, a trace amount of a soluble catalytic component is added to the feed stream. By doing so, the catalyst cycle length can be extended to be suitable for commercial reactor.

The transesterification may be performed in any physical devices, such as traditional fixed bed reactors, catalytic distillation columns, boiling point reactors, divided wall distillation columns, pulsed flow reactors, or any combination of these devices. Examples of a combination may include a fixed bed boiling point reactor followed by a catalytic distillation column reactor. Transesterification of cyclic carbonates with a primary alcohol, such as ethanol or methanol, may be carried out as a two-step reaction, where there are two ethyl propylene glycol carbonate intermediates. Also the reaction product contains small amounts of by-products, such as propylene glycol ethyl ether isomers, produced by O-alkylation of propylene glycol by DEC. The transesterification may be performed in a single reaction zone or multiple reaction zone.

Figure 18:
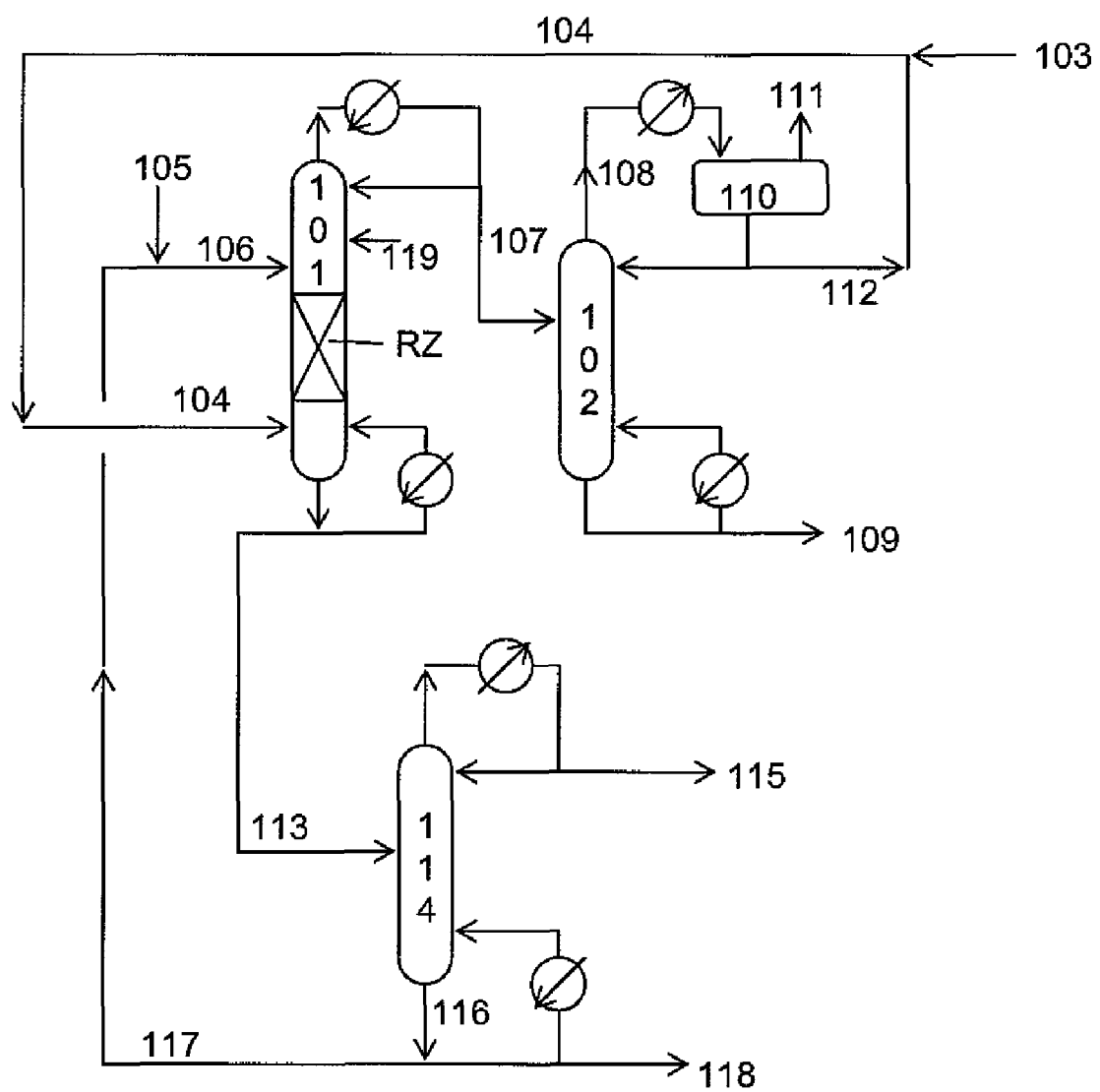
FIG. 18 is a simplified process flow diagram for the continuous production of DEC and propylene glycol co-product by performing alcoholysis of propylene carbonate with ethanol in the presence of a solid catalyst according to embodiments disclosed herein.

FIG. 18 illustrates a simplified process flow diagram for the continuous production of DEC and propylene glycol co-product by performing transesterification of propylene carbonate with ethanol in the presence of a solid catalyst according to embodiments disclosed herein. The transesterification, as illustrated, may be performed in a catalytic distillation reactor 101 at a temperature from about 149° C. to about 0.177° C. (about 300° F. to 350° F.) under a pressure from about 2 bar to about 11.4 bar (about 45 psig to 150 psig) depending on the composition of reaction mixture. In addition to catalytic distillation reactor 101, the process includes two distillation columns, 102 and 114. Catalytic distillation column 101 includes a reaction zone RZ, in which a solid catalyst may be located. Fresh propylene carbonate feed 105 is combined with recycle stream 117 and the combined stream 106 is introduced into the catalytic distillation column 101 at a suitable position above the solid catalyst bed reaction zone RZ.

Column 101 overheads stream 107, a mixture of ethanol, DEC and lights, such as carbon dioxide, is introduced to DEC recovery column 102, for the separation of DEC from lighter components. Column 102 overheads stream 108 may be introduced into gas-liquid separation drum 110 to separate liquid ethanol from gases vented through line 111. The liquid ethanol recovered from drum 110 in stream 112 is combined with the fresh ethanol feed stream 103 and the combined stream 104 is heated to produce ethanol vapor introduced to catalyst distillation column 101 at suitable position below reaction zone RZ. Distillation column 102 bottoms stream 109 contains the product, DEC, which may be sent to a storage tank (not shown) or other downstream processes.

Bottom stream 113 from the catalytic distillation column 101, which contains propylene glycol, propylene carbonate, reaction intermediates and by-products such as 1-ethoxy-2-propanol, heavies, etc. and a trace amount of catalyst, are introduced to the second distillation column 114 to recover an overhead stream 115 containing propylene glycol, 1-ethoxy-2-propanol, etc. Propylene glycol may be recovered from the mixture in stream 115 by distillation (not shown). Column 114 bottoms stream 116 is recycled to the catalytic distillation column 101 through lines 117 and 106. A portion of bottoms steam 116 may be purged from the system via stream 118 to prevent build-up of heavies in the system.

A trace amount of soluble organometallic compound is introduced to the catalytic distillation column 101 above catalytic reaction zone through line 119. In some embodiments the catalyst solution is fed at a rate such that the liquid reaction mixture flowing down the catalytic reaction zone RZ contains a trace amount, typically from 5 ppm to about 100 ppm metal by weight, of soluble metallic component, such as Mg, Ca, Zn, La, Ac, or Ti compounds.

The production of dialkyl carbonates is illustrated by the following experiments.

Experiment 10

The objective of this experiment was to demonstrate the transesterification of propylene carbonate with ethanol to produce DEC and propylene glycol in the presence of a solid catalyst. The solid catalyst is prepared in situ by immobilizing titanium ethoxide on a silica gel support.

The reactor was loaded with 25 ml (1.7-4 mm diameter) of a spherical silica gel support. The weight of the support was 10.097 g. This silica gel support had about 6 hydroxyl groups per $nm^2$, 314 $m^2/g$ BET, 1.055 $cm^3/g$ pore volume and 13.46 nm average pore diameter. A titanium ethoxide solution (40 g titanium ethoxide in 800 ml toluene) was circulated up-flow through the reactor at 15 ml/min at ambient temperature for 30 minutes and then at 135° C. (275° F.) and 3.4 bar (35 psig) for 6 hours to graft titanium ethoxide on the silica gel support. After cooling, excess solution was drained from the reactor and then the catalyst was washed with toluene at 4 ml/min for 1.5 hours. The washed catalyst was dried at 138° C. (280° F.) for 2 hours in 300 cc/min nitrogen gas flow.

Figure 12:
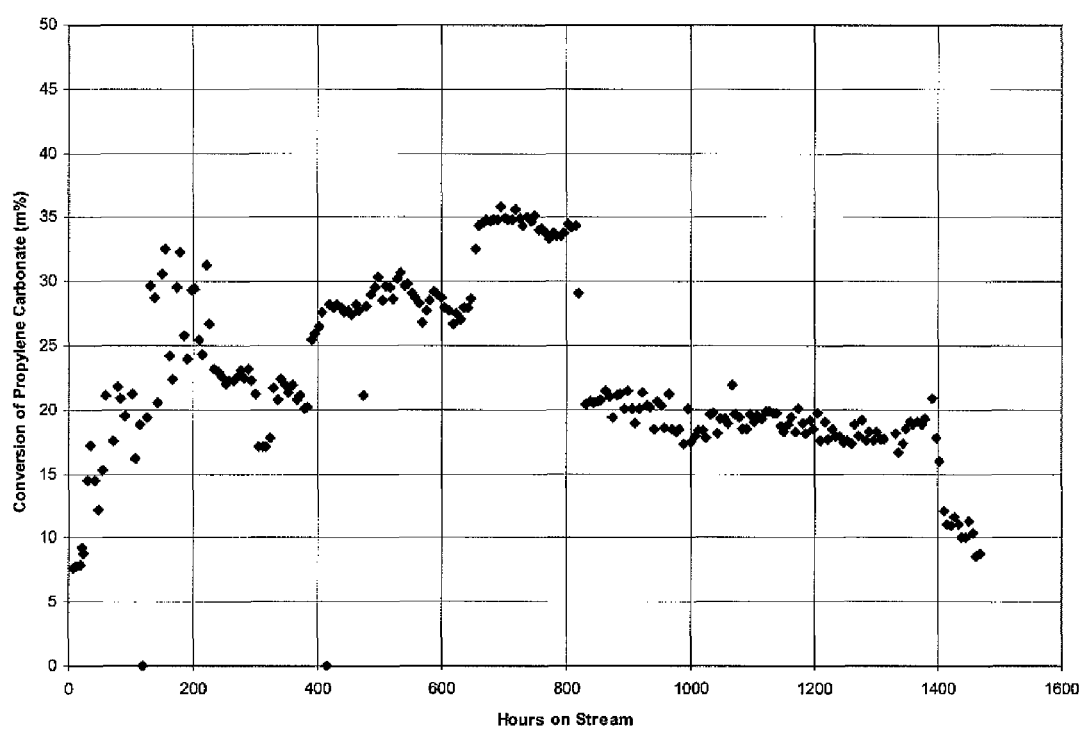
FIG. 12 graphically presents results from the alcoholysis of propylene carbonate with ethanol to produce DEC and propylene glycol in the presence of a solid catalyst according to embodiments disclosed herein.

Mixed solutions of propylene carbonate and ethanol were prepared and 45 ppm Ti as titanium ethoxide was blended into the mixed feed solutions. Transesterifications were performed with various feed mixtures in up-flow liquid phase at 174° C. (345° F.) and 17.9 bar (245 psig). The run conditions are listed in Table 5. The results of this experiment are illustrated in FIG. 12.

TABLE 5

| Time on Stream (h) | EtOH/PC mole ratio in feed | Feed Rate (ml/min) | Ti in Feed (wt. ppm) | Note |
| --- | --- | --- | --- | --- |
| 0-24 | 0.64 | 0.3 | 45 | $1^{st}$ Transesterification |
| 24-90 | 6.64 | 0.4 | 45 | $1^{st}$ Transesterification |
| 90-120 | 5.23 | 0.4 | 45 | $1^{st}$ Transesterification |
| 120-143 | 4.89 | 0.4 | 45 | $1^{st}$ Transesterification |
| 143-167 | 3.67 | 0.4 | 45 | $1^{st}$ Transesterification |
| 167-215 | 6.41 | 0.4 | 45 | $1^{st}$ Transesterification |
| 215-287 | 5.52 | 0.4 | 45 | $1^{st}$ Transesterification |
| 287-335 | 5.52 | 0.5 | 45 | $1^{st}$ Transesterification |
| 335-383 | 6.76 | 0.5 | 45 | $1^{st}$ Transesterification |
| 383-647 | 6.9 | 0.5 | 89 | $2^{nd}$ Transesterification |
| 647-815 | 6.3 | 0.5 | 90 | $3^{rd}$ Transesterification |
| 815-887 | 6.41 | 0.5 | 45 | $1^{st}$ Transesterification |
| 887-893 | 4.95 | 0.5 | 45 | $1^{st}$ Transesterification |
| 893-1055 | 6.03 | 0.5 | 45 | $1^{st}$ Transesterification |
| 1055-1151 | 6.2 | 0.5 | 45 | $1^{st}$ Transesterification |
| 1151-1223 | 4.13 | 0.5 | 45 | $1^{st}$ Transesterification |
| 1223-1313 | 4.72 | 0.5 | 45 | $1^{st}$ Transesterification |
| 1313-1397 | 3.65 | 0.5 | 45 | $1^{st}$ Transesterification |
| 1397-1469 | 5.27 | 0.5 | 0 | $1^{st}$ Transesterification |

The results of this experiment clearly demonstrate that DEC (a dialkyl carbonate) may be produced by performing transesterification of a cyclic carbonate such as propylene carbonate with ethanol in the presence of solid Ti alkoxide catalyst immobilized on a silica gel support by adding a trace amount of a soluble Ti compound into the feed stream. Without addition of a trace amount of Ti in feed stream, the catalyst activity declines rapidly as shown in FIG. 12 over run hours 1397-1469.

Experiment 11

The objective of this experiment is to demonstrate transesterification of propylene carbonate with ethanol to produce DEC and propylene glycol in the presence of a solid catalyst. The experiment consists of two parts; Comparative Experiments 11A (non-invention) and 11B.

Comparative Experiment 11A

Figure 13:
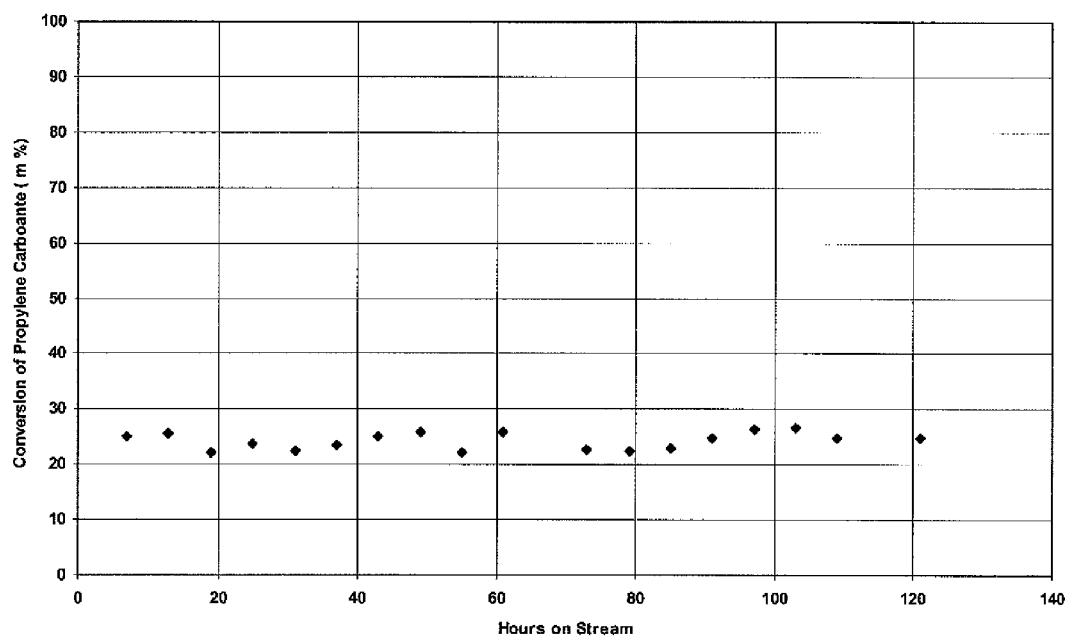
FIG. 13 presents results from the production of DEC using a homogeneous catalyst.

The transesterification was performed in the presence of a homogenous magnesium tert-butoxide. The mole ratio of ethanol/propylene carbonate of the feed mixture was 6.85. The concentration of homogeneous catalyst was 57 ppm Mg by weight. The transesterification was performed at 168° C. (335° F.), 17.9 bar (245 psig) and 0.5 ml/min. The result is illustrated in FIG. 13. The average conversion of propylene carbonate is about 24.3 mole %. The average selectivity of DEC and propylene glycol are 95.7 and 94.3 mole %, respectively.

Experiment 11B

The transesterification was performed in the presence of a solid catalyst. The starting solid catalyst was MgO supported on a silica gel support. A magnesium nitrate solution was prepared by dissolving 10.098 g of $Mg(NO_3)_2 \cdot 6H_2O$ in 22.73 g deionized water by incipient impregnation. Magnesium nitrate was deposited on 30 ml (11.777 g) of the same silica gel support used in Experiment 10 by incipient impregnation. The impregnation product was dried at 100° C. in vacuum oven for one hour, followed by calcinations at 51° C. for 2 hours to prepare MgO supported on silica gel. 25 ml (10.77 g) of this surface mixed oxide catalyst of MgO and silica gel was loaded in the reactor. Transesterification of propylene carbonate with ethanol was performed at the various conditions listed in Table 6.

TABLE 6

| Time on Stream (h) | EtOH/PC mole ratio in feed | Feed Rate (ml/min) | Mg in Feed (wt. ppm) | Note |
|---|---|---|---|---|
| 0-79 | 6.96 | 0.5 | 111 | $1^{st}$ Transesterification |
| 79-175 | 10.12 | 0.5 | 111 | $1^{st}$ Transesterification |
| 175-341 | 6.95 | 0.5 | 56 | $1^{st}$ Transesterification |
| 341-413 | 6.89 | 0.5 | 34.8 | $1^{st}$ Transesterification |
| 413-485 | 7.17 | 0.5 | 42.8 | $1^{st}$ Transesterification |
| 485-570 | 3.41 | 0.5 | 41.5 | $1^{st}$ Transesterification |
| 570-666 | 4.14 | 0.5 | 34.5 | $1^{st}$ Transesterification |
| 666-738 | 5.39 | 0.5 | 34.5 | $1^{st}$ Transesterification |
| 738-834 | 6.59 | 0.5 | 37.5 | $2^{nd}$ Transesterification |

Figure 14:
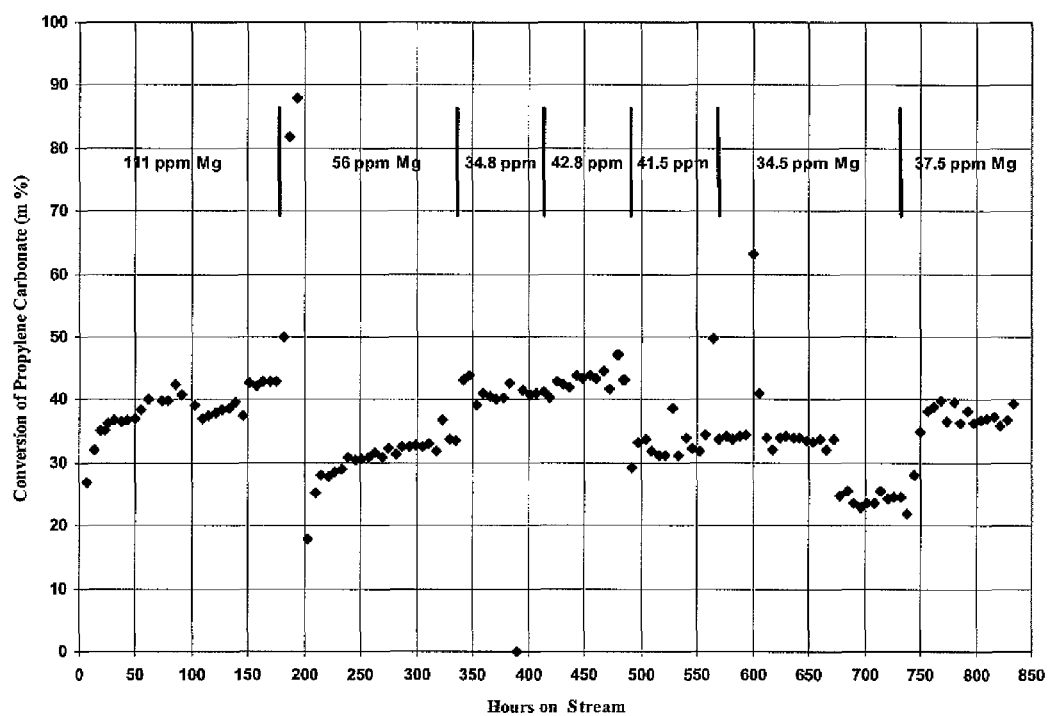
FIG. 14 presents results from the production of DEC using a solid catalyst according to embodiments disclosed herein.

The reaction products contained 1-ethoxy-2-propanol and dipropylene glycol as by-product. No diethyl ether was detected in any product sample. The result is also illustrated in FIG. 14. The average selectivity of DEC and propylene glycol for the 1st transesterification are 95.3 mole % and 94.8 mole %, respectively. In general, the selectivity declines slowly with conversion of propylene carbonate. Also selectivity increases with the mole ratio of EtOH/propylene carbonate. The average selectivity of DEC and propylene glycol for the 2nd transesterification are 94.0 mole % and 92.8 mole %, respectively.

Dialkyl Carbonates from Urea and an Alcohol According to Embodiments Disclosed Herein According to publications such as P. Ball et al and D. Wang et al., as referenced above, heterogeneous catalysts useful for the production of dialkyl carbonates from urea and an alcohol may include $Al_2O_3$, $Sb_2O_3$, and silica. Fused $SiO_2$ is not a catalyst, but may become catalytic in the presence of $PPh_3$. ZnO and MgO supported on silica may also be used to produce dialkyl carbonates from urea and an alcohol.

However, metal oxide catalysts such as ZnO or MgO leach out of solid catalysts under reaction condition, resulting in permanent catalyst deactivation. Catalyst cycle length is very important in commercial production of dialkyl carbonates using a catalytic distillation column reactor, as catalytic distillation provides for fast removal of DMC or DEC and ammonia from the liquid catalytic reaction medium, improving the dialkyl carbonate productivity and selectivity. Additionally, the above described heterogeneous catalysts are not as effective as homogeneous dibutyltin dimethoxide catalyst.

According to embodiments disclosed herein, dialkyl carbonates may be continuously produced by causing the alcoholysis of urea with an alcohol in two steps in the presence of a solid catalyst. Both reaction steps are equilibrium reactions. Examples of alcohols used to produce the dialkyl carbonates include methanol, ethanol, propanol, etc. In the first step of the reaction, urea is reacted with an alcohol in a reactive distillation column (pre-reactor), serving as the first reaction zone, in either the absence or presence of a catalyst to produce alkyl carbamate and ammonia. Catalyst is not necessary for the first step reaction. Impurities in feed streams such as water and ammonium carbamate are removed as $CO_2$ and ammonia in the first reaction zone as well, protecting downstream catalysts. In the second step reaction, alkyl carbamate produced in the first reaction zone is reacted with alcohol to produce dialkyl carbonate and ammonia in the presence of a solid catalyst in one or more catalytic distillation columns primary reactors), which are serving as the second reaction zone. The two step reaction may be illustrated as follows:

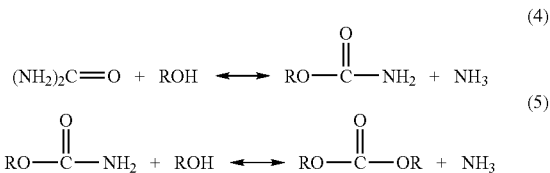

The solid catalyst may be prepared by immobilizing organo tin compound, organo antimony compound, etc. on a support such as silica or carbonaceous material. The examples of tin and antimony compounds are alkyltin alkoxides, tin alkoxides, antimony alkoxides, etc. Other types of solid catalyst are tin oxide or antimony oxide supported on a support. There are two types of catalysts at the beginning of the reaction. The first type of catalyst is metal alkoxide, a metal salt of a carbonic acid monoester, or a mixture of these, immobilized on a support such as silica or carbonaceous material. The second type of the catalyst is metal oxide supported on a support such as silica, alumina, titania, zirconia, carbonaceous material, etc. Active metal components may be elements such as Sn, Sb, Ti, Zr, Zn, Mg, Ca, etc.

Again, a small amount of a soluble metal compound is added to the reaction stream going into the reactor to maintain catalyst activity over an extended cycle length. By doing so, the catalyst cycle length can be extended to be suitable for use in commercial processes. It is believed that the working catalyst under the steady state condition is a metal alkoxide, metal alkoxy alkyl carbonate (salt of carbonic acid monoester, or oligomers or mixtures of these, immobilized on a support. The concentration of soluble organometallic compound, such as dibutyltin dialkoxide, in the reaction mixture is significantly lower than the homogeneous catalyst used in U.S. Pat. No. 7,074,951.

A high boiling solvent, such as triglyme, may be used as a solvent in the second step, and serves as a co-catalyst to improve reaction rate and selectivity. Importantly, because of the high boiling point of the solvent, the reaction can be carried out under low pressure, which aids in fast removal of DEC and ammonia from the liquid reaction medium into the vapor phase along with excess ethanol vapor as stripping gas, resulting in high DEC productivity and selectivity. Embodiments disclosed herein offer an alternative improved process for producing dialkyl carbonate in the presence of a solid catalyst. This process may be a "greener" process, because the concentration of tin catalyst in the process stream is substantially reduced. The trace amount of soluble catalytic compound in the process stream stays in the system. No recovery or separation of soluble catalyst compound in the process stream is necessary.

Figure 15:
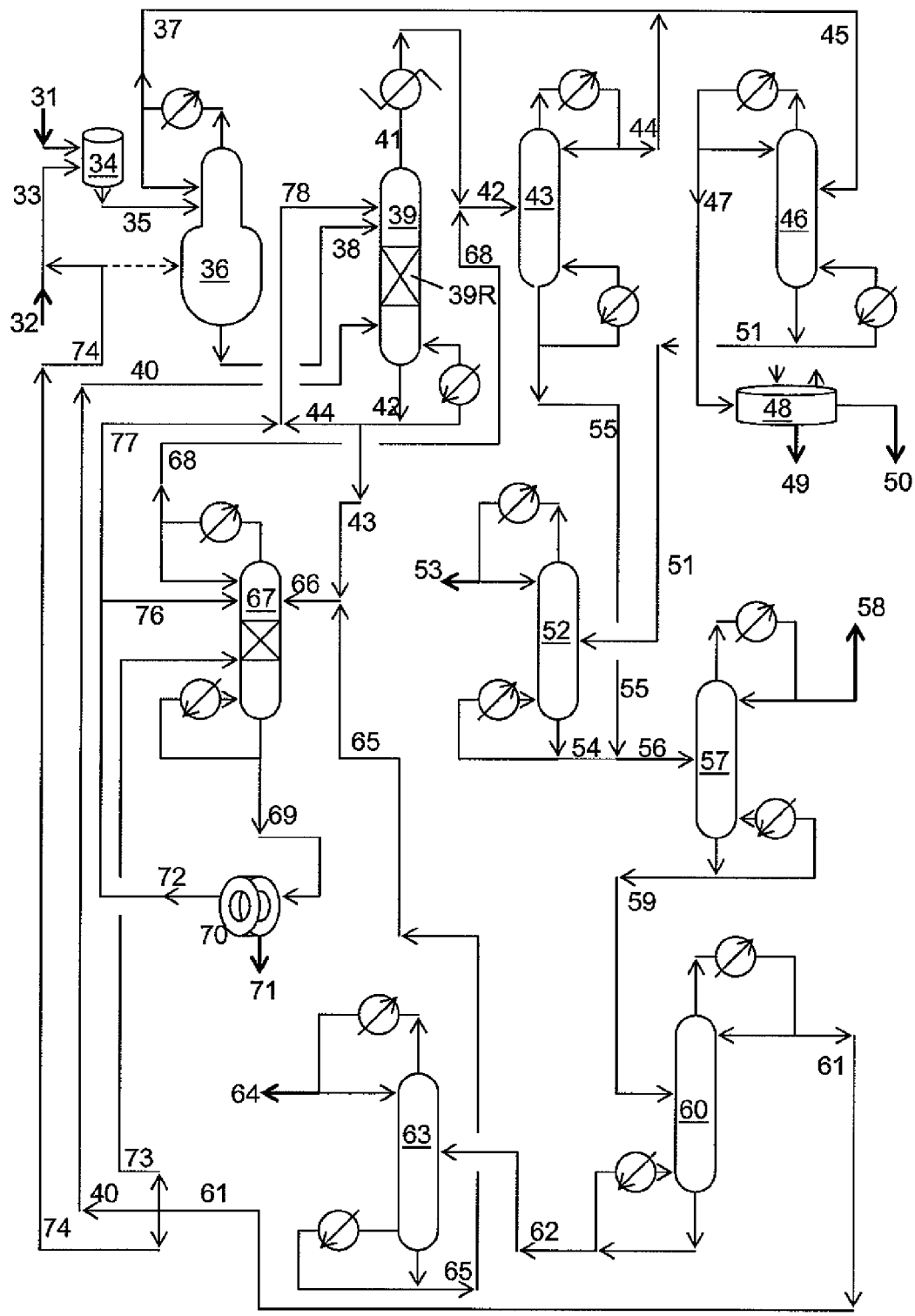
FIG. 15 is a simplified process flow diagram for the production of dialkyl carbonates using a solid catalyst according to embodiments disclosed herein.

FIG. 15 illustrates a flow diagram of the process for the continuous production of DEC according to embodiments disclosed herein. A double diameter distillation column reactor 36 is used as the pre-reactor to remove impurities in the feed streams and for the conversion of urea to ethyl carbamate (EC). Urea solution is prepared in drum 34 by mixing urea feed 31 and ethanol stream 33. Ethanol stream 33 may include fresh ethanol feed 32 and ethanol from recycle stream 74.

The urea solution 35 from drum 34 is introduced to the middle of an upper narrower column section of the double diameter tower reactor 36. Reactor 36 serves as a pre-reactor to clean up the impurities (water and ammonium carbamate) in the feeds, ethanol and urea, and to convert urea to EC. Vapor stream 37 from pre-reactor 36 is composed of ammonia, carbon dioxide and ethanol. The cleaned mixed solution is removed from pre-reactor 36 as bottom stream 38. Stream 38 is introduced to primary reactor 39 (catalytic distillation column) at a position above a catalytic reaction zone 39R containing a solid catalyst.

Recycle ethanol stream 40 is introduced into reactor 39 as superheated ethanol vapor at a position below the catalytic reaction zone 39R. The bottom stream from the catalytic distillation column 39 is recycled to a position above the feed point of line 38 at the top of column 39 through lines 42, 44 and 78. A small slipstream 43 from the recycle loop is combined with bottom stream 65 from DEC recovery column 63 to stream 66, which is introduced to clean-up reactor 67 at a position above catalytic reaction zone, which is another small catalytic distillation column containing a solid catalyst. Slipstream 43 may include ethanol, ammonia, ethyl amine, diethyl ether, DEC, ethyl carbamate, N-ethyl ethyl carbamate, triglyme (TG), heavies and a trace amount of soluble catalyst component. The bottom stream 65 from DEC recovery column 63 may include ethyl carbamate, N-ethyl ethyl carbamate, TG, and a trace amount of catalyst. The overhead stream 68 from clean-up reactor 67 may include ammonia, ethyl amine, $CO_2$, diethyl ether, ethanol, and DEC. Bottom stream 69 from clan-up reactor 67 may include ammonia, ethyl amine, $CO_2$, diethyl ether, ethanol, N-ethyl ethyl carbamate, ethyl carbamate, heterocyclic compounds and a trace amount of soluble catalyst component.

Bottom stream 69 from reactor 67 is cooled to precipitate heterocyclic compounds in the cooling/filter system 70. The precipitated solid by-product is removed from system 70 through line 71. Liquid stream 72 from system 70 splits to two streams 77 and 78 to recycle to clean-up reactor 67 and primary reactor 39, respectively.

Overhead stream 41 from primary reactor 39 may be combined with overhead stream 68 from clean-up reactor 67 to stream 42. Overhead stream 41 from primary reactor 39 may include ammonia, $CO_2$, ethyl amine, diethyl ether, ethanol, ethyl carbamate, N-ethyl ethyl carbamate, DEC, TG and trace amount of catalyst. Combined stream 42 is introduced to distillation column 43, where lights and heavier compounds are separated. Overhead stream 44 from distillation column 43, which may include ammonia, $CO_2$, ethylamine, diethyl ether and ethanol, is combined with overhead stream 37 from pre-reactor 36 to stream 45 to introduce to distillation column 46.

Overhead stream 47 from distillation column 46 is cooled to cause the reaction of $CO_2$ with ammonia to form ammonium carbamate, Ammonium carbamate is precipitated in liquid ammonia and removed as solids through line 49 from cooling/filter system 48. Liquid ammonia stream 50 from cooling/filter system 48 is sent to an ammonia storage tank.

Bottom stream 51 from column 46 may include ethylamine, diethyl ether, ethanol and a trace of DEC. Stream 51 is introduced to ethylamine recovery column 52. Overhead ethylamine stream 53 is sent to a storage tank. Bottom stream 54 from column 52 is combined with bottom stream 55 from distillation column 43 to stream 56. Stream 56 is introduced to ether recovery column 57. Ether is removed from distillation column 57 as overhead stream 58, which is sent to an ether storage tank. Bottom stream 59 from distillation column 57 is introduced distillation column 60 (ethanol recovery column).

Recovered ethanol as overhead stream 61 is recycled to primary reactor 39, clean-up reactor 67 and pre-reactor 36 (or drum 34). The ethanol recycle stream 74 is a minor portion of the overhead stream 61 of distillation column 60 (ethanol recovery column). Stream 61 splits to three streams, 40, 73 and 74. Stream 73 is recycled to clean-up reactor 67. Stream 74 is recycled to drum 34 for preparation of urea solution. Stream 40, which may be a major portion of stream 61, is recycled to primary reactor 39. Bottom stream 62 from ethanol recovery column 60 is introduced to DEC recovery column 63. Product DEC is recovered as overhead stream 64 from distillation column 63 and sent to a DEC storage tank. The bottom stream 65 from column 63 may include ethyl carbamate, N-ethyl ethyl carbamate, TG and a trace amount of soluble catalyst component. This stream 65 is sent to clean-up reactor 67 via line 66.

DMC can be produced from methanol and urea in a process similar to the process for producing DEC as described with respect to FIG. 15. However, it is understood that the final product DMC is recovered from a process stream having a methanol-DMC azeotrope. Recovery of DMC by breaking a methanol-DMC azeotrope by a solvent extractive distillation technique is well documented, such as described in U.S. Pat. No. 7,074,951.

Experiment 12

The objective of this experiment is to demonstrate the reaction of ethyl carbamate with ethanol to produce DEC and ammonia in the presence of a solid catalyst. The solid catalyst was prepared by immobilizing dibutyltin dimethoxide on a silica gel by in situ technique.

25 ml (14.79 g) of spherically shaped silica gel support used in the Experiment 7A was loaded in the reactor. A dibutyltin dimethoxide solution was prepared by mixing 87 g dibutyltin dimethoxide in 2 liters of dry toluene. The reactor was filled with this solution up-flow at ambient temperature and pressure. The reactor was heated slowly to 110° C. (230° F.) while flowing this solution up-flow at 2 ml/min. At 110° C. (230° F.), the reactor was placed under 3.4 bar (35 psig) and then continued to heat to 135° C. (275° F.). At 135° C. (275° F.) and 3.4 bar (35 psig), the dibutyltin dimethoxide solution was passed through the reactor up-flow at 0.5 ml/min for 6 hours. After cooling, excess solution in the reactor was drained and then the catalyst was washed with dry toluene at 4 ml/min up-flow for 1.5 hours. The washed catalyst was dried at 104° C. (220° F.) under ambient pressure in 300 cc/min $N_2$ flow down-flow for 2 hours.

Figure 16:
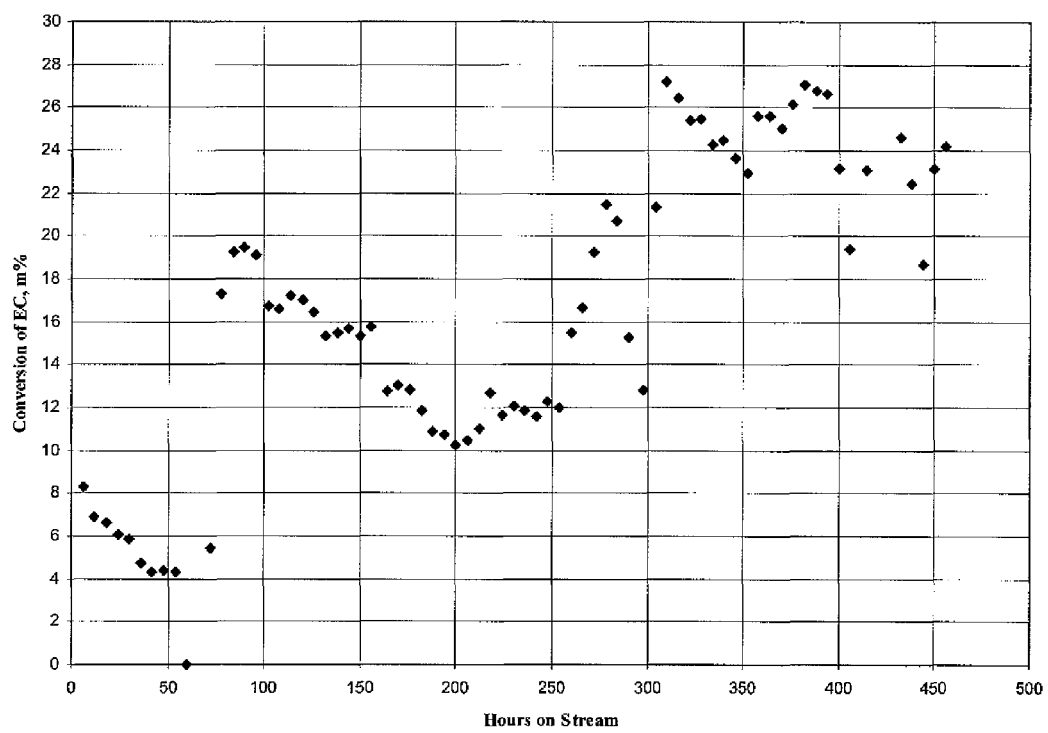
FIG. 16 presents results from the production of DEC from ethyl carbamate using a solid catalyst according to embodiments disclosed herein.

The reaction was performed by passing a solution of 13.2% ethyl carbamate, 31.36% triglyme and 55.44% ethanol by weight up-flow with nitrogen gas through the solid catalyst bed in the boiling point reactor. One may also carry out the reaction in down-flow reactor. Trace amounts of dibutyltin dimethoxide were blended into this solution. The reaction conditions are listed in Table 7 and the results of this test are illustrated in FIG. 16. Analyses of the reaction products indicated trace amounts of N-ethyl ethyl carbamate and diethyl ether. The selectivity of DEC based on ethyl carbamate was in a range of from 98.5 mole % to 99.9 mole % with a general trend of decreasing selectivity as conversion of ethyl carbamate increases.

TABLE 7

| Time on Stream (h) | Temperature, °C. (°F.) | Pressure, bar (psig) | Feed Rate (ml/min) | N₂ Flow Rate (cc/min) | Dibutyl Tin Dimethoxide (ppm Sn by weight) |
|---|---|---|---|---|---|
| 0-72 | 174 (345) | 6.2 (75) | 0.5 | 1.5 | 650 |
| 72-96 | 174 (345) | 6.2 (75) | 0.5 | 1.5 | 1300 |
| 96-156 | 174 (345) | 6.2 (75) | 0.5 | 1.8 | 1300 |
| 156-254 | 174 (345) | 6.2 (75) | 0.5 | 1.5 | 1950 |
| 254-298 | 174 (345) | 5.4 (63) | 0.5 | 0 | 1950 |
| 298-406 | 174 (345) | 5.4 (63) | 0.5 | 1.0 | 1950 |
| 406-456 | 174 (345) | 5.4 (63) | 0.5 | 1.5 | 1950 |

This experiment successfully demonstrates that DEC may be produced from urea and ethanol. In the first step, ethyl carbamate was produced by reacting urea with ethanol in the absence of a catalyst (see U.S. Pat. No. 7,074,951). In the second step, DEC was produced by performing the reaction of ethyl carbamate with ethanol in the presence of a solid catalyst and with addition of a trace amount of soluble organometallic compound to the feed streams to counter balance the loss of metal due to leaching. The commercial production of DEC in the second step is preferably performed in one or more catalytic distillation columns.

Production of Biodiesel According to Embodiments Disclosed Herein

Biodiesel has been produced by performing transesterification of vegetable oils and animal fats with methanol in the presence of homogeneous catalysts and solid catalyst. Feedstocks for the production of bio-diesel are vegetable oils and animal fats, which are esters of higher fatty acids. The term fat (vegetable or animal oil, if liquid) is usually confined to esters (glycerides) of fatty acids with glycerol, and the term wax to esters of other alcohols. The basic chemistry involved in producing bio-diesel is the catalytic exchange reaction of natural esters (mainly glycerides) with a primary alcohol (typically methanol or ethanol). An alcoholic solution of a base (usually NaOH, KOH, potassium methoxide, or sodium methoxide) may be used as a catalyst. Therefore, bio-diesel is a mixture of methyl or ethyl esters of various saturated and unsaturated fatty acids. Co-product is glycerol, which amounts from 16 to 25 wt %. Biodiesel may also contain some fatty acids (hydrolysis products of esters) in minor amounts depending on the amount of water in the feed or the catalyst used.

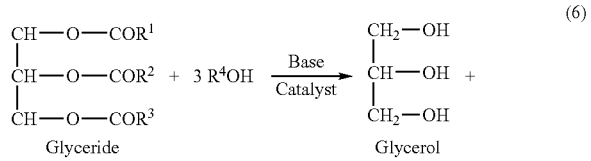

(6)

where $R^4OH$ = methanol or ethanol; $R = R^1, R^2$ or $R^3$.

The alkyl groups $R^1$, $R^2$ and $R^3$ of the natural product glyceride are, in general, different in the chain length and degree of unsaturation. The alkyl groups are usually straight chain and have even number of carbon atoms from 4 to 26. The exception is branched isovaleric acid $(CH_3)_2CHCH_2COOH$, which occurs in relatively large amounts in dolphins. Some unsaturated fatty acids have two or three double bonds in the alkyl chains. Unsaturated fatty acids have lower melting points than their saturated counter parts. The chain length of unsaturated fatty acids is generally in the range of $C_{10}$-$C_{24}$. Canola oil has a higher degree of unsaturation in $C_{16}$-$C_{20}$ chain length than corn oil.

In general, base catalysts are more effective for transesterification of carboxylic esters with an alcohol than acid catalysts. The heterogeneous catalysts disclosed in the prior art (see Background) are also base catalysts. Unfortunately, active catalytic components leach out of solid catalyst under the reaction condition, resulting catalyst deactivation. Zinc aluminate catalysts are not very active catalyst and require higher reaction temperatures and lower feed rates than more basic catalysts such as MgO or CaO. But the latter leach out of the solid catalyst even faster than the zinc aluminates.

Transesterification of vegetable oils or animal fats may be carried out with methanol or ethanol in the presence of a solid catalyst in a boiling point reactor, pulse flow reactor, or catalytic distillation column with a trace amount of soluble catalytic component in the feed mixture in a one step or two step reaction. Starting catalysts may include metal oxides, such as magnesium oxide, calcium oxide, zinc oxide, sodium oxide, potassium oxide, lanthanum oxide, etc., supported on a support, such as silica, alumina carbon and/or carbonaceous material. Carbon and carbonaceous supports will preferably have surface functional groups such as hydroxyl or carbonyl or both to immobilize organometallic compounds on the surface of the support.

To prepare supported metal oxides, hydroxides, or oxyhydroxides, the surface functional groups may not be necessary. Carbonaceous supports may be prepared by controlled thermal dehydration of carbohydrates, such as wood, coconut shell, starch, cellulose, a mixture of starch and cellulose, sugar, methyl cellulose, etc., at elevated temperatures. Carbonaceous supports may be either unsupported or supported. To prepare supported carbonaceous material, carbohydrates are deposed on a suitable porous support followed by controlled thermal dehydration at an elevated temperature from 300° C. to 1000° C. in an inert atmosphere or an atmosphere composed of an inert gas, a small amount of oxygen or steam or both. Support for carbonaceous materials may be any inorganic materials such as alumina, titania, silica, zirconia, clays, silica-alumina, etc.

In the two step process, the conversion of triglyceride across the first reactor may be higher than about 90%. Remaining unconverted triglyceride, diglyceride and monoglyceride in the reaction product stream from the first transesterification reactor may be converted to completion in the second transesterification reactor. Since the transesterification is a two phase reaction, performing transesterification in a boiling point or pulsed flow reactor will aid to transport large triglyceride molecules, methyl esters, and sticky glycerol through catalyst pores back and forth between bulk liquid medium and interior of catalyst pellets, where most catalytic reactions occur, resulting in high productivity. Since catalysts disclosed herein have high activity, the transesterification may be performed at a lower temperature and pressure, which means lower construction cost and utility cost.

The addition of soluble catalytic component to the feed stream to the reactors is from about 0.5 ppm to about 500 ppm by weight in some embodiments; from about 5 ppm to about 250 ppm by weight in other embodiments; and from 10 ppm to 50 ppm by weight in other embodiments. Examples of soluble catalytic compounds include zinc 2-methoxyethoxide, calcium 2-methoxyethoxide, zinc 2-methoxypropoxide, zinc ethoxide, zinc alkoxy alkyl carbonate, calcium 2-methoxyproxide, calcium ethoxide, calcium methoxide, calcium alkoxy alkyl carbonate, magnesium 2-methoxyethoxide, magnesium 2-methoxyproxide, magnesium ethoxide, magnesium methoxide, magnesium butoxide, magnesium alkoxy alkyl carbonate, lanthanum alkoxide, lanthanum alkoxy alkyl carbonate, zinc salts of carboxylic acids, magnesium salts of carboxylic acids, calcium salts of carboxylic acids, and Mg, Ca, and Zn glycerides, among others. A mixture of these may also be used. Soluble compounds of Ca, Mg, Zn and La may be obtained by reacting oxide or hydroxide of these metal with an organic carbonate or a mixture of organic carbonate and an alcohol, or carboxylic acids or a mixture of organic carboxylic acid and an alcohol such as methanol, 2-methoxyethanol, etc. at temperature from 93° C. to 260° C. (200° F. to 500° F.), preferably from 121° C. to 232° C. (250° F. to 450° F.) in liquid phase or presence of liquid and vapor. Optionally one may choose to recover the metal components for recycle. Such prepared solutions are useful for adding trace amount of these metal into the feed stream to a reactor to obtain a long catalyst cycle time. Total amount of active metal or metal components on a solid metal alkoxide, metal hydroxide or metal oxide catalyst is from about 0.05 wt % to about 20 wt % in some embodiments, and from about 0.07 wt % to about 12 wt % in other embodiments.

Optionally, all or a part of di- or mono-glycerides may be converted to organic carbonates or organic carbamates or both by reaction with DMC, methyl 2-ethyl-1-hexyl carbonate, methyl carbamate, 2-ethyl-1-hexyl carbamate, urea, or a mixture of these in addition to transesterification with methanol in the second reactor or optionally in a third reactor. The resulting organic carbonates and carbamates may serve as a biodiesel additive agent for reducing particulates, $NO_x$ emissions, or improvement of diesel cetane.

As natural vegetable oils may contain various minor amounts of free fatty acids, free fatty acids needed to be removed by pretreatment prior to performing transesterification with an alcohol in the presence of a solid base catalyst. An example of such pretreatment methods is esterification of free fatty acids with methanol in the presence of an acid catalyst. One such acid catalyst is sulfonic acid immobilized on a carbonaceous support. Support may include those prepared by controlled thermal dehydration of coconut shell or carbohydrates supported or deposited on a porous support. Performing esterification of free fatty acids with an alcohol in the presence of a solid acid catalyst in a catalytic distillation reactor has advantages, which are continuous removal of water from the reaction zone as an overheads stream, driving the esterification toward completion and eliminating a separate drying step of the esterification product prior to performing transesterification of triglyceride with an alcohol. Another important advantage is decreased esterification times.

All transesterification reactions in the following examples were performed in down-flow reactors. The dimension of the fixed bed reactor was 1.3 cm (½ inch) diameter by 53.3 cm (21 inches) long. The reactor had separately controlled top and bottom heating zones. The feed methanol stream and vegetable oil stream (6 wt % methanol in vegetable oil) were separately pumped into the top section of the reactor, where the two streams flow down into the catalytic reaction zone. Trace amounts of soluble catalytic component were blended into a methanol stream or already contained partially converted product stream. The volume of solid catalysts was 15 ml.

Experiment 13

The objective of this experiment was to demonstrate the transesterification of canola oil with methanol in the presence of a solid catalyst in a down-flow boiling reactor or catalytic distillation reactor. The solid catalyst is MgO supported on a silica gel.

A magnesium nitrate solution was prepared by dissolving 10.96 g $Mg(NO_3)_2.6H_2O$ in 24 g deionized water. 30 ml (11.91 g) of a silica gel sphere support (1.7-4 mm diameter; about 6 hydroxyl groups per $nm^2$, 314 $m^2$/g BET, 1.055 $cm^3$/g pore volume and 13.46 nm average pore diameter) was impregnated with the above magnesium nitrate solution by an incipient wetness technique. The silica gel sphere support was prepared by an oil dropping technique. After drying the impregnation product at 100° C. for 1 hour, it was then calcined at 510° C. for 2 hrs.

15 ml (6.30 g) of the $MgO/SiO_2$ catalyst was loaded in the reactor. Canola oil feed (purchased from a local grocery store) was prepared by mixing methanol (5.39 wt %) with the canola oil (94.61 wt %). The acid value of free fatty acid of this feed was 0.48 mg KOH/g. The transesterification of canola oil with methanol was performed at 165° C. (330° F.) and 19.4 bar (267 psig) by feeding the canola oil feed and methanol at 0.2 ml/min each. Magnesium ethoxide was dissolved in the methanol feed to have 28 ppm Mg by weight in the catalytic reaction zone.

Figure 17:
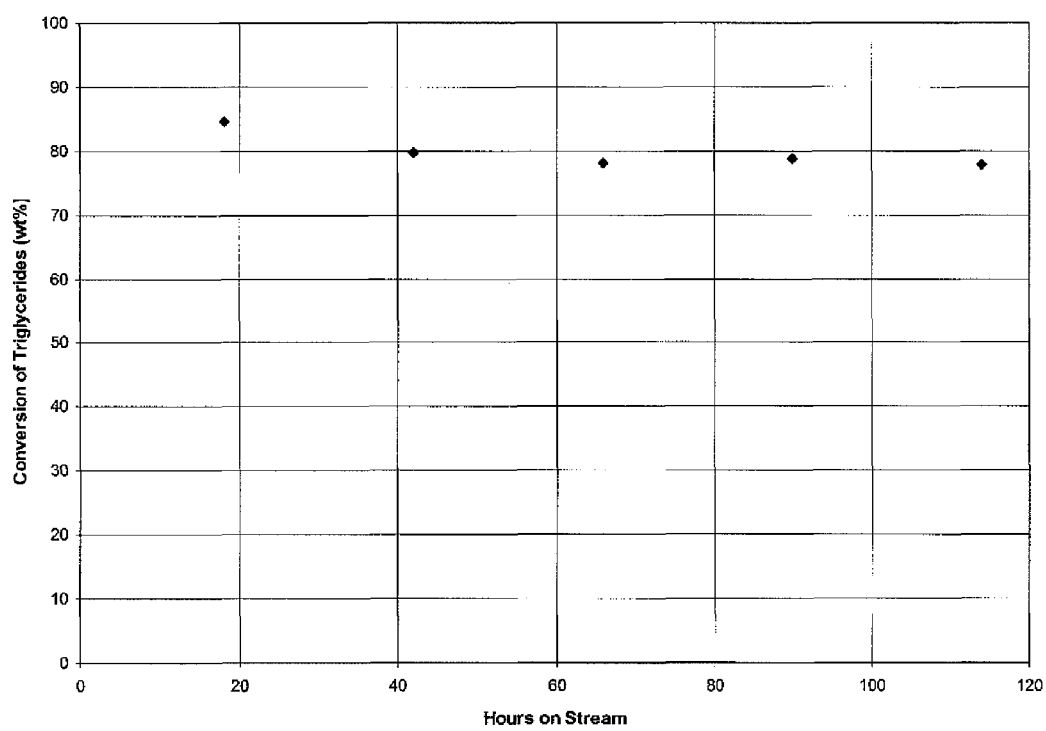
FIG. 17 presents results from the alcoholysis of canola oil with methanol using a solid catalyst according to embodiments disclosed herein.

The effluent streams were composed of two clear layers. Top layers contain the product methyl esters and small amounts of unconverted triglycerides. The average content of unconverted triglycerides in the reaction products, excluding methanol from the top layers, was about 1.2 wt %. The bottom layer contains most of the unconverted triglycerides. The result is illustrated in FIG. 17, which indicates a stable catalyst performance.

Experiment 14

The objective of this experiment was to demonstrate converting the remaining unconverted or partially converted materials in the effluent stream (two layers on standing) from the first reactor, in a second down-flow boiling point reactor or catalytic distillation reactor, or optionally recycle to the front of a single transesterification reactor.

A magnesium nitrate solution was prepared by dissolving 9.04 g $Mg(NO_3)_2.6H_2O$ in 19.1 g deionized water. 22 ml (9.14 g) of a silica gel sphere support (9-14 mesh, 309 m²/g BET and 1.03 cm³/g pore volume) was impregnated with above magnesium nitrate solution by incipient wetness technique. After drying the impregnation product at 150° C. for 1 hour, it was calcined at 510° C. for 2 hrs. The fished catalyst contained 4.5% Mg by weight.

15 ml (7.2 g) of the MgO/SiO₂ catalyst was loaded in the same reactor used in Experiment 13. The two layers of a composite product from the first transesterfication reaction of canola oil with methanol were separated from the composite product by using a separation funnel to be used as feeds for the second transesterfication reaction. The composition of the bottom composite product feed was 25.4 wt % triglycerides, 8.5 wt % diglycerides, 3.1 wt % monoglycerides, 0.1 wt % glycerin, 47.1 wt % methyl esters and 15.8 wt % methanol. The feed contained about 8.5 ppm soluble Mg species by weight and had 0.32 mg KOH/g free fatty acid value. Transesterification was performed at 160° C. (320° F.) and 19.5 bar (268 psig) by pumping 0.12 ml/min feed and 0.10 ml/min methanol into the down-flow boiling point reactor. No additional Mg alkoxide was added into either of the two feed streams. The reactor effluent stream was a clear light yellow solution (single layer).

The composition of the top composite product feed was 1.12 wt % triglycerides, 0.57 wt % diglycerides, 3.78 wt % monoglycerides, 7.47 wt % methyl esters, 0.03 wt % glycerin and 87.03 wt % methanol. The free fatty acid value of this feed was 0.51 mg KOH/g. The transesterification was performed over the same catalyst at the same temperature and pressure at a 0.2 ml/min feed flow rate. No additional methanol was pumped into the reactor. These two final transesterification products from composite bottom and top composite product feeds were combined to distill off excess methanol and to recover crude biodiesel. The recovered crude biodiesel contained 0.36 wt % unconverted triglycerides and 0.74 mg KOH/g free fatty acid value.

The above experimental result successfully demonstrates that biodiesl can be produced by performing transesterification of vegetable oil with an alcohol such as methanol in the presence of a solid catalyst As described above, embodiments disclosed herein provide for extended catalyst cycle times for various solid catalysts through the introduction of a trace amount of soluble organometallic compounds with the feed. Other embodiments disclosed herein may include a method for continuously producing organic carbonate or organic carbamate at a stable rate; techniques for in situ catalyst preparation of immobilized solid catalysts, techniques for maintaining stable catalyst activity for long catalyst cycle times and service times so as to be suitable for commercial fixed bed reactors; and an in situ method of reactivating deactivated solid catalysts.

Advantageously, embodiments disclosed herein may provide for transesterification catalysts having an extended cycle length, therefore decreasing operational costs associated with frequent shut downs and catalyst changes. Additionally, due to the trace amount of soluble organometallic compound used, removing the homogeneous catalyst from various product streams may be substantially reduced.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. An alcoholysis process for producing diaryl carbonates, comprising:
feeding reactants and a trace amount of soluble organometallic compound to a reactor comprising a solid alcoholysis catalyst;
wherein the soluble organometallic compound and the solid alcoholysis catalyst each independently comprise a Group II to Group VI element.

2. The process of claim 1, wherein the alcoholysis is a transesterification.

3. The process of claim 1, wherein the alcoholysis is a disproportionation.

4. The process of claim 1, wherein the soluble organometallic compound and the solid alcoholysis catalyst each comprise the same Group II to Group VI element.

5. The process of claim 1, comprising:
contacting the reactants in the presence of the solid alcoholysis catalyst to alcoholyze at least a portion of the reactants; and
recovering a reactor effluent comprising the soluble organometallic compound, alcoholysis product, and unreacted reactants.

6. The process of claim 1, wherein the soluble organometallic compound is fed at a rate in the range of 1 ppm to 2000 ppm by weight, based on a total weight of the feed reactants.

7. The process of claim 1, wherein the solid alcoholysis catalyst comprises at least one of an immobilized organotitanium compound and a supported titanium compound, and the soluble organometallic compound comprises a titanium compound soluble in the feed reactants.

8. The process of claim 1, wherein the solid alcoholysis catalyst comprises at least one of an immobilized organocalcium compound and a supported calcium compound, and the soluble organometallic compound comprises a calcium compound soluble in the feed reactants.

9. The process of claim 1, wherein the solid alcoholysis catalyst comprises at least one of an immobilized organomagnesium compound and a supported magnesium compound, and the soluble organometallic compound comprises a magnesium compound soluble in the feed reactants.

10. The process of claim 1, wherein the solid alcoholysis catalyst comprises at least one of an immobilized organozinc compound and a supported zinc compound, and the soluble organometallic compound comprises a zinc compound soluble in the feed reactants.

11. The process of claim 1, wherein the solid alcoholysis catalyst comprises at least one of an immobilized organotin compound and a supported tin compound, and the soluble organometallic compound comprises a tin compound soluble in the feed reactants.

12. The process of claim 1, wherein the solid alcoholysis catalyst comprises at least one of an immobilized organoantimony compound and a supported antimony compound, and the soluble organometallic compound comprises an antimony compound soluble in the feed reactants.

13. The process of claim 3, further comprising recovering at least a portion of the soluble organometallic compound from the reactor effluent.

14. The process of claim 13, further comprising recycling at least a portion of the recovered soluble organometallic compound to the alcoholysis reactor.

* * * * *